US012810635B2

(12) United States Patent
Hu et al.

(10) Patent No.: US 12,810,635 B2
(45) Date of Patent: Nov. 24, 2026

(54) METHOD OF PROCESSING MEDICAL DATA, METHOD OF ANALYZING MEDICAL DATA, ELECTRONIC DEVICE, AND MEDIUM

(71) Applicant: BOE TECHNOLOGY GROUP CO., LTD., Beijing (CN)

(72) Inventors: Yulan Hu, Beijing (CN); Zhenzhong Zhang, Beijing (CN); Xiaotian Jiang, Beijing (CN)

(73) Assignee: Beijing BOE Technology Development Co., Ltd., Beijing (CN)

( * ) Notice: Subject to any disclaimer, the term of this patent is extended or adjusted under 35 U.S.C. 154(b) by 324 days.

(21) Appl. No.: 18/550,267

(22) PCT Filed: Nov. 11, 2022

(86) PCT No.: PCT/CN2022/131414
§ 371 (c)(1),
(2) Date: Sep. 12, 2023

(87) PCT Pub. No.: WO2024/098387
PCT Pub. Date: May 16, 2024

(65) Prior Publication Data

US 2024/0331416 A1 Oct. 3, 2024

(51) Int. Cl.
*G06V 20/69* (2022.01)
*A61B 5/00* (2006.01)
(Continued)

(52) U.S. Cl.
CPC .......... *G06V 20/698* (2022.01); *A61B 5/0042* (2013.01); *G06T 7/0016* (2013.01);
(Continued)

(58) Field of Classification Search
CPC .............. G06V 20/698; G06V 10/7715; A61B 5/0042; G06T 2207/30016; G06T 2207/30096; G06T 7/0012
See application file for complete search history.

(56) References Cited

U.S. PATENT DOCUMENTS

| | | | |
|---|---|---|---|
| 11,321,842 B1 | 5/2022 | Tiwari et al. | |
| 2007/0118399 A1* | 5/2007 | Avinash ................ | G16H 10/60 705/2 |

(Continued)

FOREIGN PATENT DOCUMENTS

| | | |
|---|---|---|
| CN | 105653858 A | 6/2016 |
| CN | 108376558 A | 8/2018 |

(Continued)

OTHER PUBLICATIONS

Decuyper, Milan, et al. "Automated MRI based pipeline for segmentation and prediction of grade, IDH mutation and 1p19q codeletion in glioma." Computerized Medical Imaging and Graphics 88 (2021): 101831. (Year: 2021).*

(Continued)

*Primary Examiner* — Emily C Terrell
*Assistant Examiner* — Jacqueline R Zak
(74) *Attorney, Agent, or Firm* — Kinney & Lange, P.A.

(57) ABSTRACT

The present disclosure provides a method of processing medical data, which includes: acquiring first medical image data; inputting the first medical image data into a first feature extraction network to obtain a first image feature; and obtaining a first gene mutation information according to the first image feature. The first feature extraction network includes a first feature extraction module configured to: determine a first image query matrix and a first image key matrix according to the first medical image data; determine a first image weight matrix according to the first image query matrix and the first image key matrix, where the first image (Continued)

weight matrix represents a correlation information between each two first medical images in the first medical image data; and determine the first image feature according to the first image weight matrix and the first medical image data.

19 Claims, 23 Drawing Sheets

(51) Int. Cl.

| | |
|---|---|
| ***G06T 7/00*** | (2017.01) |
| ***G06V 10/62*** | (2022.01) |
| ***G06V 10/70*** | (2022.01) |
| ***G06V 10/77*** | (2022.01) |
| ***G06V 10/774*** | (2022.01) |
| ***G06V 10/80*** | (2022.01) |
| ***G06V 20/50*** | (2022.01) |
| ***G16B 40/20*** | (2019.01) |

(52) U.S. Cl.

CPC .......... *G06V 10/62* (2022.01); *G06V 10/7715* (2022.01); *G06V 10/774* (2022.01); *G06V 10/806* (2022.01); *G06V 10/87* (2022.01); *G06V 20/50* (2022.01); *G16B 40/20* (2019.02); *G06T 2207/20081* (2013.01); *G06T 2207/20084* (2013.01); *G06T 2207/30016* (2013.01); *G06T 2207/30096* (2013.01); *G06V 2201/03* (2022.01)

(56) References Cited

U.S. PATENT DOCUMENTS

| | | | | |
|---|---|---|---|---|
| 2014/0142983 | A1* | 5/2014 | Backhaus .............. | G16H 30/40<br>705/3 |
| 2021/0319907 | A1 | 10/2021 | Harley et al. | |
| 2022/0156935 | A1 | 5/2022 | Tiwari et al. | |
| 2023/0019211 | A1* | 1/2023 | Wang ................... | G06N 3/0464 |
| 2023/0145535 | A1* | 5/2023 | Hatamizadeh ........... | G06N 3/02<br>514/460 |

FOREIGN PATENT DOCUMENTS

| | | | |
|---|---|---|---|
| CN | 111161882 | A | 5/2020 |
| CN | 111488914 | A | 8/2020 |
| CN | 113077875 | A | 7/2021 |
| CN | 113228194 | A | 8/2021 |
| CN | 113707278 | A | 11/2021 |
| CN | 113989552 | A | 1/2022 |
| CN | 114171157 | A | 3/2022 |
| CN | 114190884 | A | 3/2022 |
| CN | 114496151 | A | 5/2022 |
| CN | 114724016 | A | 7/2022 |
| CN | 115238698 | A | 10/2022 |
| KR | 20200004204 | A | 1/2020 |

OTHER PUBLICATIONS

Wu, Yujiao, et al. "Multimodal learning for non-small cell lung cancer prognosis." arXiv.org. Nov. 7, 2022. (Year: 2022).*

Author Unknown, Thesis for Master Degree of Shandong University, Research on Algorithms of Thyroid Image Recognition and Report Generation Based on Multi-task Network, May 30, 2021.

International Search Report and Written Opinion dated May 25, 2023, for corresponding PCT Application No. PCT/CN2022/131414.

Jun Li, et al., Cervical Cell Multi-Classification Algorithm Using Global Context Information and Attention Mechanism, "Time and Cell" 74 (2022).

Sheng He et al., Brain Age Estimation Using LSTM on Children's Brain MRI, 2020 IEEE 17th International Symposium on Biomedical Imaging, Apr. 3-7, 2020.

Wang Chen, et al., Multi-Energy Load Forecasting in Integrated Energy System Based on ResNet-LSTM Network and Attention Mechanism, Transactions of China Electrotechnical Society vol. 37 No. Apr. 7, 2022.

* cited by examiner

500A

500C

1200

Detection Report

Basic information:

Name: Zhang San, Age: 59, Gender: Male, Height: 176 CM, Weight: 78 KG, Glioma Grade: G4

Gene mutation information prediction result:

| item | result |
| --- | --- |
| IDH | no mutation (wild-type) |
| 1p/19q | no deletion |
| TERT | no mutation (wild-type) |
| MGMT | no methylation |

Survival information prediction result:

Patient survival>5 years

MRI sampling:

METHOD OF PROCESSING MEDICAL DATA, METHOD OF ANALYZING MEDICAL DATA, ELECTRONIC DEVICE, AND MEDIUM

CROSS-REFERENCE TO RELATED APPLICATION

This application is a Section 371 National Stage Application of International Application No. PCT/CN2022/131414, filed Nov. 11, 2022, which is incorporated herein by reference in its entirety.

TECHNICAL FIELD

The present disclosure relates to a field of an artificial intelligence technology, in particular to a field of a deep learning technology. More specifically, the present disclosure relates to a method of processing medical data, a method of analyzing medical data, an electronic device, and a medium.

BACKGROUND

With a development of the artificial intelligence technology, the artificial intelligence technology has been widely applied in various fields. For example, in a field of medicine, the artificial intelligence technology may be used to process and analyze medical data, so as to obtain a gene mutation prediction result and a survival prediction result.

SUMMARY

In view of the above, the present disclosure provides a method of processing medical data, a method of analyzing medical data, an electronic device, and a medium.

According to an aspect of the present disclosure, a method of processing medical data is provided, including: acquiring first medical image data; inputting the first medical image data into a first feature extraction network to obtain a first image feature; and obtaining a first gene mutation information according to the first image feature, where the first feature extraction network includes a first feature extraction module configured to: determine a first image query matrix and a first image key matrix according to the first medical image data; determine a first image weight matrix according to the first image query matrix and the first image key matrix, where the first image weight matrix represents a correlation information between each two first medical images in the first medical image data; and determine the first image feature according to the first image weight matrix and the first medical image data. The first medical image data includes a brain glioma image. The obtaining a first gene mutation information according to the first image feature includes: inputting the first image feature to a classification network to obtain a brain glioma gene mutation type.

According to another aspect of the present disclosure, a method of processing medical data is provided, including: acquiring first medical text data and second medical image data; obtaining a second image feature according to the second medical image data; inputting the first medical text data into the second feature extraction network to obtain a first text feature; fusing the second image feature with the first text feature to obtain a first fusion feature; and obtaining a first survival information according to the first fusion feature.

According to an aspect of the present disclosure, a method of analyzing medical data is provided, including: acquiring second medical text data and third medical image data; inputting the third medical image data into a third feature extraction network to obtain a third image feature; determining a second gene mutation information according to the third image feature; inputting the second medical text data into a fourth feature extraction network to obtain a second text feature; and determining a second survival information according to a fusion feature obtained from the third image feature and the second text feature; where the third feature extraction network includes a fourth feature extraction module configured to: determine a third image query matrix and a third image key matrix according to the third medical image data; determine a third image weight matrix according to the third image query matrix and the third image key matrix, where the third image weight matrix represents a correlation information between each two third medical images in the third medical image data; and determine the third image feature according to the third image weight matrix and the third medical image data.

In another aspect of the present disclosure, an electronic device is provided, including: one or more first processors; and a memory for storing one or more programs, where the one or more programs are configured to, when executed by the one or more processors, cause the one or more first processors to implement the methods described in the present disclosure.

In another aspect of the present disclosure, a non-transitory computer readable storage medium having computer executable instructions stored therein is provided, and the instructions are configured to, when executed by a processor, cause the processor to implement the methods described in the present disclosure.

In another aspect of the present disclosure, a computer program product containing a computer program, where the computer program is configured to, when executed by a processor, cause the processor to implement the methods described in the present disclosure.

BRIEF DESCRIPTION OF THE DRAWINGS

The above and other objectives, features and advantages of the present disclosure will be clearer with following descriptions of the present disclosure with reference to the accompanying drawings, in which.

DETAILED DESCRIPTION OF EMBODIMENTS

Figure 1:
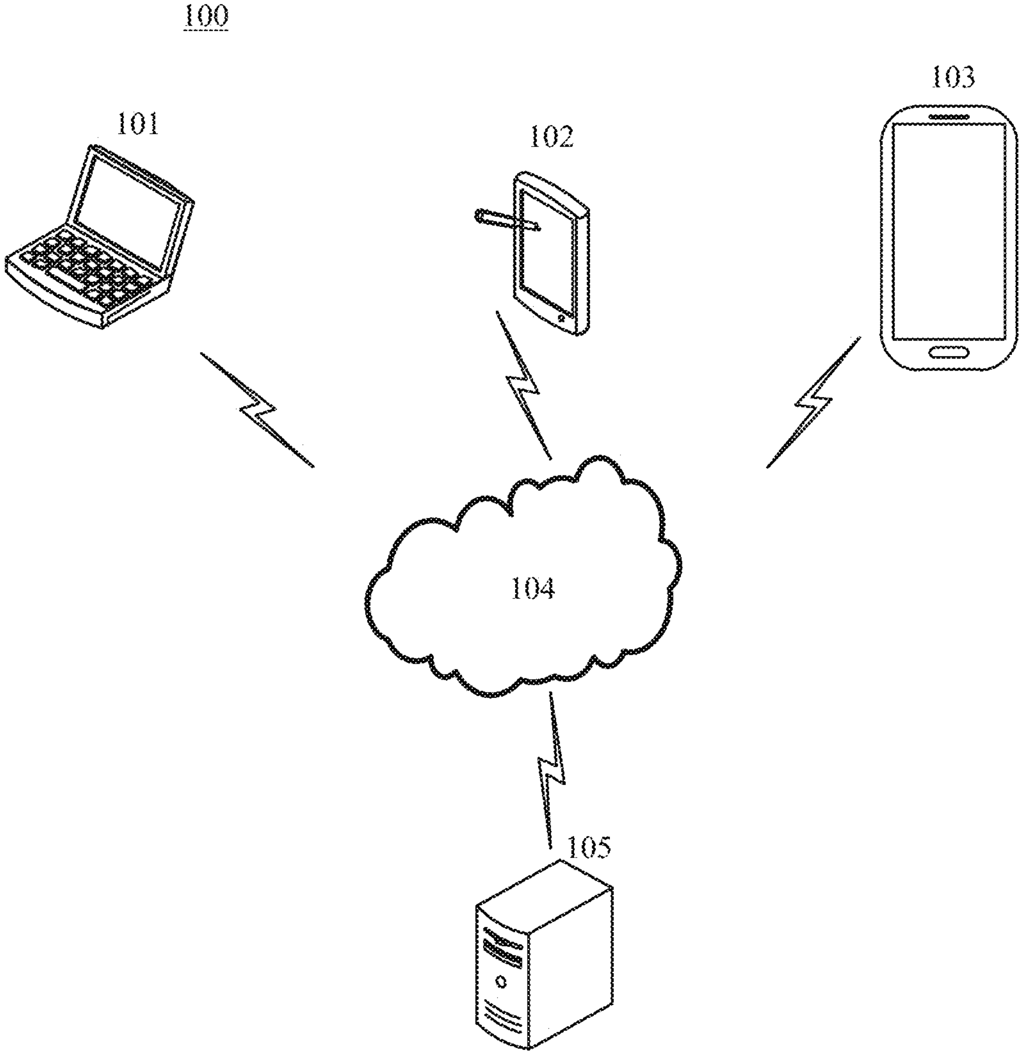
FIG. 1 schematically shows an exemplary system architecture to which a method and apparatus of processing medical data and a method and apparatus of analyzing medical data may be applied according to an embodiment of the present disclosure.

Embodiments of the present disclosure will be described below with reference to the accompanying drawings. It should be understood, however, that these descriptions are merely exemplary and are not intended to limit the scope of the present disclosure. In the following detailed description, for ease of interpretation, many specific details are set forth to provide a comprehensive understanding of embodiments of the present disclosure. However, it is clear that one or more embodiments may also be implemented without these specific details. In addition, in the following description, descriptions of well-known structures and technologies are omitted to avoid unnecessarily obscuring the concepts of the present disclosure.

Terms used herein are only for describing specific embodiments and are not intended to limit the present disclosure. The terms “including”, “containing”, etc. used herein indicate the presence of the feature, step, operation and/or component, but do not exclude the presence or addition of one or more other features, steps, operations or components.

All terms used herein (including technical and scientific terms) have the meanings generally understood by those skilled in the art, unless otherwise defined. It should be noted that the terms used herein shall be interpreted to have meanings consistent with the context of this specification, and shall not be interpreted in an idealized or overly rigid manner.

In a case of using the expression similar to “at least one of A, B and C”, it should be explained according to the meaning of the expression generally understood by those skilled in the art (for example, “a system including at least one of A, B and C” should include but not be limited to a system including A alone, a system including B alone, a system including C alone, a system including A and B, a system including A and C, a system including B and C, and/or a system including A, B and C). In a case of using the expression similar to “at least one of A, B or C”, it should be explained according to the meaning of the expression generally understood by those skilled in the art (for example, “a system including at least one of A, B or C” should include but not be limited to a system including A alone, a system including B alone, a system including C alone, a system including A and B, a system including A and C, a system including B and C, and/or a system including A, B and C).

With a development of high-throughput arrays and next-generation sequencing technologies, a genome analysis has been widely applied, and it is possible to perform a gene mutation detection and a survival prediction based on the genome analysis. The gene mutation detection and the survival prediction have significant clinical significance for at least one of disease grading, molecular typing, medication guidance and prognostic evaluation of symptoms. However, current gene mutation detection methods and survival prediction methods may have damage to an object. In addition, a correlation between the gene mutation testing and the survival prediction is not taken into account, which results in a long sequencing time and high testing costs.

Therefore, embodiments of the present disclosure provide a solution of processing medical data. For example, first medical image data may be acquired, the first medical image data is input into a first feature extraction network to obtain a first image feature, and a first gene mutation information is obtained according to the first image feature. The first feature extraction network includes a first feature extraction module, which is configured to: determine a first image query matrix and a first image key matrix according to the first medical image data; determine a first image weight matrix according to the first image query matrix and the first image key matrix, where the first image weight matrix represents a correlation information between each two first medical images in the first medical image data; and determine the first image feature according to the first image weight matrix and the first medical image data.

According to the embodiments of the present disclosure, since the first image feature is determined according to the first medical image data and the first image weight matrix, the first image feature may represent a correlation information between each two first medical images in the first medical image data. In addition, the first image feature obtained through the first feature extraction network may accurately characterize the first medical image data. On this basis, the first gene mutation information is obtained according to the first image feature, thereby achieving a combination of image data feature extraction and gene mutation information testing, so that the comprehensiveness and accuracy of the gene mutation detection may be improved.

In technical solutions of the present disclosure, a collection, a storage, a use, a processing, a transmission, a provision, a disclosure and other processing of user personal information involved comply with provisions of relevant laws and regulations and do not violate public order and good custom.

In the technical solutions of the present disclosure, the acquisition or collection of user personal information has been authorized or allowed by users.

FIG. 1 schematically shows an exemplary system architecture to which a method and apparatus of processing medical data and a method and apparatus of analyzing medical data may be applied according to an embodiment of the present disclosure.

It should be noted that FIG. 1 is merely an example of the system architecture to which embodiments of the present disclosure may be applied, so as to help those skilled in the art understand technical contents of the present disclosure. However, it does not mean that the embodiments of the present disclosure may not be applied to other devices, systems, environments or scenarios. For example, in another embodiment, the exemplary system architecture to which the method and apparatus of processing the medical data and the method and apparatus of analyzing the medical data may be applied may include a terminal device, but the terminal device may implement the method and apparatus of processing the medical data and the method and apparatus of analyzing the medical data provided in the embodiments of the present disclosure without interacting with a server.

As shown in FIG. 1, a system architecture 100 according to such embodiments may include terminal devices 101, 102 and 103, a network 104, and a server 105. The network 104 may provide a medium for communication link between the terminal devices 101, 102, 103 and the server 105. The network 104 may include various connection types, such as wired and/or wireless communication links.

The terminal devices 101, 102 and 103 may be used by a user to interact with the server 105 through the network 104, so as to receive or send messages, etc. The terminal devices 101, 102, 103 and the server 105 may be installed with various communication client applications, which may include at least one selected from applets and applications (APPs). For example, the communication client applications may include at least one selected from shopping applications, web browser applications, search applications, instant messaging tools, email clients, social platform software, etc.

The terminal devices 101, 102 and 103 may be various electronic devices having display screens and supporting web browsing, including at least one selected from smart phones, tablet computers, laptop computers, desktop computers, etc.

The server 105 may be various types of servers that provide various services. For example, the server 105 may be a cloud server, also known as a cloud computing server or a cloud host, which is a host product in a cloud computing service system to solve shortcomings of difficult management and weak business scalability existing in a conventional physical host and VPS (Virtual Private Server) service. The server 105 may also be a server of a distributed system or a server combined with a block-chain.

It should be noted that the method of processing the medical data and the method of analyzing the medical data provided in embodiments of the present disclosure may generally be performed by the terminal device 101, 102 or 103. Accordingly, the apparatus of processing the medical data and the apparatus of analyzing the medical data provided in embodiments of the present disclosure may also be provided in the terminal device 101, 102 or 103.

Alternatively, the method of processing the medical data and the method of analyzing the medical data provided in embodiments of the present disclosure may generally be performed by the server 105. Accordingly, the apparatus of processing the medical data and the apparatus of analyzing the medical data provided in embodiments of the present disclosure may be generally provided in the server 105. The method of processing the medical data and the method of analyzing the medical data provided in embodiments of the present disclosure may also be performed by a server or server cluster which is not the server 105 and is capable of communicating with the terminal devices 101, 102, 103 and/or the server 105. Accordingly, the apparatus of processing the medical data and the apparatus of analyzing the medical data provided in embodiments of the present disclosure may also be provided in a server or server cluster which is not the server 105 and is capable of communicating with the terminal devices 101, 102, 103 and/or the server 105.

It should be understood that the numbers of terminal devices, network and server shown in FIG. 1 are merely schematic. According to implementation needs, any number of terminal devices may be provided, any number of networks may be provided, and any number of servers may be provided.

It should be noted that a sequence number of each operation in the following methods is merely used to represent the operation for ease of description, and should not be regarded as indicating an order in which the operations are performed. Unless explicitly stated, the methods do not need to be performed exactly in the order shown.

Figure 2:
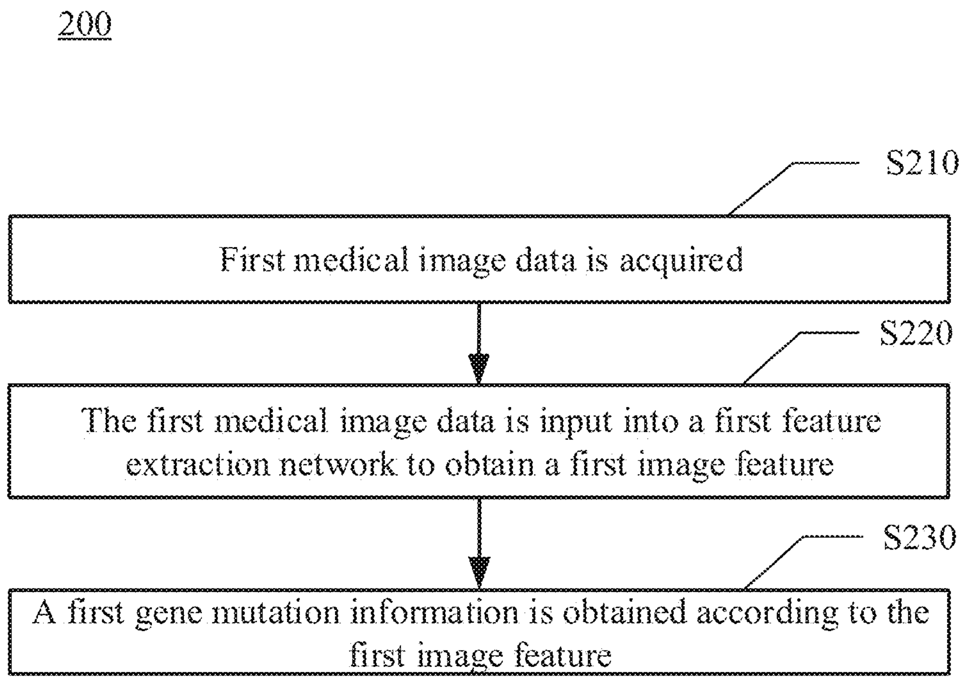
FIG. 2 schematically shows a flowchart of a method of processing medical data according to an embodiment of the present disclosure.

FIG. 2 schematically shows a flowchart of a method of processing medical data according to an embodiment of the present disclosure.

As shown in FIG. 2, a method 200 includes operation S210 to operation S230.

In operation S210, first medical image data is acquired.

In operation S220, the first medical image data is input into a first feature extraction network to obtain a first image feature.

In operation S230, a first gene mutation information is obtained according to the first image feature.

According to embodiments of the present disclosure, the first feature extraction network may include a first feature extraction module. The first feature extraction module may be used to: determine a first image query matrix and a first image key matrix according to the first medical image data; determine a first image weight matrix according to the first image query matrix and the first image key matrix, where the first image weight matrix may represent a correlation information between each two first medical images in the first medical image data; and determine the first image feature according to the first image weight matrix and the first medical image data.

According to embodiments of the present disclosure, the first medical image data may be acquired from a data source in response to a detection of a medical data processing instruction. The data source may include at least one selected from: a local database, a cloud database, or a network resource. The data source may be constructed based on at least one of a user medical information obtained by a questionnaire survey of a user, or a user medical information obtained by an analysis of historical behavioral data of a user. The cloud database may include a TCGA (the Cancer Genome Atlas) database and a TCIA (the Cancer Immunome Atlas) database. It is possible to invoke a data interface and acquire the first medical image data from the data source by using the data interface. Alternatively, it is possible to acquire a user information input by a user from the medical data processing instruction in response to the detection of the medical data processing instruction.

According to embodiments of the present disclosure, the first medical image data may refer to important data in the field of medicine, which acts as a significant role in assisting doctors in diagnosis and pathological research. The first medical image data may be used to perform a gene mutation detection. The first medical image data may include at least one selected from: MRI (Magnetic Resonance Imaging) image data, CT (Computerized Tomography) image data, ECT (Emission Computed Tomography) image data, PET (Positron Emission Computed Tomography) image data, ultrasound image data, OCT (Optical Coherence Tomography) image data, or X-ray image data. The first medical image data may be three-dimensional medical image data.

According to embodiments of the present disclosure, the first medical image data may include at least one of mono-modality image data or multi-modality image data. The multi-modality image data may refer to different forms of same image data, or at least two different types of medical image data. For example, the MRI image data may be multi-modality MRI image data, which may include at least two selected from: T1 modal image data (i.e., T1 weighted image data), T2 modal image data (i.e., T2 weighted image data), T1CE modal image data (i.e., contrast-enhanced T1 weighted image data), or FLAIR (Fluid Attenuated Inversion Recovery) modal image data.

According to embodiments of the present disclosure, when the first medical image data is mono-modality medical image data, a mono-modality image feature may correspond to the mono-modality medical image data. When the first medical image data is multi-modality medical image data, a multi-modality image feature may include one or at least two of a plurality of modals. For example, when the multi-modality medical image data is a multi-modality MRT image, the multi-modality image feature may include at least one selected from a T1 modality, a T2 modality, a T1CE modality, or a FLAIR modality.

According to embodiments of the present disclosure, a tumor may include a primary tumor and a secondary tumor. The primary tumor may include a benign tumor and a malignant tumor. The lesion may be related to a gene mutation.

For example, when the first medical image data is brain-related image data, the brain tumor may include at least one of acoustic neuroma, pituitary adenoma, meningioma, tumor derived from embryonic residual tissue, or neuroglioma (i.e., brain glioma). The tumor derived from embryonic residual tissue may include at least one of craniopharyngioma, epidermoid cyst, or chordoma. The brain glioma may include at least one of glioblastoma, astrocytoma, oligodendroglioma, or medulloblastoma. According to a malignant level of tumor, the brain glioma may include at least one of low-grade brain glioma or high-grade brain glioma. The low-grade brain glioma is a benign tumor with good prognosis. The high-grade brain glioma is a malignant tumor with poor prognosis. A gene feature testing for brain glioma may be a basis for a precise diagnosis and treatment of brain glioma.

According to embodiments of the present disclosure, multi-gene mutation corresponding to brain glioma may include at least two of Isocitrate: NAD+Oxidoreductase (Decarboxylating) mutation (IDH mutation), chromosome 1p/19q co-deletion mutation, telomerase reverse tranase (TERT) mutation, $O^6$-Methylguanine-Deoxyribose Nucleic Acid Methyltransferase (MGMT) promoter methylation mutation, epidermal growth factor receptor variant (EGFRv) amplification, X-linked alpha thalassemia and mental retardation Syndrome(ATRX), or Notch signaling pathway.

According to embodiments of the present disclosure, after the first medical image data is acquired, the first medical image data may be processed using a first feature extraction network, so as to obtain the first image feature. The first feature extraction network may include a first deep learning model that may process the medical data. The first feature extraction network may be obtained by training a first deep learning model using first sample medical image data. A model structure of the first deep learning model may be determined according to actual service needs, and is not limited here. For example, the first deep learning model may include at least one model structure. The model structure may include at least one model sub-structure and a connection relationship between model sub-structures.

According to embodiments of the present disclosure, the first deep learning model may include at least one selected from: a first deep learning model based on a convolutional neural networks (CNN), a first deep learning model based on a recurrent neural network (RNN), or a first deep learning model based on Transformer. A method of training the first deep learning model may be determined according to actual service needs, and is not limited here. For example, the training method may include at least one selected from: unsupervised training, supervised training, or semi-supervised training.

According to embodiments of the present disclosure, the first gene mutation information may be set according to actual service needs and is not limited here. For example, when an organ corresponding to the first medical image data is the brain, the first gene mutation information may include at least two of a first IDH mutation information, a first chromosome 1p/19q co-deletion mutation information, a first TERT mutation information, or a first MGMT promoter methylation mutation information. Alternatively, when the organ corresponding to the first medical image data is the lung, the first gene mutation information may include at least two of an EGFR (Epidermal Growth Factor Receptor) mutation information or a KRAS (V-Ki-ras2 Kirsten Rat-sarcoma Viral Oncogene Homolog) mutation information, etc. Alternatively, when the organ corresponding to the first medical image data is the colorectum, the first gene mutation information may include at least two of a KRAS mutation information, an NRAS mutation information, a BRAF mutation information, or the like.

According to embodiments of the present disclosure, the first medical image data may include a medical image data sequence. The medical image data sequence may include medical image parameter matrices respectively corresponding to the plurality of first medical images. The medical image parameter matrices may represent the corresponding first medical images, respectively. The first image query matrices respectively corresponding to the plurality of first medical images and the first image key matrices respectively corresponding to the plurality of first medical images may be determined by performing linear transformation operations on the plurality of medical image parameter matrices respectively.

According to embodiments of the present disclosure, after the first image query matrices and the first image key matrices are obtained, a plurality of first image weight matrices respectively corresponding to the plurality of first medical images may be determined according to the first image query matrices respectively corresponding to the plurality of first medical images and the first image key matrices respectively corresponding to the plurality of first medical images. The first image weight matrix may represent a correlation information between each two first medical images in the plurality of first medical images. For example, matrix multiplication may be performed on a first image query matrix and a first image key matrix which are both correspond to a $t^{th}$ first medical image in the plurality of first medical images, so as to obtain a first image weight matrix for the $t^{th}$ first medical image. The correlation information may include a first correlation information and a second correlation information. The first correlation information may be used to represent a correlation information between a $(t-1)^{th}$ first medical image and the $t^{th}$ first medical image. The second correlation information may be used to represent a correlation information between the $t^{th}$ first medical image and a $(t+1)^{th}$ first medical image.

According to embodiments of the present disclosure, since the first image feature is determined according to the first medical image data and the first image weight matrix, the first image feature is able to represent the correlation information between each two first medical images in the first medical image data. In addition, the first image feature obtained through the first feature extraction network may accurately represent the first medical image data. On this basis, the first gene mutation information is obtained according to the first image feature, thereby achieving a combination of image data feature extraction and gene mutation information testing, so that comprehensiveness and accuracy of the gene mutation detection may be improved.

The method 200 of processing the medical data according to embodiments of the present disclosure will be further described below with reference to FIG. 3A, FIG. 3B, FIG. 4A, FIG. 4B, FIG. 5A, FIG. 5B, FIG. 5C and FIG. 6.

According to embodiments of the present disclosure, a plurality of kinds of mono-modality medical image data include at least one selected from: mono-modality medical image data corresponding to an anatomical structure, mono-modality medical image data corresponding to a lesion site, mono-modality medical image data corresponding to an edema region, or mono-modality medical image data corresponding to a contrast enhancement.

According to embodiments of the present disclosure, operation S220 may include the following operations. The plurality of kinds of mono-modality medical image data are input into a plurality of first feature extraction sub-networks respectively corresponding to the plurality of mono-modality medical image data, so as to obtain a plurality of mono-modality image features.

According to embodiments of the present disclosure, operation S230 may include the following operations. Feature concatenation are performed on the plurality of mono-modality image features to obtain a concatenated image feature. The concatenated image feature is input into a first classification network to obtain the first gene mutation information.

According to embodiments of the present disclosure, the first medical image data may include a plurality of kinds of mono-modality medical image data. The first feature extraction network may include a plurality of first feature extraction sub-networks respectively corresponding to the plurality of kinds of mono-modality medical image data.

According to embodiments of the present disclosure, the plurality of first feature extraction sub-networks may be used to extract their respective mono-modality medical image data. For example, the plurality of kinds of mono-modality medical image data may include mono-modality medical image data 1, mono-modality medical image data 2, . . . , mono-modality medical image data m, . . . , and mono-modality medical image data M. The plurality of first feature extraction sub-networks may include a first feature extraction sub-network 1, a first feature extraction sub-network 2, . . . , a first feature extraction sub-network m, . . . , and a first feature extraction sub-network M. M may be an integer greater than or equal to 1, and $m \in \{1, 2, \ldots, (M-1), M\}$.

In this case, the mono-modality medical image data 1 may be processed using the first feature extraction sub-network 1 to obtain a mono-modality image feature 1, the mono-modality medical image data 2 may be processed using the first feature extraction sub-network 2 to obtain a mono-modality image feature 2, the mono-modality medical image data m may be processed using the first feature extraction sub-network m to a obtain mono-modality image feature m, and the mono-modality medical image data M may be processed using the first feature extraction sub-network M to obtain a mono-modality image feature M. Feature concatenation may be performed on the mono-modality image feature 1, the mono-modality image feature 2, . . . , the mono-modality image feature m, . . . , and the mono-modality image feature M, so as to obtain a concatenated image feature.

According to embodiments of the present disclosure, after the concatenated image feature is obtained, the concatenated image feature may be processed using a first classification network to obtain the first gene mutation information. The first classification network may include a second deep learning model that may achieve classification. The first classification network may be obtained by training the second deep learning model using a sample concatenated image feature. A model structure of the second deep learning model may be determined according to actual service needs and is not limited here. For example, the second deep learning model may include at least one selected from: a second deep learning model based on convolutional neural network, a second deep learning model based on recurrent neural network, a second deep learning model based on deep belief network (DBN), or a second deep learning model based on Restricted Boltzmann Machine (RBM).

According to embodiments of the present disclosure, the first medical image data includes the plurality of kinds of mono-modality medical image data, and the plurality of mono-modality image features are obtained by processing the plurality of mono-modality medical image data using the plurality of corresponding first feature extraction sub-networks. On this basis, the concatenated image feature is obtained by performing the feature concatenation on the plurality of mono-modality image features, so that the comprehensiveness of the first gene mutation information may be ensured.

Figure 3A:
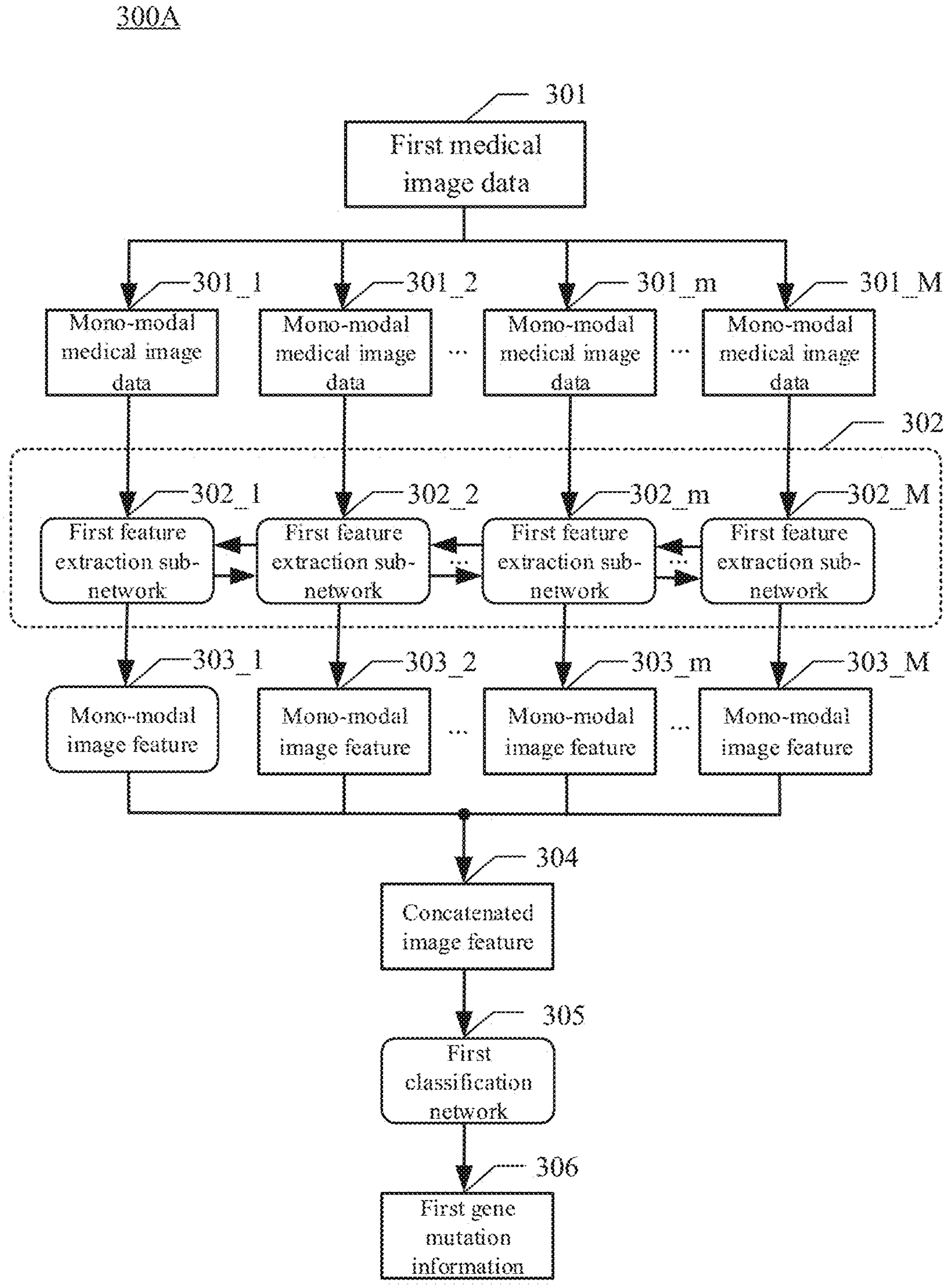
FIG. 3A schematically shows a schematic diagram of an example of obtaining a first gene mutation information based on a first image feature according to an embodiment of the present disclosure.

FIG. 3A schematically shows a schematic diagram of an example of obtaining a first gene mutation information based on a first image feature according to an embodiment of the present disclosure.

As shown in FIG. 3A, the first medical image data 301 may include a plurality of kinds of mono-modality medical image data. The plurality of mono-modality medical image data may include mono-modality medical image data 301_1, mono-modality medical image data 301_2, . . . , mono-modality medical image data 301_*m*, . . . , mono-modality medical image data 301_M. M may be an integer greater than or equal to 1, and m E {1, 2, . . . , (M−1), M}.

The first feature extraction network 302 may include a plurality of first feature extraction sub-networks respectively corresponding to the plurality of kinds of mono-modality medical image data. The first feature extraction sub-network may include a first feature extraction sub-network 302_1, a first feature extraction sub-network 302_2, . . . , a first feature extraction sub-network 302_*m*, . . . , a first feature extraction sub-network 302_M.

The mono-modality medical image data 301_1 may be processed using the first feature extraction sub-network 302_1 to obtain a mono-modality image feature 303_1, the mono-modality medical image data 301_2 may be processed using the first feature extraction sub-network 302_2 to obtain a mono-modality image feature 3032, the mono-modality medical image data 301_*m* may be processed using the first feature extraction sub-network 302_*m* to obtain a mono-modality image feature 303_*m*, and the mono-modality medical image data 301_M may be processed using the first feature extraction sub-network 302_M to obtain a mono-modality image feature 303_M.

After the mono-modality image feature 303_1, the mono-modality image feature 303_2, . . . , the mono-modality image feature 303_*m*, . . . , the mono-modality image feature 303_M are obtained, a feature concatenation may be performed to obtain a concatenated image feature 304. The concatenated image feature 304 may be processed using a first classification network 305, so as to obtain a first gene mutation information 306.

According to embodiments of the present disclosure, operation S220 may also include the following operations. Multi-modality medical image data is input into the plurality of first feature extraction sub-networks to obtain a plurality of multi-modality image features.

According to embodiments of the present disclosure, operation S230 may also include the following operations. The plurality of multi-modality image features are input into a second classification network to obtain a plurality of predictions for single gene mutation types. The plurality of predictions for single gene mutation types is combined to obtain the first gene mutation information.

According to embodiments of the present disclosure, the first medical image data may include multi-modality medical image data. The first feature extraction network may include a plurality of first feature extraction sub-networks.

According to embodiments of the present disclosure, the plurality of first feature extraction sub-networks may be used to extract their respective multi-modality medical image data. For example, data of a plurality of multi-modality medical images may include multi-modality medical image data 1, multi-modality medical image data 2, . . . , multi-modality medical image data n, . . . , and multi-modality medical image data N. The plurality of first feature extraction sub-networks may include a first feature extraction sub-network 1, a first feature extraction sub-network 2, . . . , a first feature extraction sub-network n, . . . , and a first feature extraction sub-network N. N may be an integer greater than or equal to 1, and n E {1, 2, . . . , (N−1), N}.

In this case, the multi-modality medical image data 1 may be processed using the first feature extraction sub-network 1 to obtain a multi-modality image feature 1, the multi-modality medical image data 2 may be processed using the first feature extraction sub-network 2 to obtain a multi-modality image feature 2, the multi-modality medical image data n may be processed using the first feature extraction sub-network n to obtain a multi-modality image feature n, and the multi-modality medical image data N may be processed using the first feature extraction sub-network N to obtain a multi-modality image feature N.

According to embodiments of the present disclosure, after the multi-modality image feature 1, the multi-modality image feature 2, . . . , the multi-modality image feature n, . . . , and the multi-modality image feature N are obtained, the plurality of multi-modality image features may be respectively processed using the second classification network, so as to obtain a plurality of predictions for single gene mutation types. The second classification network may include a third deep learning model that may achieve classification. The second classification network may be obtained by training the third deep learning model using a sample multi-modality image feature. A model structure of the third deep learning model may be determined according to actual service needs and is not limited here. For example, the third deep learning model may include at least one selected from: a third deep learning model based on convolutional neural network, a third deep learning model based on recurrent neural network, a third deep learning model based on Deep Belief Network, or a third deep learning model based on Restricted Boltzmann Machine.

According to embodiments of the present disclosure, the second classification network may include a plurality of second classification sub-networks respectively corresponding to the plurality of multi-modality image features.

According to embodiments of the present disclosure, inputting the plurality of multi-modality image features into the second classification network to obtain the plurality of predictions for single gene mutation types may include the following operations. The plurality of multi-modality image features are input into the second classification sub-networks respectively corresponding to the plurality of multi-modality image features, so as to obtain the plurality of predictions for single gene mutation types.

According to embodiments of the present disclosure, the plurality of second classification sub-networks may be respectively used to classify their respective multi-modality image features. The plurality of second classification sub-networks may include a second classification sub-network 1, a second classification sub-network 2, . . . , a second classification sub-network n, . . . , and a second classification sub-network N. N may be an integer greater than or equal to 1, and $n \in \{1, 2, \ldots, (N-1), N\}$.

In this case, the multi-modality image feature 1 may be processed using the second classification sub-network 1 to obtain a single gene mutation type prediction 1, the multi-modality image feature 2 may be processed using the second classification sub-network 2 to obtain a single gene mutation type prediction 2, the multi-modality image feature n may be processed using the second classification sub-network n to obtain a single gene mutation type prediction n, and the multi-modality image feature N may be processed using the second classification sub-network N to obtain a single gene mutation type prediction N.

According to embodiments of the present disclosure, after the single gene mutation type prediction 1, the single gene mutation type prediction 2, . . . , the single gene mutation type prediction n, . . . , and the single gene mutation type prediction information N are obtained, they plurality of predictions for single gene mutation types may be combined using a fourth deep learning model, so as to obtain the first gene mutation information. The fourth deep learning model may include a deep learning model that may achieve an information combination. The fourth deep learning model may be obtained by training the deep learning model using a sample single gene mutation type prediction. A model structure of the fourth deep learning model may be determined according to actual service needs and is not limited here.

According to embodiments of the present disclosure, the second classification sub-network may include at least one of an isocitrate dehydrogenase mutation classification network, a chromosome 1p/19q classification network, a telomerase reverse transcriptase promoter classification network, or an $O^6$-methylguanine-DNA methyltransferase classification network.

According to embodiments of the present disclosure, isocitrate dehydrogenase is an important protein existing in glycometabolism, which catalyzes an oxidative decarboxylation of isocitrate to α-ketoglutarate (i.e., α-KG). Reduced Nicotinamide Adenine Dinucleotide Phosphate (NADPH) or NADH is produced during the above process. α-KG is a substrate for various dioxygenases that control histone modifications, and plays an important role in regulating a glutamate production and a cellular reaction to oxidation and energy stress. IDH mutation may lead to an abnormal production and accumulation of D-2-hydroxyglutarate (D-2-HG), resulting in changes in cellular energy and methylation groups. The isocitrate dehydrogenase mutation classification network may be used to classify a multi-modality image feature related to isocitrate dehydrogenase mutation, so as to obtain an isocitrate dehydrogenase gene mutation type prediction information. The isocitrate dehydrogenase gene mutation type prediction information may include a prediction result of IDH mutant-type or a prediction result of IDH wild-type.

According to embodiments of the present disclosure, the chromosome 1p/19q co-deletion may refer to simultaneous deletion of short arm of chromosome 1 and long arm of chromosome 19. The chromosome 1p/19q co-deletion is highly related to oligodendroglioma and is a molecular marker of the oligodendroglioma. The chromosome 1p/19q co-deletion is related to IDH gene mutation, which means that the IDH gene mutation occurs in a case of chromosome 1p/19q co-deletion. The chromosome 1p/19q classification network may be used to classify a multi-modality image feature related to chromosome 1p/19q mutation, so as to obtain a chromosome 1p/19q gene mutation type prediction information. The chromosome 1p/19q gene mutation type prediction information may include a prediction result of co-deletion of chromosome 1p/19q and a prediction result of no co-deletion of target chromosome 1p/19q.

According to embodiments of the present disclosure, telomerase is a ribonucleoprotein polymerase with reverse transcription activity. The activity of telomerase may depend on a transcriptional regulation of TERT with catalytic activity. The activity of telomerase is positively correlated with an expression of TERT. TERT promoter mutation may lead to telomerase activation, resulting in a cell immortalization. The telomerase reverse transcriptase promoter classification network may be used to classify a multi-modality image feature related to telomerase reverse transcriptase mutation, so as to obtain a telomerase reverse transcriptase gene mutation type prediction information. The telomerase reverse transcriptase gene mutation type prediction information may include one of a prediction result of telomerase reverse transcriptase mutant-type or a prediction result of telomerase reverse transcriptase wild-type.

According to embodiments of the present disclosure, MGMT may be a DNA repair protein, which may be used to remove an alkyl adduct mutagenic at $O^6$ site of guanine on DNA to restore the damaged guanine, and thus protect the cell immunity from the damage of alkylating agents. A CpG site in a normal tissue is in a non-methylation state, and the MGMT promoter methylation may cause an MGMT expression deletion, resulting in a decrease in MGMT content and hindered DNA repair in cells. The MGMT promoter methylation may be one of mechanisms underlying the occurrence and development of brain glioma. The $O^6$-methylguanine-DNA methyltransferase classification network may be used to classify a multi-modality image feature related to $O^6$-methylguanine-DNA methyltransferase mutation, so as to obtain an $O^6$-methylguanine-DNA methyltransferase mutation type prediction information. The $O^6$-methylguanine-DNA methyltransferase mutation type prediction information may include a prediction result of methylation of $O^6$-methylguanine-DNA methyltransferase promoter and a prediction result of no methylation of $O^6$-methylguanine-DNA methyltransferase promoter.

According to embodiments of the present disclosure, based on the first medical image data including the plurality of kinds of mono-modality medical image data or the multi-modality medical image data, a high-precision multi-gene mutation testing may be achieved for IDH mutation, chromosome 1p/19q co-deletion, TERT mutation and MGMT promoter methylation.

According to embodiments of the present disclosure, the plurality of first feature extraction sub-networks may share model parameters with each other.

According to embodiments of the present disclosure, in the case that the plurality of first feature extraction sub-networks are used to extract their respective corresponding mono-modality medical image data, the plurality of first feature extraction sub-networks may share model parameters with each other. In the case that the plurality of first feature extraction sub-networks are used to extract their respective corresponding multi-modality medical image data, the plurality of first feature extraction sub-networks may share model parameters with each other.

According to embodiments of the present disclosure, the first medical image data includes the multi-modality medical image data, and the plurality of multi-modality image features are obtained by processing the multi-modality medical image data using the plurality of corresponding first feature extraction sub-networks. On this basis, the plurality of predictions for single gene mutation types is obtained by processing the plurality of multi-modality image features using the second classification network, so that the comprehensiveness of the first gene mutation information may be ensured.

Figure 3B:
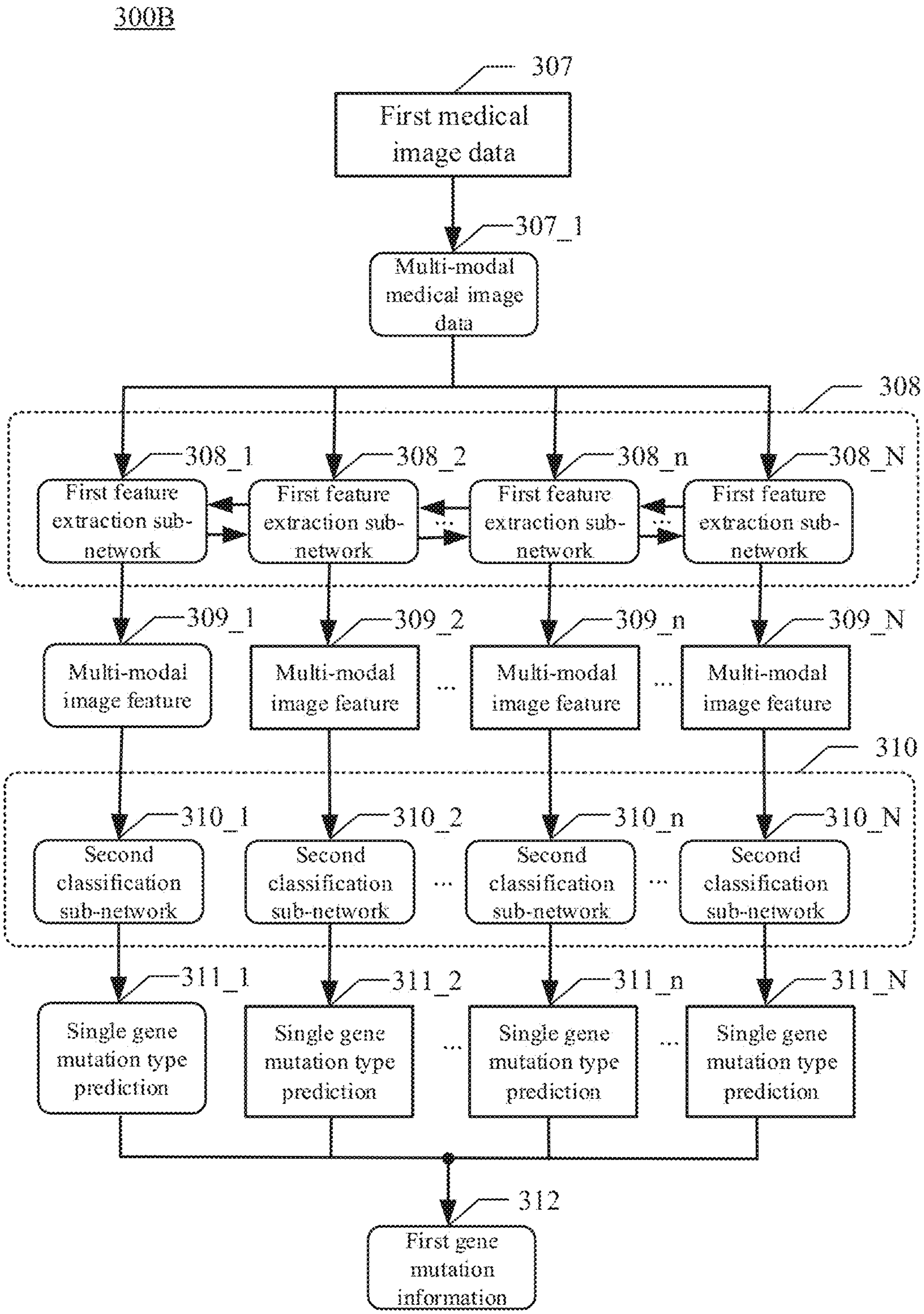
FIG. 3B schematically shows a schematic diagram of an example of obtaining a first gene mutation information based on a first image feature according to another embodiment of the present disclosure.

FIG. 3B schematically shows a schematic diagram of an example of obtaining a first gene mutation information based on a first image feature according to another embodiment of the present disclosure.

As shown in FIG. 3B, the first medical image data 307 may include multi-modality medical image data 307_1. The first feature extraction network 308 includes a plurality of first feature extraction sub-networks. The plurality of first feature extraction sub-networks may include a first feature extraction sub-network 308_1, a first feature extraction sub-network 308_2, . . . , a first feature extraction sub-network 308_*n*, . . . , a first feature extraction sub-network 308_N. N may be an integer greater than or equal to 1, and $n \in \{1, 2, \ldots, (N-1), N\}$.

The multi-modality medical image data 307_1 may be processed using the first feature extraction sub-network 308_1 to obtain a multi-modality image feature 309_1, the multi-modality medical image data 307_1 may be processed using the first feature extraction sub-network 308_2 to obtain a multi-modality image feature 309_2, the multi-modality medical image data 3071 may be processed using the first feature extraction sub-network 308_*n* to obtain a multi-modality image feature 309_*n*, and the multi-modality medical image data 3071 may be processed using the first feature extraction sub-network 308_N to obtain a multi-modality image feature 309_N.

After the multi-modality image feature 309_1, the multi-modality image feature 309_2, . . . , the multi-modality image feature 309_*n*, . . . , the multi-modality image feature 309_N are obtained, the plurality of multi-modality image features may be input into a second classification network 310 to obtain a plurality of predictions for single gene mutation types. The second classification network 310 may include a second classification sub-network 310_1, a second classification sub-network 310_2, . . . , a second classification sub-network 310_*n*, . . . , and a second classification sub-network 310_N.

The multi-modality image feature 3091 may be processed using the second classification sub-network 310_1 to obtain a single gene mutation type prediction information 311_1. The multi-modality image feature 309_2 may be processed using the second classification sub-network 310_2 to obtain a single gene mutation type prediction 311_2. The multi-modality image feature 309_*n* may be processed using the second classification sub-network 310_*n* to obtain a single gene mutation type prediction 311_*n*. The multi-modality image feature 309_N may be processed using the second classification sub-network 310_N to obtain a single gene mutation type prediction 311_N.

After the single gene mutation type prediction 311_1, the single gene mutation type prediction 311_2, . . . , the single gene mutation type prediction 311_*n*, . . . and the single gene mutation type prediction 311_N are obtained, a first gene mutation information 312 may be determined.

According to embodiments of the present disclosure, the method 200 of processing the medical data may further include the following operations.

The plurality of first medical images are input into a second feature extraction module to obtain a first temporal image feature. The first temporal image feature represents a temporal relationship between the plurality of first medical images.

According to embodiments of the present disclosure, determining the first image query matrix and the first image key matrix according to the first medical image data may include the following operations.

The first temporal image feature is input into the first feature extraction module to obtain the first image query matrix and the first image key matrix.

According to embodiments of the present disclosure, the first medical image data may include a plurality of first medical images, and the first feature extraction network may further include a second feature extraction module. The plurality of first medical images may be processed using the second feature extraction module to obtain the first temporal image feature. A model structure of the second feature extraction module may be determined according to actual service needs and is not limited here. For example, the second feature extraction module may include at least one of LSTM (Long Short-Term Memory) or Bi-LSTM (Bi-directional Long Short-Term Memory). Bi-LSTM may include forward LSTM and backward LSTM.

According to embodiments of the present disclosure, Bi-LSTM is taken as an example of the second feature extraction module, which is an LSTM with 128 units in two layers. An output of a first layer of LSTM may be used as an input of a second layer of LSTM. In a case of X first medical images, the X first medical images may be sorted by scan number. After the first medical images are processed by the third feature extraction module, a tensor of X×512 may be output. The tensor of X×512 may be processed using the Bi-LSTM, and it is possible to obtain bi-directional feature codes of each first medical image by using the forward LSTM and the backward LSTM in the Bi-LSTM. The feature codes output by the forward LSTM and the backward LSTM may be concatenated to obtain a tensor of X×256. The tensor of X×256 may be used as the first temporal image feature to represent the temporal relationship between the plurality of first medical images.

According to embodiments of the present disclosure, after the first temporal image feature is obtained, the first temporal image feature output by the second feature extraction module may be used as an input of the first feature extraction module. In this case, the first temporal image feature may be processed using the first feature extraction module to obtain the first image query matrix and the first image key matrix. A calculation method of the first feature extraction module may be shown below as Equation (1) to Equation (3).

$$\alpha_{a,b} = \mathrm{softmax}(h_a, h_b)) = \frac{\exp(\mathrm{score}(h_a, h_b))}{\sum_a \mathrm{score}(f(h_a, h_b))} \quad (1)$$

-continued $$\mathrm{score}(h_a,\ h_b) = \frac{h_a^T h_b}{\sqrt{d}} \quad (2)$$

$$s_b = \sum_a \alpha_{a,b} h_b \quad (3)$$

where $a_{a,b}$ may represent the first image weight matrix, $h_a$ may represent the first image query matrix, $h_b$ may represent the first image key matrix, score( ) may represent a scoring function for scaled dot-product attention, d may represent a dimension size of the first image key matrix, and $s_b$ may represent the first image feature.

Figure 4A:
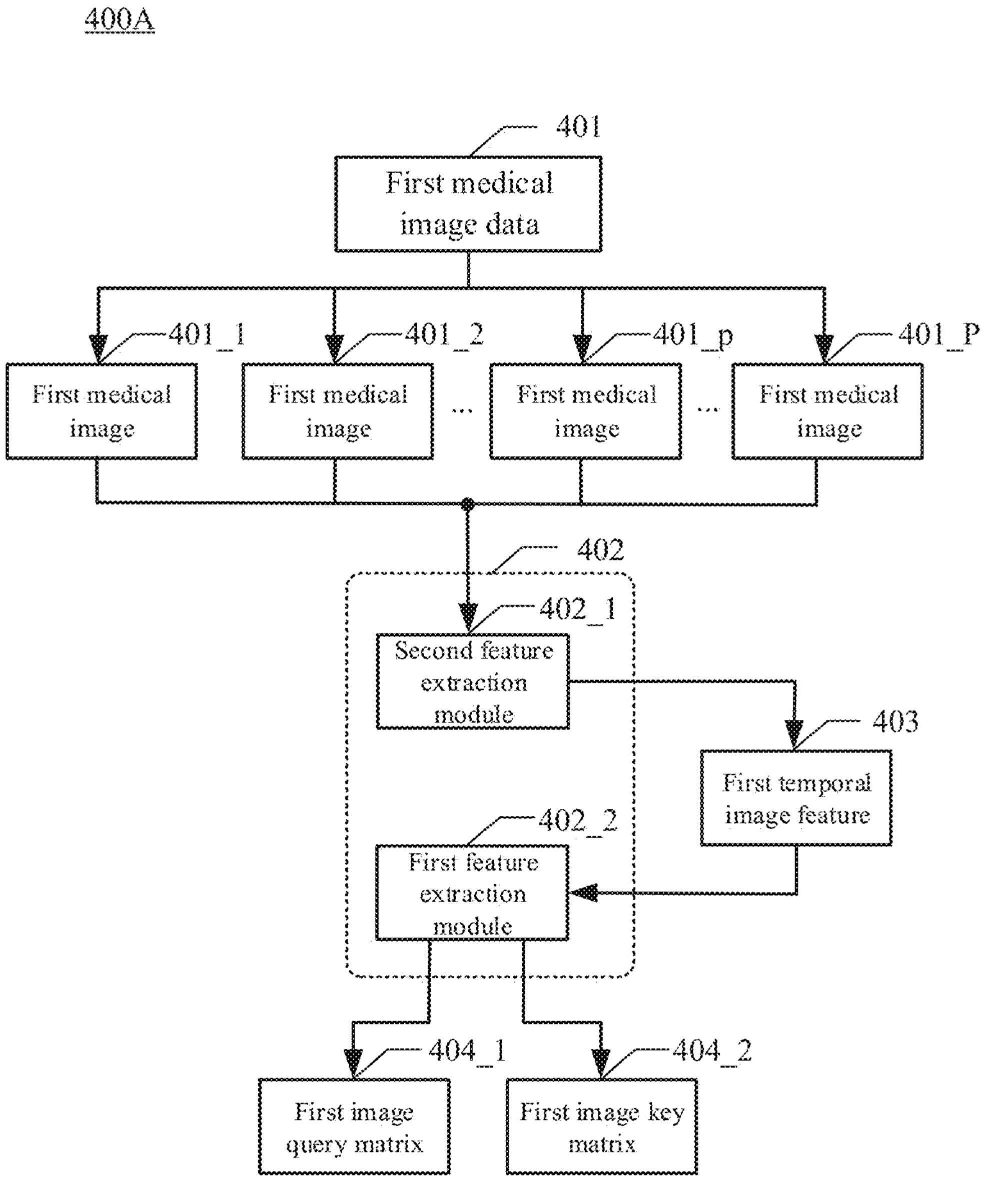
FIG. 4A schematically shows a schematic diagram of an example of determining a first image query matrix and a first image key matrix based on first medical image data according to an embodiment of the present disclosure.

FIG. 4A schematically shows a schematic diagram of an example of determining a first image query matrix and a first image key matrix based on a first medical image data according to an embodiment of the present disclosure.

As shown in FIG. 4A, first medical image data 401 may include a plurality of first medical images. The plurality of first medical images may include a first medical image 401_1, a first medical image 401_2, . . . , a first medical image 401_*p*, . . . , a first medical image 401_P. where P may be an integer greater than or equal to 1, and $p \in \{1, 2, \ldots, (P-1), P\}$.

The first feature extraction network 402 may include a second feature extraction module 402_1 and a first feature extraction module 402_2. The plurality of first medical images may be processed using the second feature extraction module 402_1 to obtain a first temporal image feature 403.

After the first temporal image feature 403 is obtained, the first temporal image feature 403 may be processed using the first feature extraction module 402_2 to obtain a first image query matrix 404_1 and a first image key matrix 404_2.

According to embodiments of the present disclosure, the first feature extraction network may further include a third feature extraction module.

According to embodiments of the present disclosure, the method 200 of processing the medical data may further include the following operations.

The plurality of first medical images are input into the third feature extraction module to obtain a plurality of first intermediate image features.

According to embodiments of the present disclosure, inputting the plurality of first medical images into the second feature extraction module to obtain the first temporal image feature may include the following operations.

The plurality of first intermediate image features are input into the second feature extraction module to obtain the first temporal image feature.

According to embodiments of the present disclosure, the third feature extraction module may be used to acquire the first intermediate image feature. A model structure of the third feature extraction module may be determined according to actual service needs and is not limited here. For example, the third feature extraction module may include a feature extraction structure based on encoder-decoder and a feature extraction structure based on fully convolutional neural network. The feature extraction structure based on encoder-decoder may include at least one of a feature extraction structure based on Transformer and a deep learning model based on convolutional neural network. The encoder-decoder may include a symmetric encoder-decoder and an asymmetric encoder-decoder. Model architecture of the feature extraction structure based on Transformer and model architecture of the deep learning model based on fully convolutional neural network may include U-shaped model architecture and V-shaped model architecture. For example, the U-shaped model architecture may include at least one of U-Net, D-LinkNet or MDU-Net (i.e., Multi-scale Densely Connected U-Net).

According to embodiments of the present disclosure, the third feature extraction module may include a first maximum pooling layer, a first residual unit, a first down-sampling unit, and a first average pooling layer.

According to embodiments of the present disclosure, a feature extraction may be performed on the plurality of first medical images respectively using the third feature extraction module, so as to obtain a plurality of first intermediate image features. For example, the third feature extraction module may include a down-sampling module and an up-sampling module. The plurality of first medical images may be processed using the down-sampling module of the third feature extraction module to obtain a plurality of first intermediate image features. The down-sampling module may include a first convolutional neural network or a Transformer-based encoder. Transformer may include a visual Transformer. The visual transformer may include at least one of Vision Transformer and Swin Transformer. The first convolutional neural network may include at least one of ResNet (Residual Neural Network), VGGNet (Visual Geometry Group Network), WideResNet (Wide Residual Network), or DenseNet (Dense Neural Network).

According to embodiments of the present disclosure, the down-sampling module may include at least one cascaded down-sampling unit. The down-sampling unit may include a first maximum pooling layer, a first residual unit, a first down-sampling unit, and a first average pooling layer. The first down-sampling unit may include at least one first convolutional layer. The first maximum pooling layer may include at least one pooling layer. The first medical image sequentially passes through the at least one cascaded down-sampling unit, and a feature map with a reduced size corresponding to the image feature data may be obtained each time the medical image passes through a down-sampling unit. The down-sampling unit may be used to perform down-sampling on the image feature data which is in a scale corresponding to the feature extraction unit.

According to embodiments of the present disclosure, a rectified linear unit (i.e., ReLU) may be used as an activation function of a hidden state. By using the ReLU activation function, an information transmission may be performed more directly, and a gradient vanishing problem caused by using a Tanh activation function may be avoided.

According to embodiments of the present disclosure, the first feature extraction network may include a third feature extraction module and a first feature extraction module. The plurality of first medical images may be input into the third feature extraction module to obtain a plurality of first intermediate image features. A first image query matrix and a first image key matrix may be determined according to the plurality of first intermediate image features. A first image weight matrix may be determined according to the first image query matrix and the first image key matrix. The first image weight matrix represents a correlation information between each two first medical images in the first medical image data. The first image feature may be determined according to the first image weight matrix and the first medical image data.

According to embodiments of the present disclosure, the first maximum pooling layer may include a first convolutional layer, a first regularization layer, a first activation function layer and a maximum pooling layer that are connected in cascade. The first residual unit may include a second convolutional layer, a second regularization layer, a second activation function layer, a third convolutional layer and a third regularization layer that are connected in cascade. The first down-sampling unit may include a fourth convolutional layer, a fourth regularization layer, a third activation function layer, a fifth convolutional layer, a fifth regularization layer, a sixth convolutional layer and a sixth regularization layer that are connected in cascade. The first average pooling layer may be used to convert the processed image feature into the first image feature.

According to embodiments of the present disclosure, the third feature extraction module may include one first maximum pooling layer, three first residual units, one first down-sampling unit, three first residual units, one first down-sampling unit, five first residual units, one first down-sampling unit, two first residual units and one first average pooling layer that are connected in cascade.

According to embodiments of the present disclosure, the first convolutional layer may include a 7*7 convolutional kernel with a stride of 2. The maximum pooling layer may include a 3*3 convolutional kernel with a stride of 2. The second convolutional layer, the third convolutional layer and the fifth convolutional layer may include 3*3 convolutional kernels with a stride of 1. The fourth convolutional layer may include a 3*3 convolutional kernel with a stride of 2. The sixth convolution may include a 1*1 convolution kernel with a stride of 2.

According to embodiments of the present disclosure, the first maximum pooling layer may be used to process first medical image data of 256*256 by using a 7*7 convolution kernel with a stride of 2 and a 3*3 convolution kernel with a stride of 2, so as to obtain a 64*64 feature map. The first residual unit may be used to process the 64*64 feature map output by the first maximum pooling layer by using two 3*3 convolution kernels with a stride of 1, so as to obtain a 128*128 feature map. The first down-sampling unit may be used to process the 128*128 feature map output by the first down-sampling unit by using a 3*3 convolution kernel with a stride of 2, a 3*3 convolution kernel with a stride of 1 and one 1*1 convolution kernel with a stride of 2, so as to obtain a 128*128 feature map. The first average pooling layer may be used to convert the image feature processed by the first down-sampling unit into a first image feature of 1*512.

According to embodiments of the present disclosure, since the first intermediate image feature is obtained by processing the first medical image using the third feature extraction module, a data dimension of the first medical image may be reduced, and a storage space occupation may be reduced, so that a problem of gradient diffusion or gradient explosion in the neural network may be avoided. In addition, since the first temporal image feature is obtained by processing the first intermediate image feature using the second feature extraction module, the temporal feature of the plurality of first medical images may be obtained.

According to embodiments of the present disclosure, determining the first image feature according to the first image weight matrix and the first medical image data may include the following operations.

A first image value matrix is obtained according to the first medical image data. The first image feature is obtained according to the first image weight matrix and the first image value matrix.

According to embodiments of the present disclosure, the first image query matrix and the first image key matrix may be determined according to the first medical image data. For example, the first image query matrix may be determined according to the first medical image data and a query parameter matrix, and the first image key matrix may be determined according to the first medical image data and a key parameter matrix. After the first image query matrix and the first image key matrix are determined, the first image weight matrix indicating the correlation information between each two first medical images in the first medical image data may be determined.

According to embodiments of the present disclosure, the first image value matrix may be determined according to the first medical image data. For example, the first image value matrix may be determined according to the first medical image data and a value parameter matrix. After the first image value matrix is determined, the first image feature may be determined according to the first image weight matrix and the first image value matrix.

Figure 4B:
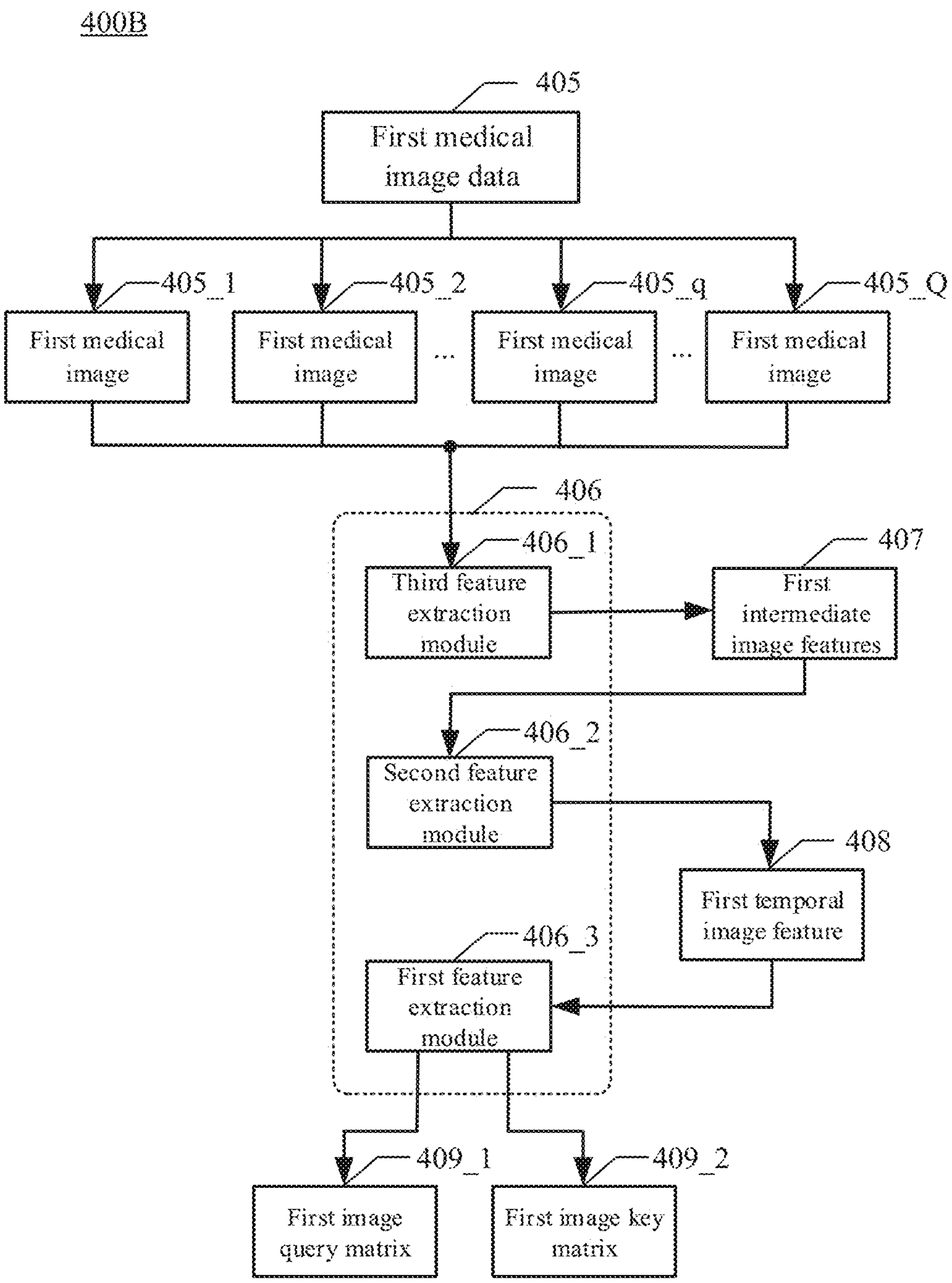
FIG. 4B schematically shows a schematic diagram of an example of determining a first image query matrix and a first image key matrix based on first medical image data according to another embodiment of the present disclosure.

FIG. 4B schematically shows a schematic diagram of an example of determining a first image query matrix and a first image key matrix based on first medical image data according to another embodiment of the present disclosure.

As shown in FIG. 4B, first medical image data 405 may include a plurality of first medical images. The plurality of first medical images may include a first medical image 405_1, a first medical image 405_2, . . . , a first medical image 405_*q*, . . . , a first medical image 405_Q. Q may be an integer greater than or equal to 1, and $q \in \{1, 2, \ldots, (Q-1), Q\}$.

A first feature extraction network 406 may include a third feature extraction module 406_1, a second feature extraction module 4062, and a first feature extraction module 406_3. The plurality of first medical images may be processed using the third feature extraction module 406_1 to obtain a plurality of first intermediate image features 407.

After the plurality of first intermediate image features 407 are obtained, the plurality of first intermediate image features 407 may be processed using the second feature extraction module 406_2 to obtain a first temporal image feature 408.

After the first temporal image feature 408 is obtained, the first temporal image feature 408 may be processed using the first feature extraction module 406_3 to obtain a first image query matrix 409_1 and a first image key matrix 409_2.

According to embodiments of the present disclosure, the method 200 of processing the medical data may further include the following operations.

Medical image metadata is obtained according to the first medical image data.

According to embodiments of the present disclosure, an original medical image corresponding to the first medical image data is a gray-scale image in DICOM (Digital Imaging and Communications in Medicine) format. Image-related metadata may be stored in image data in DICOM format. The medical image metadata may be obtained by reading any 2D slice in DICOM format from the first medical image data using Pydicom. For example, the image-related metadata may include at least one selected from slice thickness, pixel spacing, device manufacturer, device model, repetition time, echo time, etc.

According to embodiments of the present disclosure, the first medical image data may include first medical image data not containing label information and first medical image data containing label information. A label of the first medical image data may include at least one selected from: a T1 modality label, a T2 modality label, a TICE modality label, or a FLAIR modality label. The first medical image data not containing label information may be used to train an image feature extraction network in a medical image data contrastive learning network. The first medical image data containing label information may be used to train a first classification network in the medical image data contrastive learning network.

According to embodiments of the present disclosure, the medical image metadata may include medical image metadata not containing label information and medical image metadata containing label information. The medical image metadata not containing label information may be used to train a metadata feature extraction network in a medical image metadata contrastive learning network. The medical image metadata containing label information may be used to train a second classification network in the medical image metadata contrastive learning network.

According to embodiments of the present disclosure, after the original medical image is obtained, a medical data preprocessing operation may be performed on the original medical image to obtain the first medical image data. The preprocessing of medical data may include at least one selected from: re-sampling, data standardization, bias field correction, affine transformation, image scaling, image selection, or data enhancement. The data standardization may include zero-mean standardization and standard-deviation standardization.

According to embodiments of the present disclosure, re-sampling may be performed on the original medical image to obtain the first medical image data. In a case of a plurality of first medical image data, volume pixels of the plurality of first medical image data represent a consistent actual physical space. In addition, a data standardization may be performed on the original medical image to obtain the first medical image data.

According to embodiments of the present disclosure, the original medical image may include a medical image in at least one modality. A data standardization may be performed on the original medical image to obtain the first medical image data. Alternatively, an image clipping may be performed the original medical image to obtain a first intermediate medical image. Re-sampling may be performed on the first intermediate medical image to obtain a second intermediate medical image. A data standardization may be performed on the second intermediate medical image to obtain the first medical image data.

According to embodiments of the present disclosure, bias field correction may be performed on the original medical image to obtain the first medical image data. For example, the bias field correction may be performed on the original medical image using N4BiasCorrection in SimpleTk, so as to eliminate a radio frequency non-uniformity.

According to embodiments of the present disclosure, an affine transformation may be performed on the original medical image to obtain the first medical image data. For example, it is possible to register an image in a particular modality to a template image corresponding to the modality (e.g., T1 image with Case of TCGA-CS-4938 in TCIA-LGG) by using ANTS software, and then register other modalities to the newly registered image, so as to complete the affine transformation of the original medical image. Alternatively, image scaling may be performed on the original medical image, for example, a size of the original medical image may be adjusted to 256*256 by using a bilinear interpolation algorithm.

According to embodiments of the present disclosure, an image selection may be performed on the original medical image. For example, it is possible to sort the images in an ascending order of scan numbers and remove images with zero image matrix values to obtain the first medical image data. Alternatively, a data enhancement may be performed on the original medical image to increase the number of medical images. For example, an image rotation method may be used to rotate the original medical image every 90 degrees to obtain the first medical image data.

According to embodiments of the present disclosure, after the first medical image data is obtained, original medical image metadata may be determined according to the first medical image data. A metadata preprocessing operation may be performed on the original medical image metadata to obtain the medical image metadata. The metadata preprocessing may include at least one of discretization, normalization, or vectorization.

According to embodiments of the present disclosure, discretization may be performed on the original medical image metadata to obtain the medical image metadata. In this case, the device manufacturer and the device model in the medical image metadata may be represented by discrete numerical values. Alternatively, normalization may be performed on the original medical image metadata to obtain the medical image metadata. In this case, the repetition time and the echo time in the medical image metadata may be represented by normalized values. Alternatively, vectorization may be performed on the original medical image metadata to obtain the medical image metadata. In this case, the medical image metadata may indicate a sequence relationship between a plurality of original medical images.

According to embodiments of the present disclosure, discretization may be performed on the original medical image metadata to obtain second intermediate medical image metadata. Normalization may be performed on the second intermediate medical image metadata to obtain third intermediate medical image metadata. Vectorization may be performed on the third intermediate medical image metadata to obtain the medical image metadata.

According to embodiments of the present disclosure, the method 200 of processing the medical data may further include the following operations.

An image type information of the first medical image data is obtained according to device type conversion standard data of the first medical image data. According to embodiments of the present disclosure, the device type conversion standard data may include at least one of a device manufacturer and a device model of a medical image acquisition device. The image type information may refer to an image type of the first medical image data. For example, in a case that the first medical image data belongs to MRI image data, the image type may include at least one of a T1 modality, a T2 modality, a T1CE modality, or a FLAIR modality. Alternatively, in a case that the first medical image data belongs to CT image data, ECT image data, PET image data, ultrasound image data, OCT image data or X-ray image data, the image type may be determined according to actual service needs and is not limited here.

According to embodiments of the present disclosure, the device type conversion standard data corresponding to the first medical image data may be acquired, and the corresponding device type conversion standard data may be searched in a medical image data type conversion standard library. When the device type conversion standard data corresponding to the first medical image data is contained in the medical image data type conversion standard library, the image type information corresponding to the device type conversion standard data may be determined as the image type information of the first medical image data.

According to embodiments of the present disclosure, the method 200 of processing the medical data may further include the following operations.

In a case of failing to determine the image type information of the first medical image according to the device type conversion standard data corresponding to the first medical image data, the image type information may be determined according to the medical image metadata corresponding to the first medical image data. In a case of failing to determine the image type information according to the device type conversion standard data and failing to determine the image type information according to the medical image metadata, the image type information may be obtained according to the first medical image data and the medical image metadata.

According to embodiments of the present disclosure, in a case that the device type conversion standard data corresponding to the first medical image data is not contained in the medical image data type conversion standard library, the medical image metadata may be determined according to the first medical image data, and the corresponding device type conversion standard data may be searched in the metadata type conversion standard library. In a case that the device type conversion standard data corresponding to the medical image metadata is contained in the metadata type conversion standard library, the image type information corresponding to the device type conversion standard data may be determined as the image type information of the medical image metadata.

According to embodiments of the present disclosure, in a case of failing to determine the image type information according to the device type conversion standard data and failing to determine the image type information according to the medical image metadata, the first medical image data and the medical image metadata may be processed by a contrastive learning method to obtain the image type information. For example, the first medical image data may be input into a medical image data contrastive learning network to obtain a first image type information, and the medical image metadata may be input into a medical image metadata contrastive learning network to obtain a second image type information. The image type information may be obtained according to the first image type information and the second image type information.

According to embodiments of the present disclosure, the above-mentioned method of processing the medical data may further include the following operations.

A data enhancement is performed on the first medical image data. A data enhancement is performed on the medical image metadata.

According to embodiments of the present disclosure, performing the data enhancement on the first medical image data may include the following operations.

At least one of random clipping restoration, random color distortion or random Gaussian blur is performed on the first medical image data.

According to embodiments of the present disclosure, the first medical image data may be a medical image that includes at least one modality. A data enhancement may be performed on the first medical image data to obtain a data-enhanced first medical image data. The data enhancement may include at least one of random clipping restoration, random color distortion or random Gaussian blur.

According to embodiments of the present disclosure, random clipping restoration may be performed on the first medical image data to obtain a clipping-restored first medical image data. The clipping-restored first medical image data may have a same image resolution.

For example, according to a medical image in at least one modality included in the first medical image data, it is possible to determine a first bounding box corresponding to each of the at least one modality, so as to obtain at least one first bounding box. A union region of the at least one first bounding box may be determined to obtain a first target bounding box. Image clipping may be performed on the medical image in the at least one modality included in the first medical image data, so as to obtain the data-enhanced first medical image data.

For example, a pixel value of a region where the first target bounding box is located in the first medical image data may be determined as a first predetermined pixel value. A pixel value of a region other than the first target bounding box in the first medical image data may be determined as a second predetermined pixel value. The first predetermined pixel value and the second predetermined pixel value may be determined according to actual service needs and are not limited here. For example, the first predetermined pixel value may be 1, and the second predetermined pixel value may be 0.

According to embodiments of the present disclosure, a color distortion may be performed on the first medical image data to obtain a color-distorted first medical image data. For example, it is possible to adjust at least one parameter selected from color, brightness, contrast, saturation, or color tone. Alternatively, random Gaussian blur may be performed on the first medical image data to remove noise from the original medical image and obtain a Gaussian-blurred first medical image data.

According to embodiments of the present disclosure, the first medical image data may include 2Y images. Taking the first medical image data including 24 images as an example, the first medical image data may be randomly divided into 12 groups, with each group consisting of two medical images. Then, a data enhancement may be performed on two medical images in each group respectively according to the above-mentioned data enhancement operation.

According to embodiments of the present disclosure, performing the data enhancement on the second medical image data may include the following operations.

A synonym substitution is performed on the medical image metadata.

According to embodiments of the present disclosure, the synonyms substitution may be performed on the medical image metadata not containing label information in the medical image metadata, so as to obtain data-enhanced medical image metadata not containing label information. For example, the medical image metadata not containing label information may contain a sequence description "AXIAL". In this case, a synonym "AX" for "AXIAL" may be used to replace the "AXIAL" in the medical image metadata not containing label information. For example, the medical image metadata not containing label information may contain a sequence description "FSE". In this case, a synonym "SE" for "FSE" may be used to replace the "FSE" in the medical image metadata not containing label information.

According to embodiments of the present disclosure, obtaining the image type information according to the first medical image data and the medical image metadata may include the following operations.

The image type information is obtained according to the enhanced first medical image data and the enhanced first medical image metadata.

According to embodiments of the present disclosure, obtaining the image type information according to the enhanced first medical image data and the enhanced first medical image metadata may include the following operations.

The enhanced first medical image data and the enhanced medical image metadata are input into a contrastive learning network to obtain the image type information.

According to embodiments of the present disclosure, the contrastive learning network may include a feature extraction network and a classification network. The feature extraction network and the classification network may be trained for multiple rounds until a predetermined condition is met. The trained feature extraction network and the trained classification network are determined as the contrastive learning network. The enhanced first medical image data and the enhanced first medical image metadata may be processed using the feature extraction network to obtain representation vectors respectively corresponding to the enhanced first medical image data and the enhanced first medical image metadata. The representation vectors respectively corresponding to the enhanced first medical image data and the enhanced first medical image metadata may be processed using the classification network, so as to obtain the image type information.

According to embodiments of the present disclosure, the feature extraction network and the classification network may be determined according to actual service needs and are not limited here. For example, the feature extraction network may include a convolutional neural network. The convolutional neural network may include at least one of ResNet, VGGNet, WideResNet, or DenseNet. The classification network may include an artificial neural network (ANN) and a softmax normalization function. The artificial neural network may include at least one of a multilayer perceptron (MLP) and a back propagation (BP) neural network.

According to embodiments of the present disclosure, obtaining the image type information according to the first medical image data and the medical image metadata may include the following operations.

The first medical image data and the medical image metadata are input into the contrastive learning network to obtain the image type information. The contrastive learning network may include a medical image data contrastive learning network and a medical image metadata contrastive learning network.

According to embodiments of the present disclosure, inputting the first medical image data and the medical image metadata into the contrastive learning network to obtain the image type information may include the following operations.

The first medical image data is input into the medical image data contrastive learning network to obtain a first image type information. The medical image metadata is input into the medical image metadata contrastive learning network to obtain a second image type information. The image type information is obtained according to the first image type information and the second image type information.

According to embodiments of the present disclosure, in contrastive learning, a sub-sample obtained by performing a data enhancement on a parent sample may be used as a positive sample for the parent sample. The parent sample may refer to a sample that serves as an object on which the data enhancement is performed. In embodiments of the present disclosure, positive samples may include a parent sample and a positive sample obtained by performing a data enhancement on the parent sample. Negative samples may refer to other samples with different categories from the parent sample.

According to embodiments of the present disclosure, a self-supervised network may include at least one selected from: CPC (Comparative Predictive Coding), AMDIM (Augmented Multiscale Deep InfoMax), MOCO (Momentum Contrast), SimCLR (Simple Framework for Contrastive learning of Visual Representations), or BYOL (Bootstrap Your Own Latent), etc.

Figure 5A:
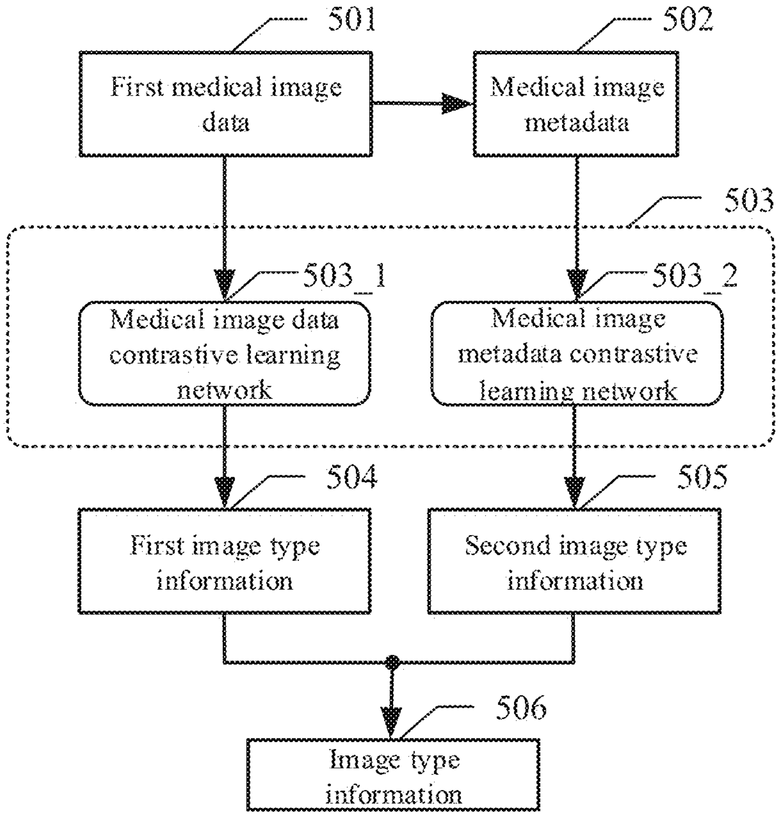
FIG. 5A schematically shows a schematic diagram of an example of determining an image type information according to an embodiment of the present disclosure.

FIG. 5A schematically shows a schematic diagram of an example of determining an image type information according to an embodiment of the present disclosure.

As shown in FIG. 5A, medical image metadata 502 may be obtained according to first medical image data 501. A contrastive learning network 503 may include a medical image data contrastive learning network 503_1, and a medical image metadata contrastive learning network 503_2.

The first medical image data 501 may be input into the medical image data contrastive learning network 503_1 to obtain a first image type information 504. The medical image metadata 502 may be input into the medical image metadata contrastive learning network 503_2 to obtain a second image type information 505. An image type information 506 may be obtained according to the first image type information 504 and the second image type information 505.

According to embodiments of the present disclosure, the medical image data contrastive learning network may include an image feature extraction network and a first classification network.

According to embodiments of the present disclosure, the image feature extraction network may be trained as follows.

The image feature extraction network may be obtained by training, based on a fifth loss function, a first self-supervised network according to a first sample representation vector of positive sample medical image data and second sample representation vectors of a plurality of negative sample medical image data corresponding to the positive sample medical image data. The first sample representation vector may be obtained by processing the positive sample medical image data using the first self-supervised network. The second sample representation vector may be obtained by processing the negative sample medical image data using the first self-supervised network.

According to embodiments of the present disclosure, the medical image data contrastive learning network may include an image feature extraction network and a first classification network. The image feature extraction network may be trained based on first medical image data not containing label information. The first classification network may be trained based on first medical image data containing label information.

According to embodiments of the present disclosure, the image feature extraction network and the first classification network may be trained for multiple rounds until a predetermined condition is met. The trained image feature extraction network and the trained first classification network may be determined as the medical image data contrastive learning network. The enhanced first medical image data may be processed using the image feature extraction network to obtain a representation vector corresponding to the first medical image data. The representation vector corresponding to the first medical image data may be processed using the first classification network to obtain the first image type information. The image feature extraction network and the first classification network may be determined according to actual service needs and are not limited here.

According to embodiments of the present disclosure, the plurality of negative sample medical image data may be determined from a plurality of candidate negative sample medical image data corresponding to the positive sample medical image data. The plurality of negative sample medical image data may be determined from the plurality of candidate negative sample medical image data according to a first similarity between the first sample representation vector of the positive sample medical image data and the second sample representation vector of the plurality of negative sample medical image data corresponding to the positive sample medical image data.

For example, it is possible to determine a first similarity between the first sample representation vector of the positive sample medical image data and the second sample representation vector of each of the plurality of negative sample medical image data, so as to obtain a plurality of first similarities. The plurality of negative sample medical image data may be determined from the plurality of candidate negative sample medical image data according to a first predetermined similarity threshold and the plurality of first similarities. For the candidate negative sample medical image data, in a case that the first similarity between the first sample representation vector of the positive sample medical image data and the second sample representation vector of the candidate negative sample medical image data is less than or equal to the first predetermined similarity threshold, the candidate negative sample medical image data is determined as the negative sample medical image data. The first predetermined similarity threshold may be determined according to actual service needs and is not limited here.

According to embodiments of the present disclosure, the first classification network may be trained as follows.

The first classification network may be obtained by training, based on a sixth loss function, the first classification network according to a first sample image type prediction information and a first sample image type label information of fourth sample medical image data. The first sample image type prediction information may be obtained by processing the fourth sample medical image data using the first classification network.

According to embodiments of the present disclosure, the image feature extraction network may include a third encoder and a first feed-forward neural network. The first classification network may include an image feature extraction network and a first normalization layer.

According to embodiments of the present disclosure, training the first classification network based on the sixth loss function according to the first sample image type prediction information and the first sample image type label information of the fourth sample medical image data may include the following operations.

The first classification network may be obtained by adjusting a model parameter of the first feed-forward neural network according to a fifth loss function value. The fifth loss function value may be obtained by training, based on the sixth loss function, the first classification network according to the first sample image type prediction information and the first sample image type label information of the fourth sample medical image data.

According to embodiments of the present disclosure, the first medical image data may be processed using the image feature extraction network to obtain a first intermediate image type information. The first intermediate image type information may be processed using the first classification network to obtain the first image type information.

Figure 5B:
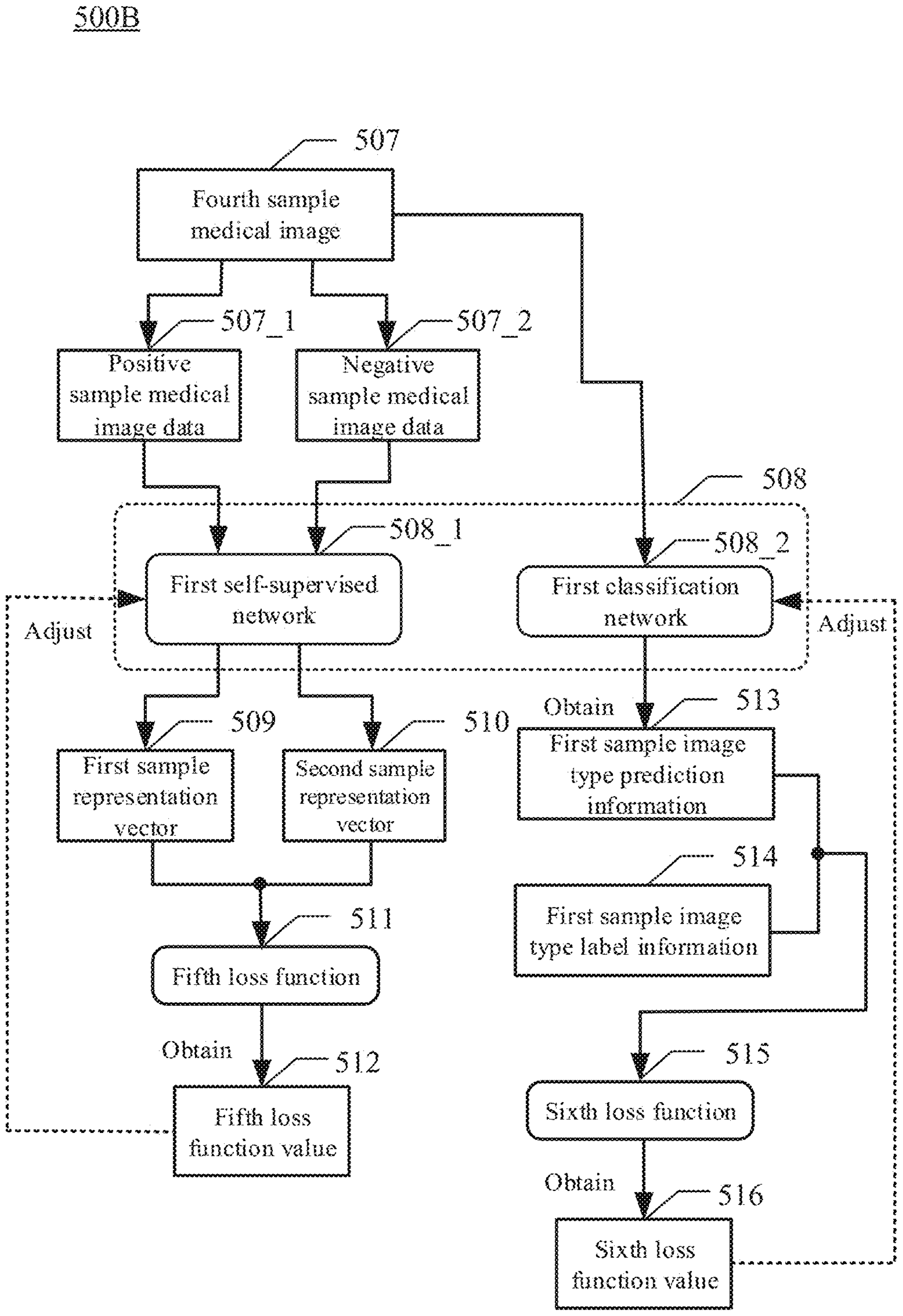
FIG. 5B schematically shows a schematic diagram of an example of a process of training a contrastive learning network for medical image data according to an embodiment of the present disclosure.

FIG. 5B schematically shows a schematic diagram of an example of a process of training a medical image data contrastive learning network according to an embodiment of the present disclosure.

As shown in FIG. 5B, a medical image data contrastive learning network 508 may include a first self-supervised network 508_1 and a first classification network 508_2. Fourth sample medical image data 507 may include positive sample medical image data 507_1 and a plurality of negative sample medical image data 507_2. The positive sample medical image data 507_1 may be processed using the first self-supervised network 508_1 to obtain a first sample representation vector 509. The negative sample medical image data 507_2 may be processed using the first self-supervised network 508_1 to obtain a second sample representation vector 510.

The first sample representation vector 509 of the positive sample medical image data 507_1 and the second sample representation vector 510 of the plurality of negative sample medical image data 507_2 corresponding to the positive sample medical image data 507_1 may be input into a fifth loss function 511 to obtain a fifth loss function value 512. A model parameter of the first self-supervised network 508_1 may be adjusted according to the fifth loss function value 512.

On this basis, the fourth sample medical image data 508 may be processed using the first classification network 508_2 to obtain a first sample image type prediction information 513. The first sample image type prediction information 513 and a first sample image type label information 514 may be input into a sixth loss function 515 to obtain a sixth loss function value 516. A model parameter of the first classification network 508_2 may be adjusted according to the sixth loss function value 516.

According to embodiments of the present disclosure, the medical image metadata contrastive learning network may include a metadata feature extraction network and a second classification network.

According to embodiments of the present disclosure, the metadata feature extraction network may be trained as follows.

The metadata feature extraction network may be obtained by training, based on a seventh loss function, a second self-supervised network according to a third sample representation vector of positive sample medical image metadata and a fourth sample representation vector of a plurality of negative sample medical image metadata corresponding to the positive sample medical image metadata. The third sample representation vector may be obtained by processing the positive sample medical image metadata using the second self-supervised network. The fourth sample representation vector may be obtained by processing the negative sample medical image metadata using the second self-supervised network.

According to embodiments of the present disclosure, the medical image metadata contrastive learning network may include a metadata feature extraction network and a second classification network. The metadata feature extraction network may be trained based on medical image metadata not containing label information. The second classification network may be trained based on medical image metadata containing label information.

According to embodiments of the present disclosure, the metadata feature extraction network and the second classification network may be trained for multiple rounds until a predetermined condition is met. The trained metadata feature extraction network and the trained second classification network may be determined as the medical image metadata contrastive learning network. The enhanced medical image metadata may be processed using the metadata feature extraction network to obtain a representation vector corresponding to the medical image metadata. The representation vector corresponding to the medical image metadata may be processed using the second classification network to obtain the second image type information. The metadata feature extraction network and the second classification network may be determined according to actual service needs and are not limited here.

According to embodiments of the present disclosure, the plurality of negative sample medical image metadata may be determined from a plurality of candidate negative sample medical image metadata corresponding to the positive sample medical image metadata. The plurality of negative sample medical image metadata may be determined from the plurality of candidate negative sample medical image metadata according to a second similarity between the third sample representation vector of the positive sample medical image metadata and the fourth sample representation vector of the plurality of negative sample medical image metadata corresponding to the positive sample medical image metadata.

For example, it is possible to determine a second similarity between the third sample representation vector of the positive sample medical image metadata and the fourth sample representation vector of each of the plurality of negative sample medical image metadata, so as to obtain a plurality of second similarities. A plurality of negative sample medical image metadata may be determined from the plurality of candidate negative sample medical image metadata according to a second predetermined similarity threshold and the plurality of second similarities. For the candidate negative sample medical image metadata, in a case that the second similarity between the third sample representation vector of the positive sample medical image metadata and the fourth sample representation vector of the candidate negative sample medical image metadata is less than or equal to the second predetermined similarity threshold, the candidate negative sample medical image metadata is determined as the negative sample medical image metadata. The second predetermined similarity threshold may be determined according to actual service needs and is not limited here.

According to embodiments of the present disclosure, the second self-supervised network may include a fifth encoder and a sixth encoder. The fifth encoder and the sixth encoder may be trained for multiple rounds until a predetermined condition is met. The trained fifth encoder and the trained sixth encoder may be determined as the metadata feature extraction network.

According to embodiments of the present disclosure, the second classification network may be trained as follows.

The second classification network may be obtained by training, based on an eighth loss function, the second classification network according to a second sample image type prediction information and a second sample image type label information of the sample medical image metadata. The second sample image type prediction information may be obtained by processing the sample medical image metadata using the second classification network.

According to embodiments of the present disclosure, the metadata feature extraction network may include a fourth encoder and a second feed-forward neural network. The second classification network may include the metadata feature extraction network and a second normalization layer.

According to embodiments of the present disclosure, training the second classification network based on the eighth loss function according to the second sample image type prediction information and the second sample image type label information of the sample medical image metadata may include the following operations.

The second classification network may be obtained by adjusting a model parameter of the second feed-forward neural network according to a sixth loss function value. The sixth loss function value may be obtained based on the eighth loss function according to the second sample image type prediction information and the second sample image type label information of the sample medical image metadata.

According to embodiments of the present disclosure, the fifth loss function and the seventh loss function may include at least one of InfoNCE (Info Noise-contrastive Estimation) or NCE (Noise-Contrastive Estimation Loss). The fifth loss function and the seventh loss function may be determined according to actual service needs and are not limited here. For example, the fifth loss function and the seventh loss function may be determined according to Equation (4) to Equation (6). The fifth loss function and the seventh loss function may be the same or different.

$$l(c, d) = -\log \frac{\exp\left(\frac{z_c, z_d}{\tau}\right)}{\sum_{k=1, k \neq c}^{2Z} \exp\left(\frac{z_c, z_k}{\tau}\right)} \tag{4}$$

$$L_e = -\frac{1}{2Z}\sum_{k=1}^{Z}[l(2k-1, 2k) + l(2k, 2k-1)] \tag{5}$$

$$L = \frac{1}{E}\sum_{e=1}^{E} L_e \tag{6}$$

where 2 Z may represent a sample quantity of the sample medical image data, and Z is an integer greater than or equal to 1. l(c,d) may represent a contrastive loss between a $c^{th}$ parent sample medical image data and a $d^{th}$ positive sample medical image data, $z_c$ may represent a sample representation vector of the $c^{th}$ parent sample medical image data, $z_d$ may represent a first sample representation vector of the $d^{th}$ positive sample medical image data corresponding to the $c^{th}$ parent sample medical image data, $z_k$ may represent a second sample representation vector of a $k^{th}$ negative sample medical image data corresponding to the $d^{th}$ positive sample medical image data, and $c, d, k \in \{1, 2, \ldots, (2Z-1), 2Z\}$. $\tau$ may represent a temperature parameter, $L_e$ may represent a loss function of an $e^{th}$ group of medical image data in the sample medical image data, and $e \in \{1, 2, \ldots, (E-1), E\}$. E may represent the number of groups included in the sample medical image data, and E is an integer greater than or equal to 1. L may represent the fifth loss function or the seventh loss function.

According to embodiments of the present disclosure, the medical image metadata may be processed using the metadata feature extraction network to obtain a second intermediate image type information. The second intermediate image type information may be processed using the second classification network to obtain the second image type information.

Figure 5C:
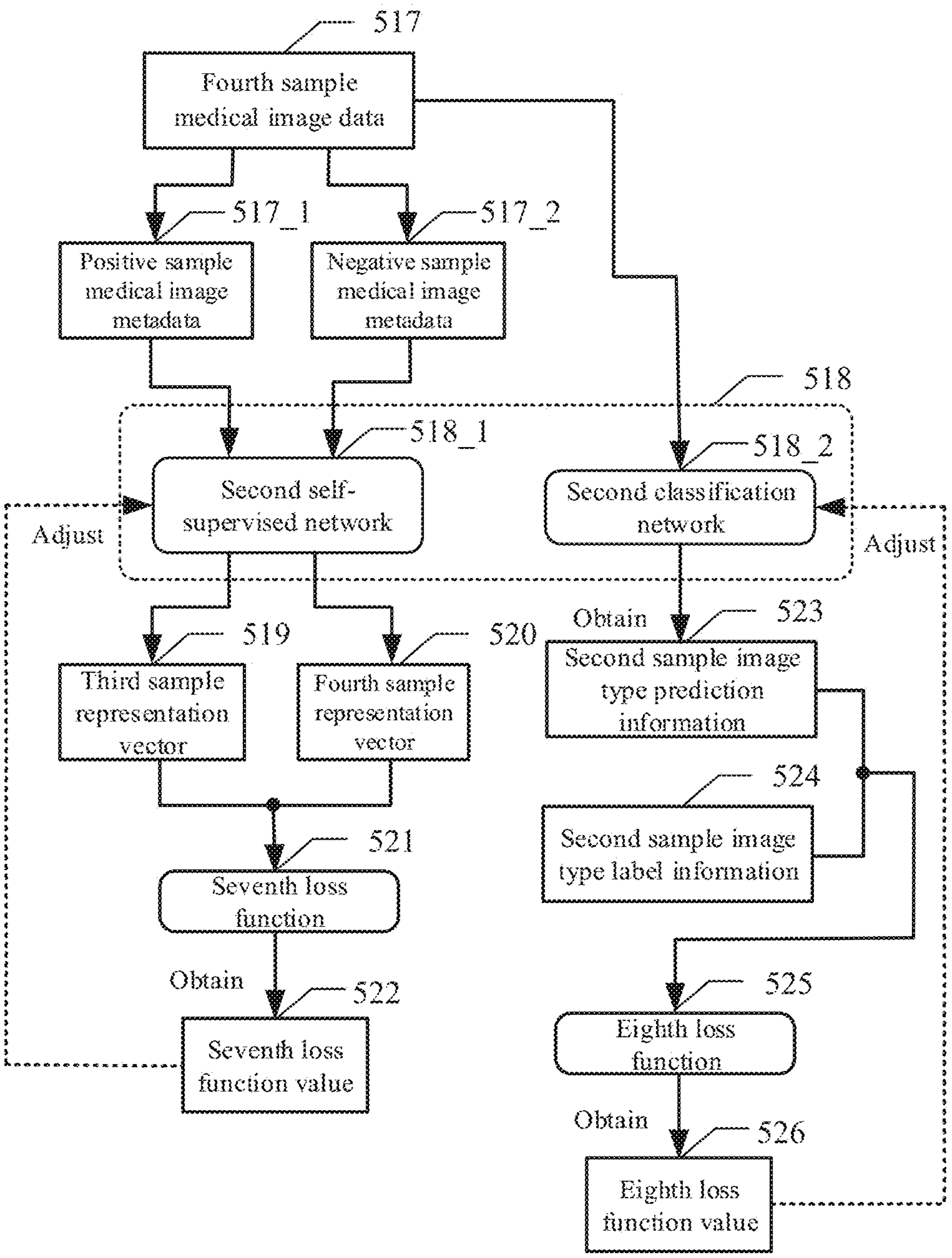
FIG. 5C schematically shows a schematic diagram of an example of a process of training a medical image metadata contrastive learning network according to an embodiment of the present disclosure.

FIG. 5C schematically shows a schematic diagram of an example of a process of training a medical image metadata contrastive learning network according to an embodiment of the present disclosure.

As shown in FIG. 5C, a medical image metadata contrastive learning network 518 may include a second self-supervised network 518_1 and a second classification network 518_2. Fourth sample medical image data 517 may include positive sample medical image data 517_1 and a plurality of negative sample medical image data 517_2. The positive sample medical image data 517_1 may be processed using the second self-supervised network 518_1 to obtain a third sample representation vector 519. The negative sample medical image data 517_2 may be processed using the second self-supervised network 518_1 to obtain a fourth sample representation vector 520.

The third sample representation vector 519 of the positive sample medical image data 517_1 and the fourth sample representation vector 520 of the plurality of negative sample medical image data 517_2 corresponding to the positive medial image data 517_1 may be input into a seventh loss function 521 to obtain a seventh loss function value 522. A model parameter of the second self-supervised network 518_1 may be adjusted according to the seventh loss function value 522.

On this basis, the fourth sample medical image data 517 may be processed using the second classification network 518_2 to obtain a second sample image type prediction information 523. The second sample image type prediction information 523 and a second sample image type label information 524 may be input into an eighth loss function 525 to obtain an eighth loss function value 526. A model parameter of the second classification network 518 may be adjusted according to the eighth loss function value 526.

According to embodiments of the present disclosure, obtaining the image type information according to the first image type information and the second image type information may include one of: determining the first image type information as the image type information; determining the second image type information as the image type information; or performing a soft voting decision on the first image type information and the second image type information to obtain the image type information.

According to embodiments of the present disclosure, the soft voting decision may refer to determining an average probability value of probabilities of belonging to a particular image type that are respectively indicated by the first image type information and the second image type information as a criterion, and determining an image type corresponding to a greatest probability as the image type information.

For example, taking binary classification as an example, the image type information may include an image type E and an image type F. The first image type information may indicate a 60% probability of belonging to the image type E and a 40% probability of belonging to the image type F. The second image type information may indicate an 80% probability of belonging to the image type E and a 20% probability of belonging to the image type F. When the soft voting decision is performed on the first image type information and the second image type information based on the average probability value, it may be obtained that the probability of belonging to the image type E is 70%, and the probability of belonging to the image type F is 30%. Then, it may be determined that the image type information is the image type E.

Alternatively, the soft voting decision may also refer to weighting the probabilities of belonging to a particular image type that are respectively indicated by the first image type information and the second image type information, and determining the image type corresponding to an obtained weighted probability value as the image type information.

For example, a first weight corresponding to the first image type information may be set to 0.6, and a second weight corresponding to the second image type information may be set to 0.4. When the soft voting decision is performed on the first image type information and the second image type information based on the weighted probability value, it may be obtained that the probability of belonging to the image type E is 68%, and the probability of belonging to the image type F is 32%. Then, it may be determined that the image type information is the image type E.

According to embodiments of the present disclosure, the first image feature is obtained by processing the first medical image data. On this basis, the first gene mutation information may be obtained according to the first image feature. The first medical image data is obtained by preprocessing the original medical image, and the preprocessing may include at least one of image clipping, re-sampling or data standardization. Therefore, the image feature may be extracted more accurately. In addition, after the image clipping is performed, it is possible to reduce an image size and improve a computational efficiency while effectively ensuring the accuracy of extracting the image feature and predicting the gene mutation.

According to embodiments of the present disclosure, the method 200 of processing the medical data may further include the following operations.

First sample data is acquired. The first sample data includes first sample medical image data and a first sample gene mutation label information corresponding to the first sample medical image data. The first sample medical image data is input into the first feature extraction network and the classification network to obtain the first sample gene mutation prediction information corresponding to the first sample medical image data. The first sample gene mutation prediction information and the first sample gene mutation label information are input into a first loss function to obtain a first loss function value. A model parameter of the first feature extraction network and a model parameter of the classification network are adjusted according to the first loss function value.

According to embodiments of the present disclosure, the first sample gene mutation label information may refer to a true gene mutation information of the first sample medical image data. For the explanation of the first sample medical image data and the first sample gene mutation prediction information, reference may be made to relevant contents of the first medical image data and the first gene mutation information described above, which will not be repeated here.

According to embodiments of the present disclosure, the first sample medical image data may be processed using the first feature extraction network and the classification network to obtain the first sample gene mutation prediction information corresponding to the first sample medical image data. The first sample gene mutation prediction information and the first sample gene mutation label information are input into the first loss function to obtain the first loss function value. The model parameter of the first feature extraction network and the model parameter of the classification network may be adjusted according to the first loss function value until a predetermined end condition is met. The first feature extraction network and the classification network obtained when the predetermined end condition is met may be determined as the trained first feature extraction network and the trained classification network. The predetermined end condition may include that a model iteration meets a predetermined number of times or the loss function converges.

According to embodiments of the present disclosure, the first loss function may be determined according to actual service needs and is not limited here. For example, the first loss function may be shown as Equation (7).

$$L_{GMS} = -\sum_{g=1}^{g}(y^g \log(\delta(\overline{y}^g)) + (1 - y^g)\log(1 - \delta(\overline{y}^g))) \tag{7}$$

where $L_{GMS}$ may represent the first loss function, $\overline{y}^8$ may represent the first sample gene mutation prediction information for a $g^{th}$ gene mutation category of the first sample medical image data, $y^g$ may represent the first sample gene mutation label information for the $g^{th}$ gene mutation category of the first sample medical image data, G may represent the number of gene mutation categories, and G may be an integer greater than or equal to 1. $g \in \{1, 2, \ldots, (G-1), G\}$. $\delta(\ )$ may represent a Sigmoid function, and $\delta(\overline{y}^g)$ may represent a Sigmoid function value of $\overline{y}^g$. $\delta(\overline{y}^g) \in (0,1)$.

According to embodiments of the present disclosure, a joint training of image segmentation and multi-mutation testing is achieved by training the first feature extraction network and the classification network using the first sample gene mutation prediction information and the first sample gene mutation label information. Moreover, the testing is performed for a plurality of gene mutations, and a mutual influence between mutations may be utilized, so that a prediction accuracy of the first feature extraction network and the classification network may be improved.

Figure 6:
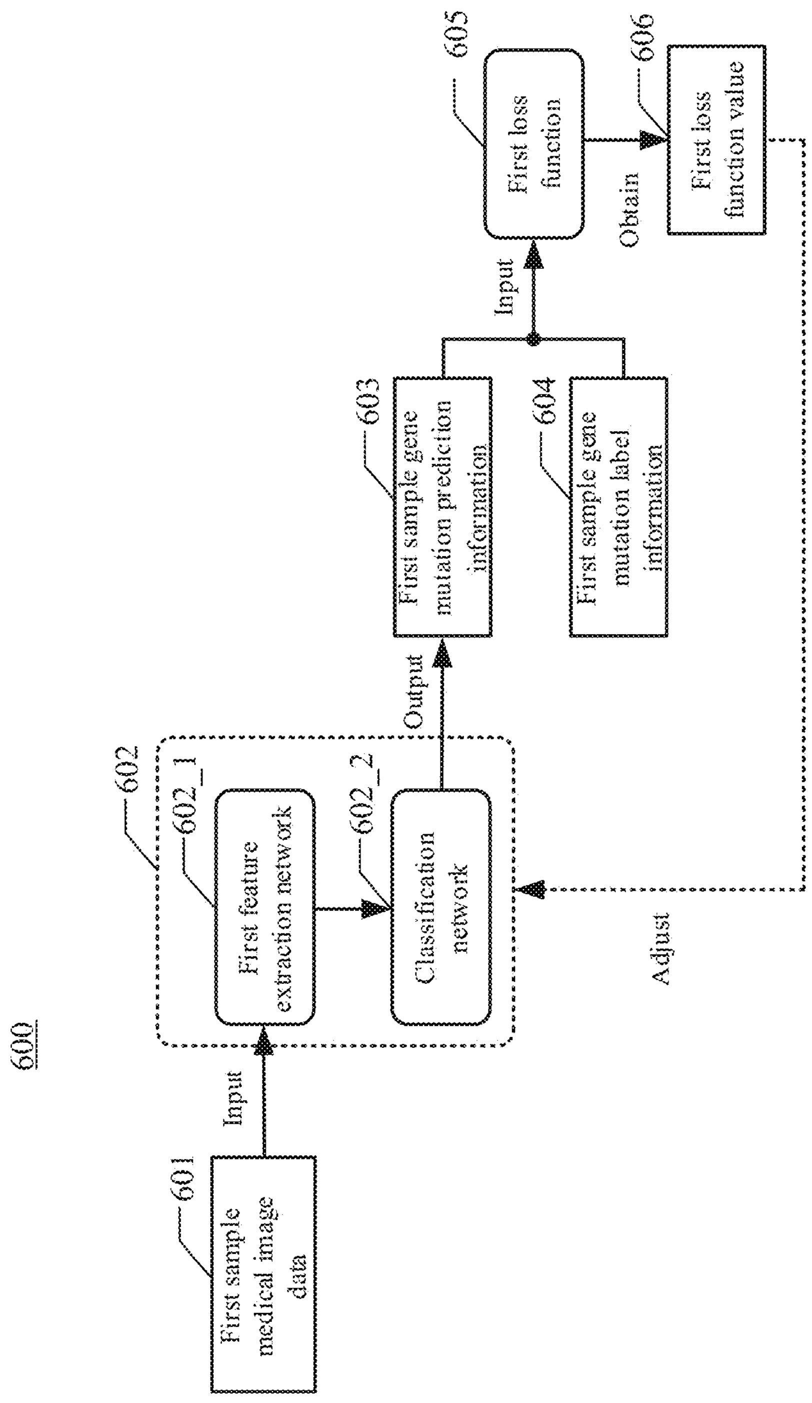
FIG. 6 schematically shows a schematic diagram of an example of a process of training a first feature extraction network and a classification network according to an embodiment of the present disclosure.

FIG. 6 schematically shows a schematic diagram of an example of a process of training a first feature extraction network and a classification network according to an embodiment of the present disclosure.

As shown in FIG. 6, first sample data may be acquired in the training process of the first feature extraction network and the classification network. The first sample data may include first sample medical image data 601 and a first sample gene mutation label information 604 corresponding to the first sample medical image data 601. The first sample medical image data 601 may be processed using a first feature extraction network 602_1 and a classification network 602_2, so as to obtain a first sample gene mutation prediction information 603 corresponding to the first sample medical image data 601.

After the first sample gene mutation prediction information 603 is obtained, the first sample gene mutation prediction information 603 and the first sample gene mutation label information 604 may be input into a first loss function 605 to obtain a first loss function value 606. After the first loss function value 606 is obtained, a model parameter of the first feature extraction network 602_1 and a model parameter of the classification network 602_2 may be adjusted according to the first loss function value 606.

The above are just exemplary embodiments. The present disclosure is not limited to the above, and may further include other methods of processing medical data known in the art, as long as the first feature extraction network and the classification network are able to be trained.

Figure 7:
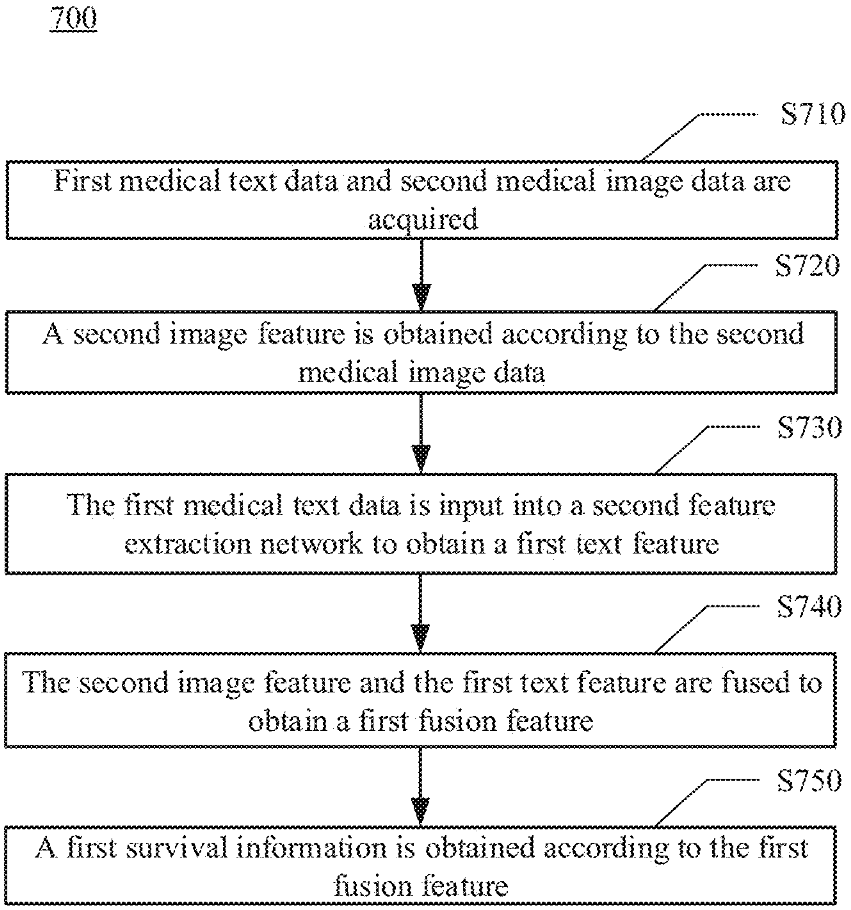
FIG. 7 schematically shows a flowchart of a method of processing medical data according to another embodiment of the present disclosure.

FIG. 7 schematically shows a flowchart of a method of processing medical data according to another embodiment of the present disclosure.

As shown in FIG. 7, a method 700 includes operation S710 to operation S750.

In operation S710, first medical text data and second medical image data are acquired.

In operation S720, a second image feature is obtained according to the second medical image data.

In operation S730, the first medical text data is input into a second feature extraction network to obtain a first text feature.

In operation S740, the second image feature and the first text feature are fused to obtain a first fusion feature.

At operation S750, a first survival information is obtained according to the first fusion feature.

According to embodiments of the present disclosure, the first medical text data may refer to a written record made by medical personnel regarding patient experience and treatment status. The first medical text data may include clinical data of the patient. The clinical data may include at least one of gender, age, histological diagnosis, tumor grading, medication information, history of malignant tumor, or survival feature. In addition, the clinical data may further include at least one of gene mutation result, other relevant disease information, past medical history information, examination result, diagnosis and treatment information, or disease development information. Other relevant disease information may include at least one of other relevant disease information of the patient or other relevant disease information of a family member. The examination result may include at least one of physical examination result or other examination results. The diagnosis and treatment information may include at least one of diagnostic information, nursing information, or treatment information. The disease development information may include a course of progressive disease and an outcome of progressive disease.

According to embodiments of the present disclosure, the second image features may be obtained according to the second medical image data. For example, the second medical image data may be input into a fifth feature extraction network to obtain the second image feature. The fifth feature extraction network may include a seventh feature extraction module. The seventh feature extraction module may be used to: determine a fourth image query matrix and a fourth image key matrix according to the second medical image data; determine a fourth image weight matrix according to the fourth image query matrix and the fourth image key matrix, where the fourth image weight matrix represents a correlation information between each two second medical images in the second medical image data; and determine the second image feature according to the fourth image weight matrix and the second medical image data.

According to embodiments of the present disclosure, the second medical image data may include a plurality of kinds of mono-modality medical image data. The fifth feature extraction network may include a plurality of fifth feature extraction sub-networks respectively corresponding to the plurality of kinds of mono-modality medical image data. The plurality of fifth feature extraction sub-networks share model parameters with each other. In this case, obtaining the second image feature according to the second medical image data may include: inputting the plurality of kinds of mono-modality medical image data respectively into their respective fifth feature extraction sub-networks, so as to obtaining a plurality of mono-modality image features.

According to embodiments of the present disclosure, the second medical image data may include multi-modality medical image data. The fifth feature extraction network may include a plurality of fifth feature extraction sub-networks. The plurality of fifth feature extraction sub-networks share model parameters with each other. In this case, obtaining the second image feature according to the second medical image data may include: inputting the multi-modality medical image data into the plurality of fifth feature extraction sub-networks to obtain a plurality of multi-modality image features.

According to embodiments of the present disclosure, the second feature extraction network may include a second feature extraction module. The second feature extraction module may be used to: determine a first text query matrix and a first text key matrix according to the first medical text data; determine a first text weight matrix according to the first text query matrix and the first text key matrix, where the first text weight matrix may represent a correlation information between each two first medical texts in the first medical text data; and determine the first text feature according to the first text weight matrix and the first medical text data. According to embodiments of the present disclosure, the first medical text data may be processed using the second feature extraction network to obtain the first text feature. The second feature extraction network may include at least one selected from: a second feature extraction network based on One-Hot encoding, a second feature extraction network based on Term Frequency-Inverse Document Frequency (i.e., TF-IDF), a second feature extraction network based on Expected Cross Entropy, a second feature extraction network based on Principal Component Analysis (PCA), or a second feature extraction network based on Auto Encoder (AE).

According to embodiments of the present disclosure, a gene mutation information and a chromosome mutation information of a patient may be encoded to obtain encoded data. The encoded data is merged with the first medical text data to obtain merged data. The merged data is input into the second feature extraction network to obtain the first text feature.

According to embodiments of the present disclosure, it is possible to further improve the accuracy of the survival information prediction by involving the encoded data obtained from the gene mutation information and the chromosome mutation information into the survival information prediction.

According to embodiments of the present disclosure, the first survival information may refer to an estimated survival time of a patient after suffering from a particular disease. The first survival information may be represented by a discrete numerical value. For example, an estimated survival time of 0~3 years may be represented by 1, an estimated survival time of 3 to 5 years may be represented by 2, and an estimated survival time of more than 5 years may be represented by 3.

According to embodiments of the present disclosure, the second image feature is determined according to the second medical image data, and the first text feature is obtained by processing the first medical text data using the second feature extraction network. Therefore, the first fusion feature obtained by fusing the second image feature with the first text feature may accurately represent the first medical text data and the second medical image data. On this basis, the first survival information is obtained according to the first fusion feature, thereby achieving a combination of image data feature extraction, text data feature extraction and survival information prediction, so that the comprehensiveness and accuracy of the survival information prediction may be improved.

The method 800 of processing the medical data according to embodiments of the present disclosure will be further described below with reference to FIG. 8 and FIG. 9.

According to embodiments of the present disclosure, operation S730 may include the following operations.

The first medical text data is encoded to obtain a first medical text vector. The first medical text vector is input into a first encoder to obtain a first hidden vector. The first hidden vector is input into a first decoder to obtain a first decoded vector. The first text feature is obtained according to the first hidden vector and the first decoded vector.

According to embodiments of the present disclosure, a second feature extraction network based on auto encoder is taken as an example of the second feature extraction network. The auto encoder may be determined according to actual service needs and is not limited here. For example, the auto encoder may include at least one of selected from: contractive auto encoder (CAE), regularized auto encoder (RAE), or variational auto encoder (VAE).

According to embodiments of the present disclosure, the auto encoder may include a first encoder and a first decoder. Both the first encoder and the first decoder use linear transformation functions. According to embodiments of the present disclosure, the first encoder may include an input layer and a hidden layer, which may be used to encode input data. For example, the first medical text data may be encoded using the input layer of the first encoder to obtain a first medical text vector $x_i$. The first medical text vector may be processed using the hidden layer of the first encoder to obtain a first hidden vector $h_i=f(x_i)$. The first decoder may include a hidden layer and an output layer, which may be used to reconstruct the input data. For example, the first hidden vector may be processed using the first decoder to obtain a first decoded vector $x'_i=g(h_i)$.

According to embodiments of the present disclosure, the first sample medical text data may be input into the auto encoder to obtain third sample medical text data. The first sample medical text data and the third sample medical text data may be input into a ninth loss function to obtain a ninth loss function value. A model parameter of the auto encoder may be adjusted according to the ninth loss function value until a predetermined end condition is met. The ninth loss function may be shown as Equation (8).

$$L_{auto-encoder} = \min \frac{1}{R} \sum_{r=1}^{R} \|x_r - x'_r\| \tag{8}$$

where $L_{auto-encoder}$ may represent the ninth loss function, $X_r$ may represent an $r^{th}$ first sample medical text data, $X'_r$ may represent the third sample medical text data corresponding to $X_r$, and R may represent a sample quantity of the first sample medical text data. R may be an integer greater than or equal to 1. $r \in \{1, 2, \ldots, (R-1), R\}$.

According to embodiments of the present disclosure, the second feature extraction network may include a plurality of stacked auto encoders. The plurality of stacked auto encoders may include an auto encoder 1, an auto encoder 2, . . . , an auto encoder w, . . . , an auto encoder W. W may be an integer greater than or equal to 1, and $w \in \{1, 2, \ldots, (W-1), W\}$.

According to embodiments of the present disclosure, the auto encoder 1 may be trained in an unsupervised manner until a minimum reconstruction error 1 corresponding to the auto encoder 1 reaches a predetermined threshold. On this basis, an output of the auto encoder 1 may be input into the auto encoder 2 to train the auto encoder 2 until a minimum reconstruction error 2 corresponding to the auto encoder 2 reaches a predetermined threshold. Then, the output of the auto encoder (W−1) may be input into the auto encoder W to train the auto encoder W until a minimum reconstruction error W corresponding to the auto encoder W reaches a predetermined threshold. In this case, the output of the auto encoder W may be determined as the first text feature. The predetermined threshold may be determined according to actual service needs and is not limited here.

According to embodiments of the present disclosure, operation S740 may include the following operations.

A second image query matrix and a second image key matrix are determined according to the second medical image data. A text query matrix and a text key matrix are determined according to the first medical text data. A first fusion weight matrix is determined according to the second image query matrix and the text key matrix. A second fusion weight matrix is determined according to the text query matrix and the second image key matrix. A first output feature vector is obtained according to the first fusion weight matrix and a text value matrix, where the text value matrix is obtained according to the first medical text data. A second output feature vector is obtained according to the second fusion weight matrix and a second image value matrix, where the second image value matrix is obtained according to the second medical image data. The first fusion feature is obtained according to the first output feature vector and the second output feature vector.

According to embodiments of the present disclosure, the second image feature may include the second image query matrix, the second image key matrix, and the second image value matrix. The second image query matrix, the second image key matrix and the second image value matrix may be determined according to the second medical image data. For example, the second image query matrix may be determined according to the second medical image data and a query parameter matrix, the second image key matrix may be determined according to the second medical image data and a key parameter matrix, and the second image value matrix may be determined according to the second medical image data and a value parameter matrix.

According to embodiments of the present disclosure, the first text feature may include the text query matrix, the text key matrix, and the text value matrix. The text query matrix and the text key matrix may be determined according to the first medical text data. For example, the text query matrix may be determined according to the first medical text data and the query parameter matrix, the text key matrix may be determined according to the first medical text data and the key parameter matrix, and the text value matrix may be determined according to the first medical text data and the value parameter matrix.

According to embodiments of the present disclosure, the query parameter matrix, the key parameter matrix and the value parameter matrix may be determined according to actual service needs and are not limited here. For example, the query parameter matrix, the key parameter matrix and the value parameter matrix may be used to represent trainable parameter matrices.

According to embodiments of the present disclosure, after the second image feature and the first text feature are obtained, the second image feature and the first text feature may be fused to obtain the first fusion feature. A specific method of feature fusion may be determined according to actual service needs and is not limited here. For example, the first fusion weight matrix may be determined according to the second image query matrix and the text key matrix, and the second fusion weight matrix may be determined according to the text query matrix and the second image key matrix.

According to embodiments of the present disclosure, after the first fusion weight matrix and the second fusion weight matrix are obtained, the first output feature vector and the second output feature vector may be determined according to the first fusion weight matrix, the second fusion weight matrix, the second image value matrix and the text value matrix. For example, the first output feature vector may be determined according to the first fusion weight matrix and the text value matrix, and the second output feature vector may be determined according to the second fusion weight matrix and the second image value matrix.

According to embodiments of the present disclosure, after the first output feature vector and the second output feature vector are obtained, the first fusion feature may be obtained according to the first output feature vector and the second output feature vector. For example, the first output feature vector and the second output feature vector may be concatenated to obtain the first fusion feature. FIG. 8 schematically shows a schematic diagram of an example of obtaining a first survival information based on a first fusion feature according to embodiments of the present disclosure.

Figure 8:
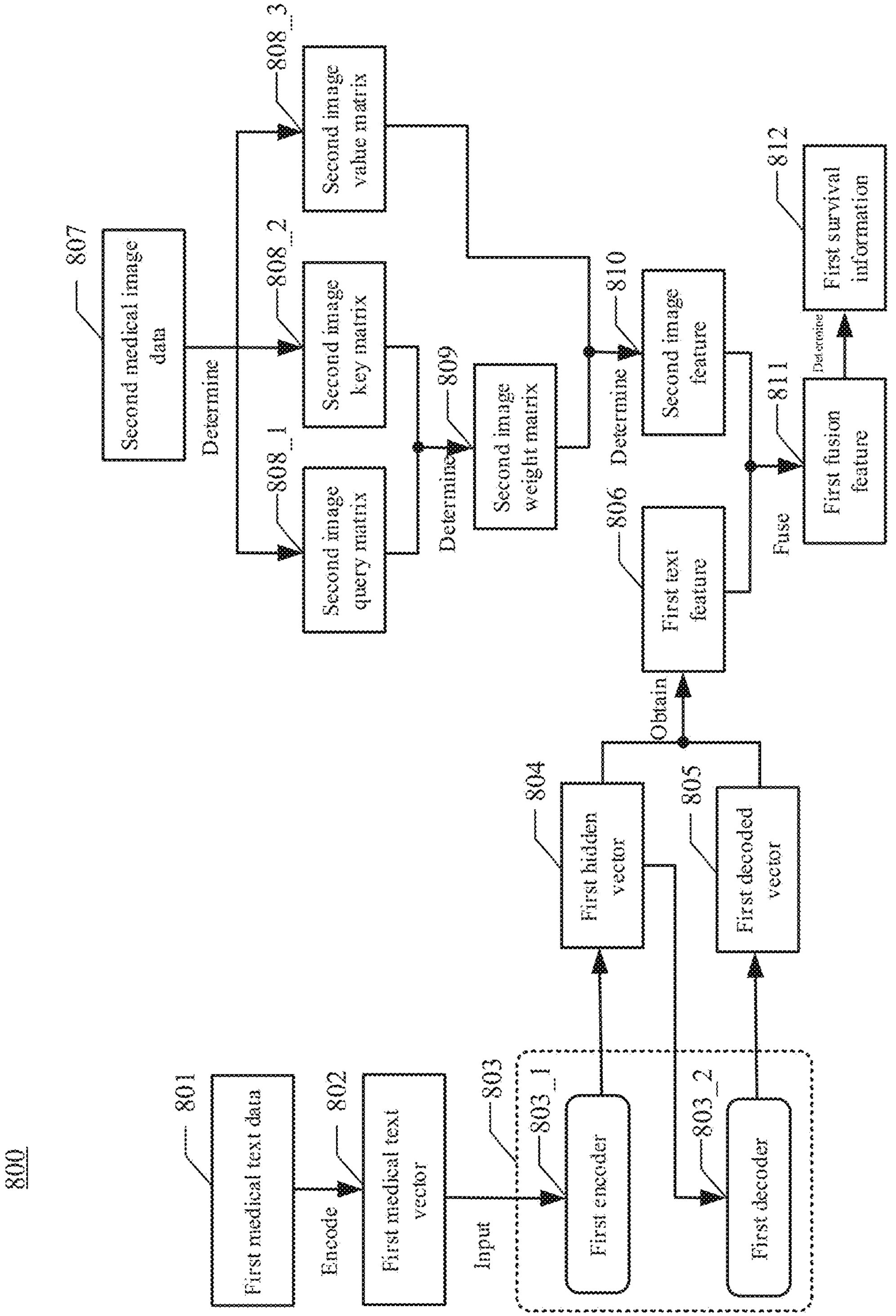
FIG. 8 schematically shows a schematic diagram of an example of obtaining a first survival information based on a first fusion feature according to an embodiment of the present disclosure.

As shown in FIG. 8, first medical text data 801 may be encoded to obtain a first medical text vector 802. The first medical text vector 802 is input into a first encoder 803_1 to obtain a first hidden vector 804. The first hidden vector 804 is input into a first decoder 803_2 to obtain a first decoded vector 805. A first text feature 806 is obtained according to the first hidden vector 804 and the first decoded vector 805.

A second image query matrix 808_1, a second image key matrix 808_2 and a second image value matrix 8083 may be determined according to second medical image data 807. A second image weight matrix 809 may be determined according to the second image query matrix 808_1 and the second image key matrix 808_2. A second image feature 810 may be obtained according to the second image weight matrix 809 and the second image value matrix 808_3.

After the first text feature 806 and the second image feature 810 are obtained, the first text feature 806 and the second image feature 810 are fused to obtain a first fusion feature 811. A first survival information 812 is obtained according to the first fusion feature 811.

According to embodiments of the present disclosure, a fusion deep learning model includes a second feature extraction network.

According to embodiments of the present disclosure, the method 800 of processing the medical data may further include the following operations.

Second sample data is acquired. The second sample data includes second sample medical data and a first sample survival label information corresponding to the second sample medical data. The second sample medical data includes the first sample medical text data and the second sample medical image data. The second sample medical data is input into the fusion deep learning network to obtain a first sample survival prediction information corresponding to the second sample medical data. The first sample survival prediction information and the first sample survival label information are input into a second loss function to obtain a second loss function value. A model parameter of the fusion deep learning network is adjusted according to the second loss function value.

According to embodiments of the present disclosure, the first sample survival label information may refer to a true survival information of the first sample medical data. For the explanation of the second sample medical image data and the first sample survival prediction information, reference may be made to relevant contents of the second medical image data and the first survival information described above, which will not be repeated here.

According to embodiments of the present disclosure, the first sample medical data may be processed using the fusion deep learning network to obtain a first sample survival prediction information corresponding to the first sample medical data. The first sample survival prediction information and the first sample survival label information may be input into the second loss function to obtain the second loss function value. The model parameter of the fusion deep learning network may be adjusted according to the second loss function value until a predetermined end condition is met. The fusion deep learning network obtained when the predetermined end condition is met may be determined as a trained fusion deep learning network. The predetermined end condition may include that a model iteration meets a predetermined number of times or the loss function converges.

According to embodiments of the present disclosure, the second loss function may be determined according to actual service needs and is not limited here. For example, the second loss function may be shown as Equation (9).

$$L_{SP} = -\sum_{s=1}^{S}(y^s \log(\delta(\bar{y}^s))) \tag{9}$$

where $L_{SP}$ may represent the second loss function value, $\bar{y}^s$ may represent the first sample survival prediction information for an $s^h$ survival category of the first sample medical data, $y^s$ may represent the first sample survival label information for the $s^{th}$ survival category of the first sample medical data, and S may represent the number of survival categories in the first sample medical data. S may be an integer greater than or equal to 1. $s \in \{1, 2, \ldots, (S-1), S\}$. $\delta(\ )$ may represent a Sigmoid function, and $\gamma(\bar{y}^g)$ may represent a Sigmoid function value of $\bar{y}^g$, and $\bar{y}^g \in (0,1)$.

Figure 9:
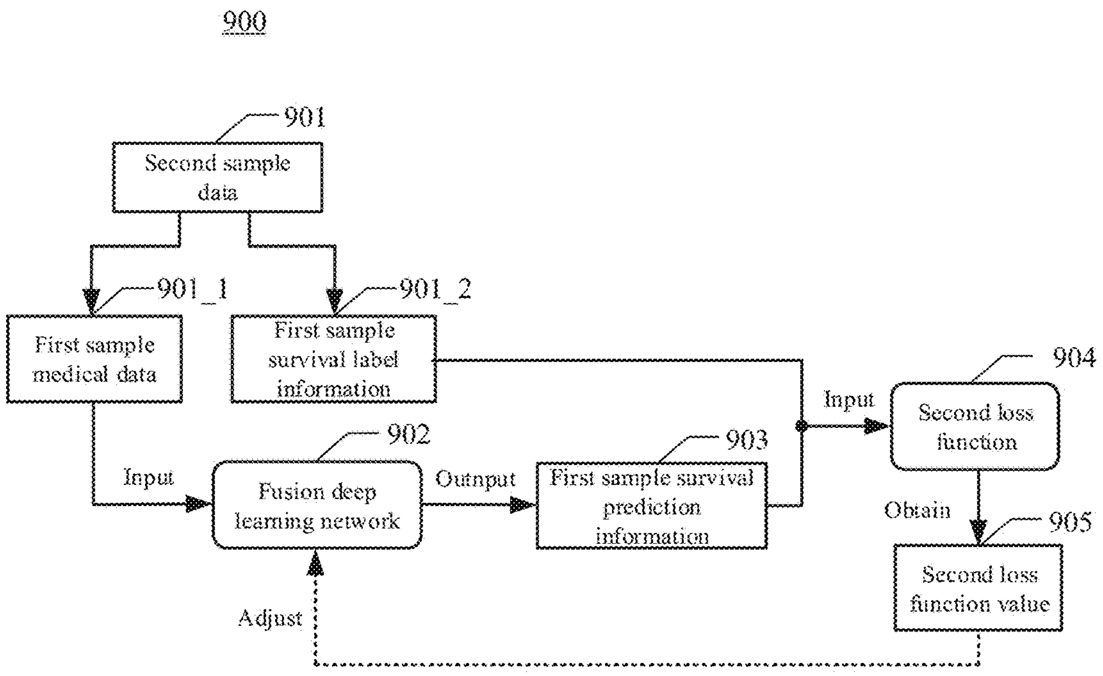
FIG. 9 schematically shows a schematic diagram of an example of a process of training a fusion deep learning network according to an embodiment of the present disclosure.

FIG. 9 schematically shows a schematic diagram of an example of a training process of a fusion deep learning network according to an embodiment of the present disclosure.

As shown in FIG. 9, second sample data 901 may be acquired during the training process of the fusion deep learning network. The second sample data 901 may include first sample medical data 901_1 and a first sample survival label information 901_2 corresponding to the first sample medical data 901_1. The first sample medical data 901_1 may be processed using the fusion deep learning network 902 to obtain a first sample survival prediction information 903 corresponding to the first sample medical data 901_1.

After the first sample survival prediction information 903 is obtained, the first sample survival prediction information 903 and the first sample survival label information 901_2 may be input into a second loss function 904 to obtain a second loss function value 905. After the second loss function value 905 is obtained, a model parameter of the fusion deep learning network 902 may be adjusted according to the second loss function value 905.

The above are just exemplary embodiments. The present disclosure is not limited to the above and may further include other methods of processing medical data known in the art, as long as the fusion deep learning network is able to be trained.

Figure 10:
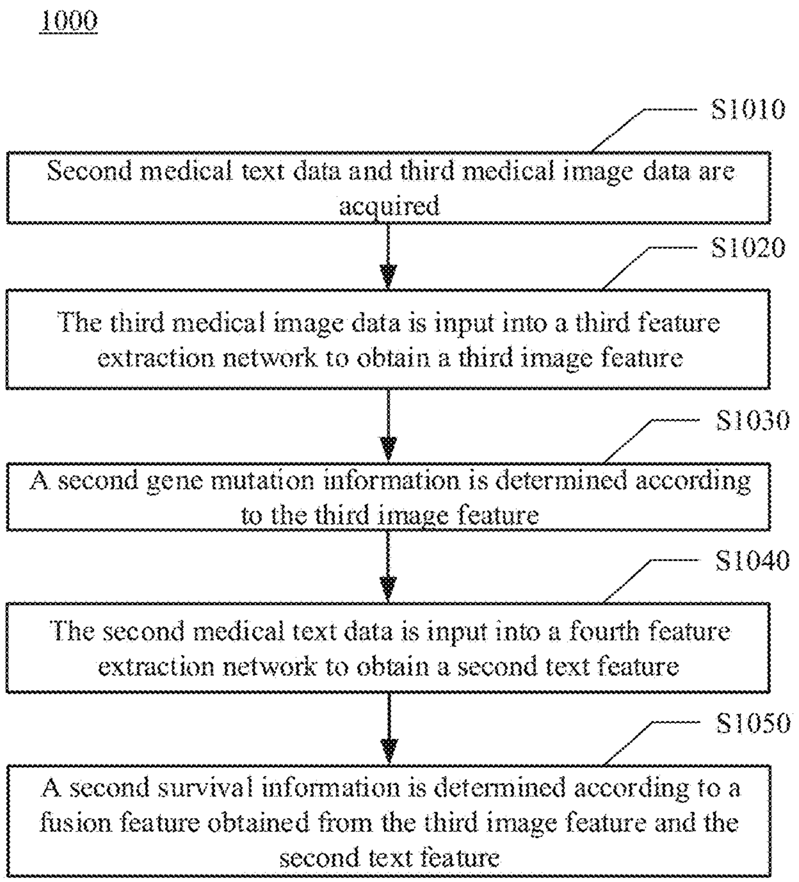
FIG. 10 schematically shows a flowchart of a method of analyzing medical data according to an embodiment of the present disclosure.

FIG. 10 schematically shows a flowchart of a method of analyzing medical data according to an embodiment of the present disclosure.

As shown in FIG. 10, a method 1000 includes operation S1010 to operation S1050.

In operation S1010, second medical text data and third medical image data are acquired.

In operation S1020, the third medical image data is input into a third feature extraction network to obtain a third image feature.

In operation S1030, a second gene mutation information is determined according to the third image feature.

In operation S1040, the second medical text data is input into a fourth feature extraction network to obtain a second text feature.

In operation S1050, a second survival information is determined according to a fusion feature obtained from the third image feature and the second text feature.

According to embodiments of the present disclosure, the third image feature and the second text feature may be fused to obtain a second fusion feature. The second survival information may be determined according to the second fusion feature. A feature fusion method may be determined according to actual service needs and is not limited here. For example, the feature fusion method may include at least one of feature concatenation, cross-modality attention, or condition batch normalization (CBN).

According to embodiments of the present disclosure, the third feature extraction network may include a fourth feature extraction module. The fourth feature extraction module is used to: determine a third image query matrix and a third image key matrix according to the third medical image data; determine a third image weight matrix according to the third image query matrix and the third image key matrix, where the third image weight matrix represents a correlation information between each two third medical images in the third medical image data; and determine the third image feature according to the third image weight matrix and the third medical image data.

According to embodiments of the present disclosure, the third medical image data may include a plurality of kinds of mono-modality medical image data. The third feature extraction network may include a plurality of third feature extraction sub-networks respectively corresponding to the plurality of kinds of mono-modality medical image data. The plurality of third feature extraction sub-networks share model parameters with each other. In this case, obtaining the third image feature according to the third medical image data may include: inputting the plurality of kinds of mono-modality medical image data respectively into their respective third feature extraction sub-networks, so as to obtain a plurality of mono-modality image features.

According to embodiments of the present disclosure, the third medical image data may include multi-modality medical image data. A fifth feature extraction network may include a plurality of third feature extraction sub-networks. The plurality of third feature extraction sub-networks share model parameters with each other. In this case, obtaining the third image feature according to the third medical image data may include: inputting the multi-modality medical image data into the plurality of third feature extraction sub-networks to obtain a plurality of multi-modality image features.

According to embodiments of the present disclosure, the fourth feature extraction network may include a fourth feature extraction module. The fourth feature extraction module may be used to: determine a second text query matrix and a second text key matrix according to the second medical text data; determine a second text weight matrix according to the second text query matrix and the second text key matrix, where the second text weight matrix may represent a correlation information between each two second medical texts in the second medical text data; and determine the second text feature according to the second text weight matrix and the second medical text data.

According to embodiments of the present disclosure, for the explanation of the third medical image data, the second medical text data, the third image feature, the second gene mutation information, the second text feature and the second survival information, reference may be made to relevant contents of the first medical image data, the first medical text data, the first image feature, the first gene mutation information, the first text feature and the first survival information described above, which will not be repeated here.

According to embodiments of the present disclosure, the first text feature obtained by the second feature extraction network may accurately represent the first medical text data. On this basis, the second image feature is determined according to the second medical image data. The first fusion feature is obtained by fusing the second image feature with the first text feature, thereby achieving a combination of image feature and text feature, so that the comprehensiveness and accuracy of the survival prediction may be improved.

The method 1000 of analyzing the medical data according to embodiments of the present disclosure will be further described below with reference to FIG. 11A, FIG. 11B, FIG. 11C, FIG. 11D, FIG. 12, FIG. 13A and FIG. 13B.

According to embodiments of the present disclosure, determining the third image feature according to the third image weight matrix and the third medical image data may include the following operations.

A third image value matrix is obtained according to the third medical image data. The third image feature is obtained according to the third image weight matrix and the third image value matrix.

Figure 11A:
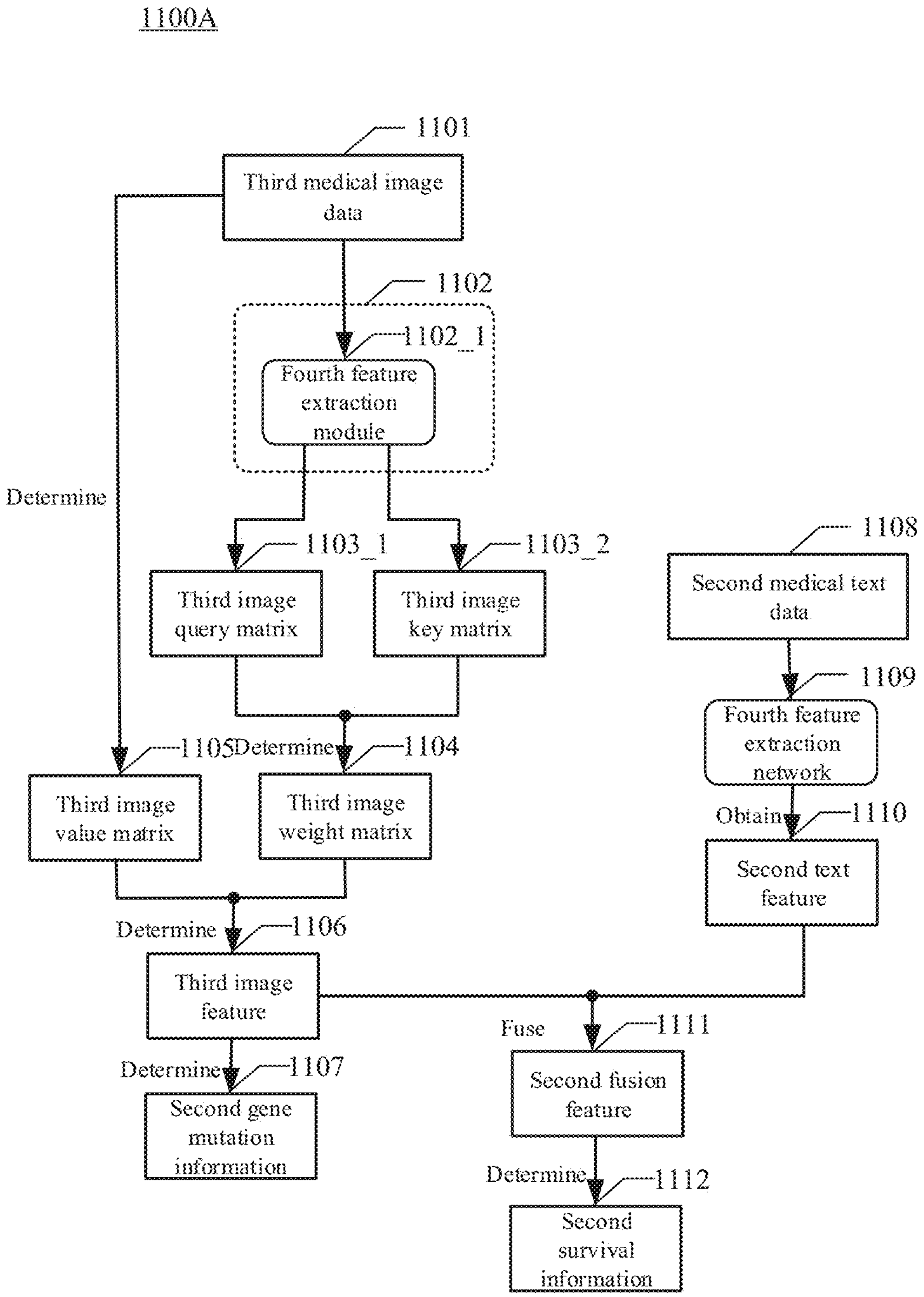
FIG. 11A schematically shows a schematic diagram of an example of determining a second gene mutation information and a second survival information according to an embodiment of the present disclosure.

FIG. 11A schematically shows a schematic diagram of an example of determining a second gene mutation information and a second survival information according to an embodiment of the present disclosure.

As shown in FIG. 11A, a third feature extraction network 1102 may include a fourth feature extraction module 1102_1.

Third medical image data 1101 and second medical text data 1108 may be acquired. The third medical image data 1101 may be processed using the fourth feature extraction module 1102_1 to obtain a third image query matrix 1103_1 and a third image key matrix 1103_2. A third image weight matrix 1104 may be determined according to the third image query matrix 1103_1 and the third image key matrix 1103_2.

A third image value matrix 1105 may be obtained according to the third medical image data 1101. A third image feature 1106 may be obtained according to the third image weight matrix 1104 and the third image value matrix 1105. A second gene mutation information 1107 may be determined according to the third image feature 1106.

The second medical text data 1108 may be processed using a fourth feature extraction network 1109 to obtain a second text feature 1110. A second fusion feature 1111 may be determined according to the third image feature 1106 and the second text feature 1110. A second survival information 1112 may be determined according to the second fusion feature 1111.

According to embodiments of the present disclosure, the third medical image data includes a plurality of third medical images, and the third feature extraction network further includes a fifth feature extraction module.

According to embodiments of the present disclosure, the method 1100 of analyzing the medical data may further include the following operations.

The plurality of third medical images are input into the fifth feature extraction module to obtain a second temporal image feature. The second temporal image feature represents a temporal relationship between the plurality of third medical images.

According to embodiments of the present disclosure, determining the third image query matrix and the third image key matrix according to the third medical image data may include the following operations.

The second temporal image feature is input into the fourth feature extraction module to obtain the third image query matrix and the third image key matrix.

Figure 11B:
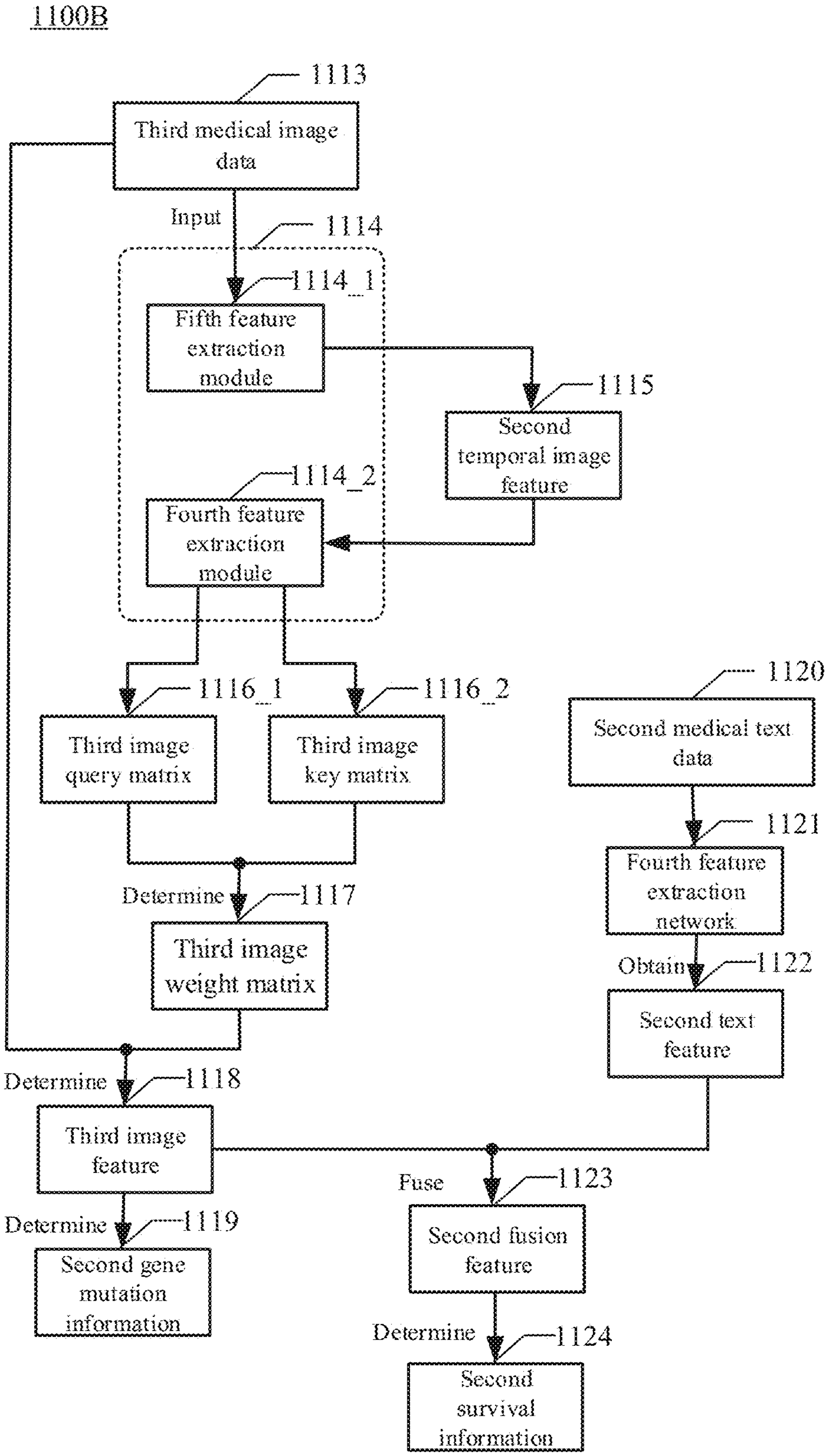
FIG. 11B schematically shows a schematic diagram of an example of determining a second gene mutation information and a second survival information according to another embodiment of the present disclosure.

FIG. 11B schematically shows a schematic diagram of an example of determining a second gene mutation information and a second survival information according to another embodiment of the present disclosure.

As shown in FIG. 11B, a third feature extraction network 1114 may include a fifth feature extraction module 1114_1 and a fourth feature extraction module 1114_2.

Third medical image data 1113 and second medical text data 1120 may be acquired. The third medical image data 1101 may be processed using the fifth feature extraction module 1114_1 to obtain a second temporal image feature 1115. The second temporal image feature 1115 may be processed using the fourth feature extraction module 1114_2 to obtain a third image query matrix 1116_1 and a third image key matrix 1116_2. A third image weight matrix 1117 may be determined according to the third image query matrix 1116_1 and the third image key matrix 1116_2.

A third image feature 1118 may be obtained according to the third image weight matrix 1117 and the third medical image data 1113. A second gene mutation information 1119 may be determine according to the third image feature 1118.

Second medical text data 1120 may be processed using a fourth feature extraction network 1121 to obtain a second text feature 1122. A second fusion feature 1123 may be determined according to the third image feature 1118 and the second text feature 1122. A second survival information 1124 may be determined according to the second fusion feature 1123.

According to embodiments of the present disclosure, the third feature extraction network further includes a sixth feature extraction module, which includes a second maximum pooling layer, a second residual unit, a second downsampling unit and a second average pooling layer.

According to embodiments of the present disclosure, the method 1100 of analyzing the medical data may further include the following operations.

A plurality of third medical images are input into the sixth feature extraction module to obtain a second intermediate image feature.

According to embodiments of the present disclosure, inputting the plurality of third medical images into the fifth feature extraction module to obtain the second temporal image feature may include the following operations.

The second intermediate image feature is input into the fifth feature extraction module to obtain the second temporal image feature.

Figure 11C:
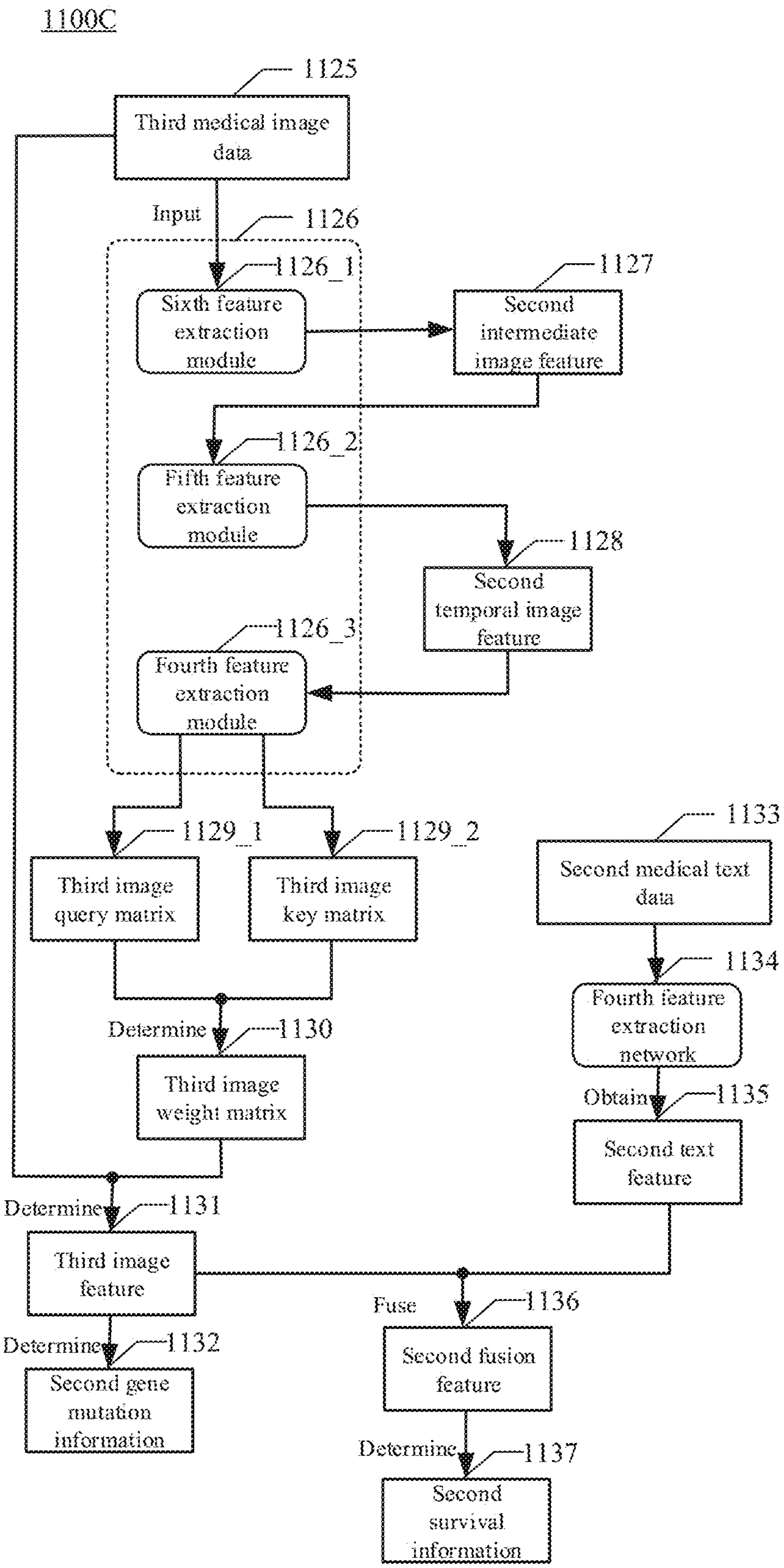
FIG. 11C schematically shows a schematic diagram of an example of determining a second gene mutation information and a second survival information according to another embodiment of the present disclosure.

FIG. 11C schematically shows a schematic diagram of an example of determining a second gene mutation information and a second survival information according to another embodiment of the present disclosure.

As shown in FIG. 11C, a third feature extraction network 1126 may include a sixth feature extraction module 1126_1, a fifth feature extraction module 1126_2 and a fourth feature extraction module 1126_3.

Third medical image data 1125 and second medical text data 1133 may be acquired. The third medical image data 1125 may be processed using the sixth feature extraction module 1126_1 to obtain a second intermediate image feature 1127. The second intermediate image feature 1127 may be processed using the fifth feature extraction module 1126_2 to obtain a second temporal image feature 1128. The second temporal image feature 1128 may be processed using the fourth feature extraction module 1126_3 to obtain a third image query matrix 1129_1 and a third image key matrix 1129_2. A third image weight matrix 1130 may be determined according to the third image query matrix 1129_1 and the third image key matrix 1129_2.

A third image feature 1131 may be obtained according to the third image weight matrix 1130 and the third medical image data 1125. A second gene mutation information 1132 may be determined according to the third image feature 1131.

Second medical text data 1133 may be processed using a fourth feature extraction network 1134 to obtain a second text feature 1135. A second fusion feature 1136 may be determined according to the third image feature 1131 and the second text feature 1135. A second survival information 1137 may be determined according to the second fusion feature 1136.

According to embodiments of the present disclosure, operation S1140 may include the following operations.

The second medical text data is encoded to obtain a second medical text vector. The second medical text vector is input into a second encoder to obtain a second hidden vector. The second hidden vector is input into a second decoder to obtain a second decoded vector. A second text feature is obtained according to the second hidden vector and the second decoded vector.

According to embodiments of the present disclosure, operation S1130 may include the following operations.

The third image feature is input into a third classification network to obtain the second gene mutation information.

According to embodiments of the present disclosure, operation S1150 may include the following operations.

A fusion feature obtained from the third image feature and the second text feature is input into a fourth classification network to obtain the second survival information.

According to embodiments of the present disclosure, the model parameters in the third feature extraction network, the fourth feature extraction network, the third classification network and the fourth classification network are obtained by joint training.

Figure 11D:
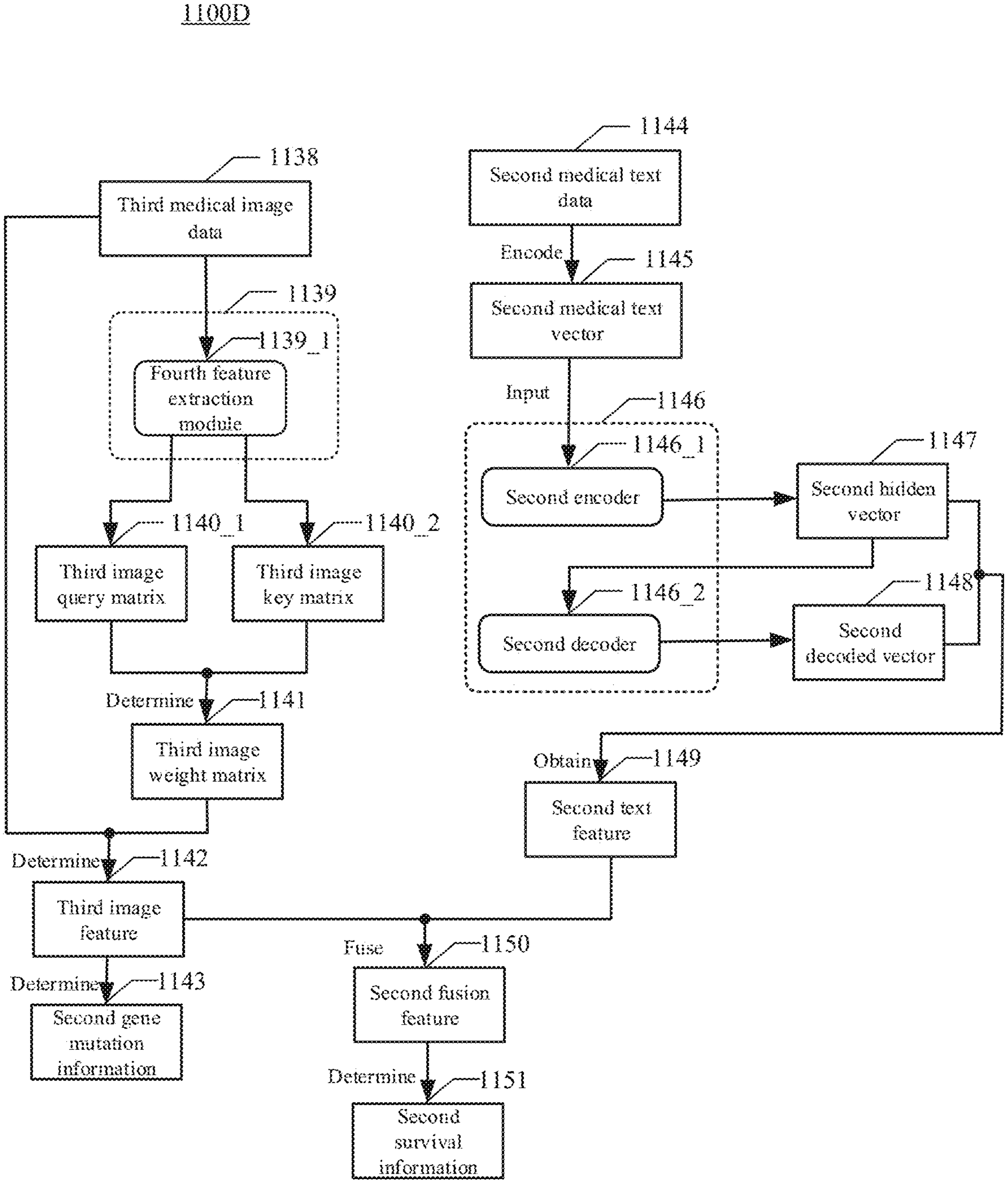
FIG. 11D schematically shows a schematic diagram of an example of determining a second gene mutation information and a second survival information according to another embodiment of the present disclosure.

FIG. 11D schematically shows a schematic diagram of an example of determining a second gene mutation information and a second survival information according to another embodiment of the present disclosure.

As shown in FIG. 11D, a third feature extraction network 1139 may include a fourth feature extraction module 1139_2. A fourth feature extraction network 1146 may include a second encoder 1146_1 and a second decoder 1146_2.

Third medical image data 1138 and second medical text data 1144 may be acquired. The third medical image data 1138 may be processed using the fourth feature extraction module 1139_2 to obtain a third image query matrix 1140_1 and a third image key matrix 1140_2. A third image weight matrix 1141 may be determined according to the third image query matrix 1140_1 and the third image key matrix 1140_2.

A third image feature 1142 may be obtained according to the third image weight matrix 1141 and the third medical image data 1138. A second gene mutation information 1143 may be determined according to the third image feature 1142.

Second medical text data 1144 may be encoded to obtain a second medical text vector 1145. The second medical text vector 1145 may be input into a second encoder 1146_1 to obtain a second hidden vector 1147. The second hidden vector 1147 may be input into a second decoder 1146_2 to obtain a second decoded vector 1148. A second text feature 1149 may be obtained according to the second hidden vector 1147 and the second decoded vector 1148.

A second fusion feature 1150 may be determined according to the third image feature 1142 and the second text feature 1149. A second survival information 1151 may be determined according to the second fusion feature 1150.

According to embodiments of the present disclosure, the method 1100 of analyzing the medical data may further include the following operations.

A test report is generated according to the second gene mutation information and the second survival information.

According to embodiments of the present disclosure, a test report template may be designed using Adobe Acrobat DC software. The test report template may be determined according to actual service needs and is not limited here.

According to embodiments of the present disclosure, when an object logs in to a medical aided diagnosis application, it is possible to acquire a personal information of the object input into a medical data information input box, and obtain a test report according to an object information, so that a result may be saved or shared by the object. The medical data information input box may be displayed in response to a detection of at least one of a floating window and an on-site message of the medical aided diagnostic application being triggered. In addition, when a change in the personal information of the object is detected, it is possible to automatically update a test report content and send a prompt message to the object by at least one of device pop-up window, short message or other prompt messages.

Figure 12:
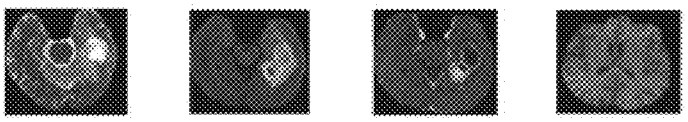
FIG. 12 schematically shows a schematic diagram of an example of generating a test report according to an embodiment of the present disclosure.

FIG. 12 schematically shows a schematic diagram of an example of generating a test report according to an embodiment of the present disclosure.

As shown in FIG. 12, the test report template may include at least one of a basic information, a basic mutation information prediction result, a survival information prediction result, or an MRI sampling. The basic information may include name, age, gender, height, weight, and glioma grade. A prediction item of the basic mutation information prediction result may include IDH, 1p/19q, TERT, and MGMT. The survival information prediction result may include an estimated survival time of the patient. The MRI sampling may include examples of medical images in different modalities.

According to embodiments of the present disclosure, if a test report needs to be generated, it is possible to select a test report template to generate a test report using itext of Spring Boot. The basic information of the patient may be filled into the test report template using itext of Spring Boot. As shown in FIG. 12, the basic information in the test report may include "Name: Zhang San, Age: 59, Gender: Male, Height: 176 CM, Weight: 78 KG, and Glioma Grade: G4".

According to embodiments of the present disclosure, a gene mutation information prediction model may be called using a backend JAVA program to process input medical image data to obtain a gene mutation information prediction result. A survival information prediction model may be called using the backend JAVA program to process input medical text data and medical image data to obtain a survival information prediction result.

According to embodiments of the present disclosure, after the gene mutation information prediction result and the survival information prediction result are obtained, the medical image data may be filled into an MRI sampling map in the test report template using itext of Spring Boot. As shown in FIG. 12, the MRI sampling map in the test report may include "T1, T2, T1CE and FLAIR".

According to embodiments of the present disclosure, the gene mutation information prediction result may be filled into the test report template using itext of Spring Boot. As shown in FIG. 12, the gene mutation information prediction result in the test report may include "IDH: no mutation (wild-type), 1p/19q: no deletion, TERT: no mutation (wild-type), and MGMT: no methylation".

According to embodiments of the present disclosure, the survival information prediction result may be filled into the test report template using itext of Spring Boot. As shown in FIG. 12, the survival information prediction result in the test report may include "patient survival >5 years".

According to embodiments of the present disclosure, after the gene mutation information prediction result and the survival information prediction result are obtained, it is possible to query a biological database using a backend JAVA program, and display an annotation information of molecular detection result in the template test report using itext of Spring Boot.

According to embodiments of the present disclosure, after the test report template is filled, a test report may be output. A file format of the test report may be determined according to actual service needs and is not limited here. For example, the file format of the test report may include JPG (Joint Photographic Experts Group), TIFF (Tag Image File Format), PNG (Portable Network Graphics), PDF (Portable Document Format), and GIF (Graphics Interchange Format), etc.

According to embodiments of the present disclosure, the test report may be applied to fields such as glioma molecular typing, survival prediction, surgical resection region guidance, and auxiliary guidance for clinical medication. In the field of glioma molecular typing, it is possible to determine IDH mutation information, chromosome 1p/19q co-deletion mutation information, TERT mutation information and MGMT promoter methylation mutation information based on the test report. In the field of survival prediction, it is possible to determine the patient survival based on the test report. In the field of surgical resection region guidance, it is possible to determine gene mutation information according to the test report and further determine a molecular pathological type of glioma, so as to assist a doctor in making a decision on whether to adopt an aggressive or conservative resection method in a surgical strategy. In the field of auxiliary guidance for clinical medication, it is possible to guide patient medication according to gene mutation information.

According to embodiments of the present disclosure, obtaining the model parameters in the third feature extraction network, the fourth feature extraction network, the third classification network and the fourth classification network through joint training may include the following operations.

Third sample data is acquired. The third sample data includes third sample medical image data, a second sample gene mutation label information corresponding to the third sample medical image data, second sample medical data, and a second sample survival label information corresponding to the second sample medical data. The second medical data includes second sample medical text data and the third sample medical image data. The third sample medical image data is input into a third feature extraction network and a third classifier to obtain a second sample gene mutation prediction information corresponding to the third sample medical data. The second sample gene mutation prediction information and the second sample gene mutation label information are input into a third loss function to obtain a third loss function value. The second sample medical data is input into a fourth feature extraction network and a fourth classifier to obtain a second sample survival prediction information corresponding to the second sample medical data. The second sample survival prediction information and the second sample survival label information are input into a fourth loss function to obtain a fourth loss function value. The model parameters of the third feature extraction network, the fourth feature extraction network, the third classification network and the fourth classification network are adjusted according to the third loss function value and the fourth loss function value.

According to embodiments of the present disclosure, adjusting the model parameters of the third feature extraction network, the fourth feature extraction network, the third classification network and the fourth classification network according to the third loss function value and the fourth loss function value may include the following operations.

The model parameters of the third feature extraction network and the third classifier are adjusted according to the third loss function value. While keeping the model parameters of the third feature extraction network and the third classifier unchanged, the model parameters of the fourth feature extraction network and the fourth classifier are adjusted according to the fourth loss function value.

According to embodiments of the present disclosure, the third sample medical image data may be processed using the third feature extraction network and the third classifier to obtain a second sample gene mutation prediction information corresponding to the third sample medical image data. The second sample survival prediction information and the second sample gene mutation label information may be input into a third loss function to obtain a third loss function value. The model parameters of the third feature extraction network and the third classifier may be adjusted according to the third loss function value until a predetermined condition is met. For example, the model parameters of the third feature extraction network and the third classifier may be adjusted according to a back propagation algorithm or a random gradient descent algorithm until the predetermined condition is met.

According to embodiments of the present disclosure, the second sample medical data may be processed using a fourth feature extraction network and a fourth classifier to obtain a second sample survival prediction information corresponding to the third sample medical data. The second sample survival prediction information and the second sample survival label information may be input into a fourth loss function to obtain a fourth loss function value. While keeping the model parameters of the third feature extraction network and the third classifier unchanged, the model parameters of the fourth feature extraction network and the fourth classifier may be adjusted according to the fourth loss function value until a predetermined condition is met. For example, the model parameters of the fourth feature extraction network and the fourth classifier may be adjusted according to a back propagation algorithm or a random gradient descent algorithm until the predetermined condition is met.

Figure 13A:
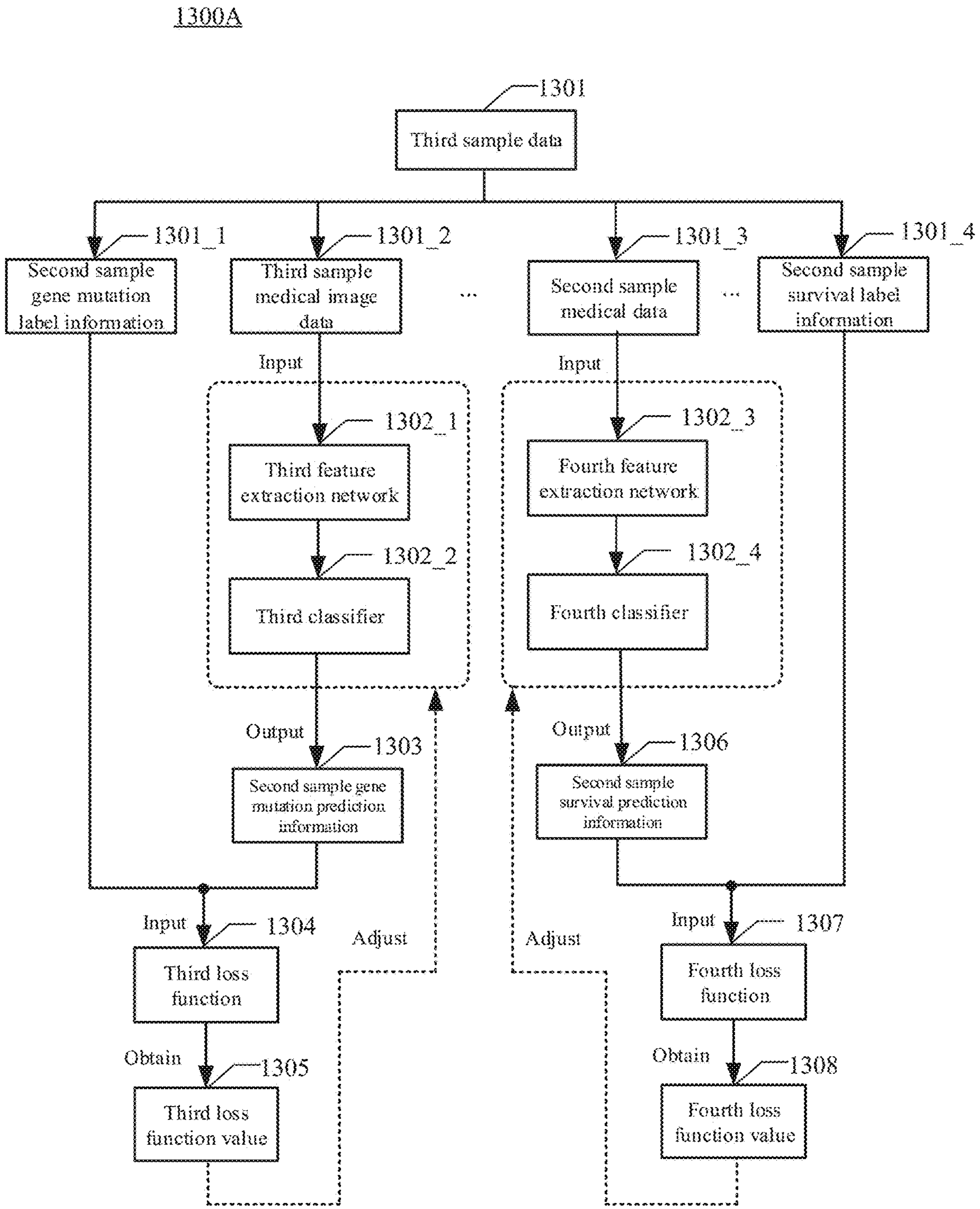
FIG. 13A schematically shows a schematic diagram of an example of adjusting model parameters of a third feature extraction network, a fourth feature extraction network, a third classification network and a fourth classification network based on a third loss function value and a fourth loss function value according to an embodiment of the present disclosure.

FIG. 13A schematically shows a schematic diagram of an example of adjusting model parameters of a third feature extraction network, a fourth feature extraction network, a third classification network and a fourth classification network based on a third loss function value and a fourth loss function value according to an embodiment of the present disclosure.

As shown in FIG. 13A, third sample data 1301 may be acquired during the joint training process. The third sample data 1301 may include third sample medical image data 1301_2, a second sample gene mutation label information 1301_1 corresponding to the third sample medical image data 13012, second sample medical data 1301_3, and a second sample survival label information 1301_4 corresponding to the second sample medical data 1301_3.

The third sample medical image data 1301_2 may be processed using a third feature extraction network 1302_1 and a third classifier 1302_2 to obtain a second sample gene mutation prediction information 1303 corresponding to the third sample medical image data 1301_2. The second sample gene mutation prediction information 1303 and the second sample gene mutation label information 1301_1 may be input into a third loss function 1304 to obtain a third loss function value 1305.

The second sample medical data 13013 may be processed using a fourth feature extraction network 1302_3 and a fourth classifier 1302_4 to obtain a second sample survival prediction information 1306 corresponding to the second sample medical data 1301_3. The second sample survival prediction information 1306 and the second sample survival label information 13014 may be input into a fourth loss function 1307 to obtain a fourth loss function value 1308.

Model parameters of the third feature extraction network 1302_1 and the third classifier 1302_2 may be adjusted according to the third loss function value 1305. While keeping the model parameters of the third feature extraction network 1302_1 and the third classifier 1302_2 unchanged, the model parameters of the fourth feature extraction network 1302_3 and the fourth classifier 1302_4 may be adjusted according to the fourth loss function value 1308.

According to embodiments of the present disclosure, adjusting the model parameters of the third feature extraction network, the fourth feature extraction network, the third classification network and the fourth classification network according to the third loss function value and the fourth loss function value may include the following operations.

A total loss function value is determined according to the third loss function value and the fourth loss function value. The model parameters of the third feature extraction network, the fourth feature extraction network, the third classification network and the fourth classification network are adjusted according to the total loss function value.

According to embodiments of the present disclosure, the total loss function value may be determined according to the third loss function value and the fourth loss function value. The model parameters of the third feature extraction network, the fourth feature extraction network, the third classification network and the fourth classification network may be adjusted according to the total loss function value until a predetermined condition is met. For example, the model parameters of the third feature extraction network, the fourth feature extraction network, the third classification network and the fourth classification network may be adjusted according to a back propagation algorithm or a random gradient descent algorithm until the predetermined condition is met.

According to embodiments of the present disclosure, a specific method of determining the total loss function value according to the third loss function value and the fourth loss function value may be determined according to actual service needs and is not limited here. For example, the total loss function value may be determined according to a cumulative value of the third loss function value and the fourth loss function value. Alternatively, a calculation method for determining the total loss function value according to the third loss function value and the fourth loss function value may be shown as Equation (10).

$$L_{Mutil\_task\_loss} = \beta L_{GMS} + (1-\beta)L_{SP} \quad (10)$$

where β may represent an adjustment weight of the total loss function, $0 \le \beta \le 1$, $L_{GMS}$ may represent the third loss function, $L_{SP}$ may represent the fourth loss function, and $L_{Mutil\_task\_loss}$ may represent the total loss function.

According to embodiments of the present disclosure, model performance of the third feature extraction network, the fourth feature extraction network, the third classification network and the fourth classification network may be tested using validation sample data to obtain a performance test result. For example, validation sample medical image data may be processed using the third feature extraction network and the third classifier to obtain a first state classification result. The validation sample medical data may be processed using the fourth feature extraction network and the fourth classifier to obtain a second state classification result. A state classification result may be determined according to the first state classification result and the second state classification result. The performance test result may be determined according to the state classification result.

According to embodiments of the present disclosure, after the performance test result is obtained, it may be determined whether the performance test result meets a predetermined performance condition. When it is determined that the performance test result meets the predetermined performance condition, the joint training operation may end. When it is determined that the performance test result does not meet the predetermined performance condition, an adjustment may be performed on model hyper-parameters corresponding to the third feature extraction network, the fourth feature extraction network, the third classification network and the fourth classification network. The third feature extraction network and the third classifier may be retrained using the validation sample medical image data and the sample gene mutation label information based on the adjusted model hyper-parameters, so as to obtain a new third feature extraction network and a new third classifier. On this basis, the fourth feature extraction network and the fourth classifier may be retrained using the validation sample medical data and the sample survival label information to obtain a new fourth feature extraction network and a new fourth classifier. The above-mentioned operations are repeatedly performed until the performance test result meets the predetermined performance condition.

According to embodiments of the present disclosure, the model performance may be represented by a model performance evaluation value. The performance test result includes a model performance evaluation value. The model performance evaluation value may include at least one of precision, recall rate, accuracy, error rate, or F-function value. The predetermined performance condition may refer to that the performance evaluation value is greater than or equal to a predetermined performance evaluation threshold. The predetermined performance evaluation threshold may be determined according to actual service needs and is not limited here. The model hyper-parameter may include at least one of a learning rate and the number of layers of the deep learning model.

Figure 13B:
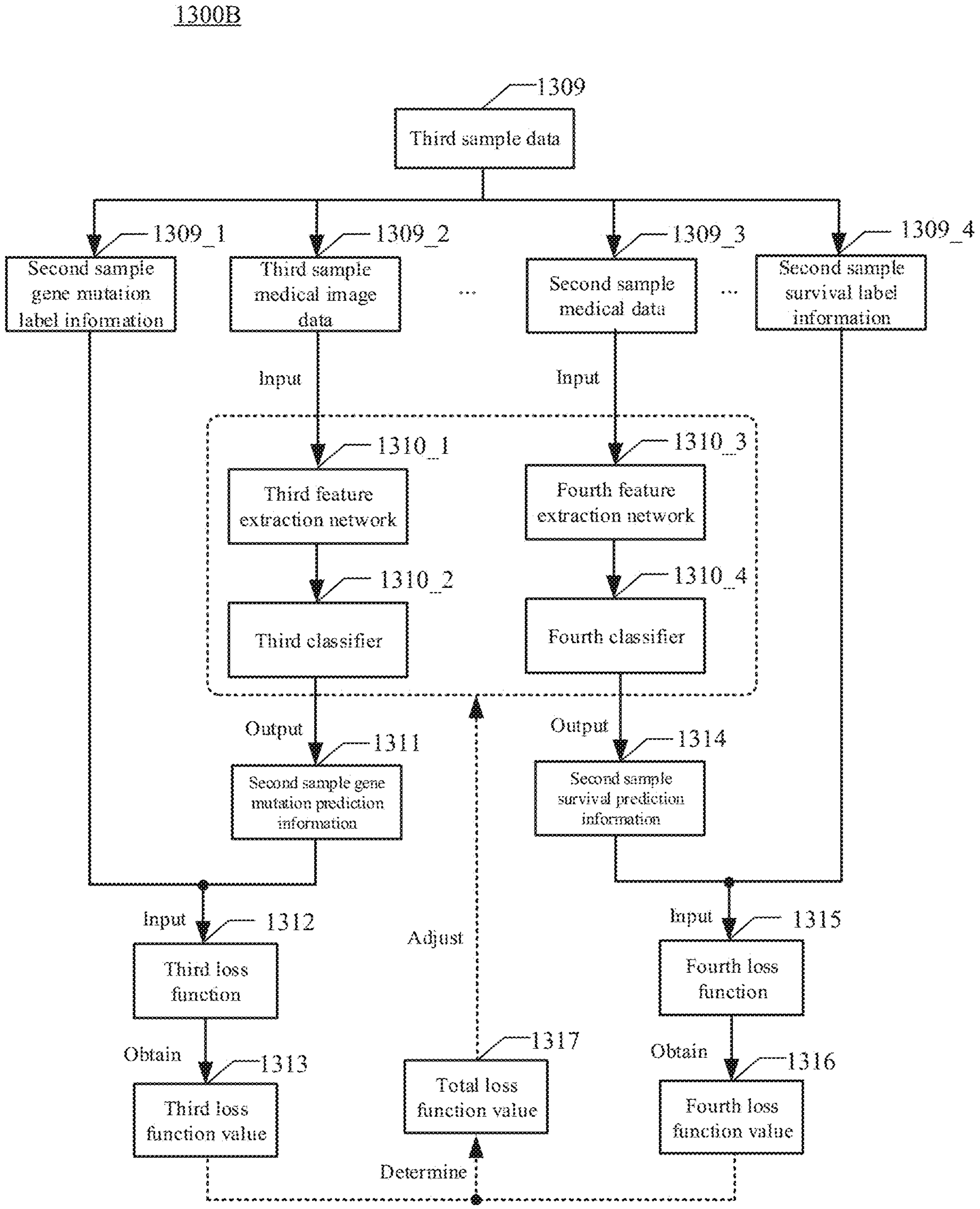
FIG. 13B schematically shows a schematic diagram of an example of adjusting model parameters of a third feature extraction network, a fourth feature extraction network, a third classification network and a fourth classification network based on a third loss function value and a fourth loss function value according to another embodiment of the present disclosure.

FIG. 13B schematically shows a schematic diagram of an example of adjusting model parameters of a third feature extraction network, a fourth feature extraction network, a third classification network and a fourth classification network based on a third loss function value and a fourth loss function value according to another embodiment of the present disclosure.

As shown in FIG. 13B, third sample data 1309 may be acquired during the joint training process. The third sample data 1309 may include third sample medical image data 1309_2, a second sample gene mutation label information 1309_1 corresponding to the third sample medical image data 13092, second sample medical data 1309_3, and a second sample survival label information 1309_4 corresponding to the second sample medical data 1309_3.

The third sample medical image data 1309_2 may be processed using a third feature extraction network 1310_1 and a third classifier 1310_2 to obtain a second sample gene mutation prediction information 1311 corresponding to the third sample medical image data 1309_2. The second sample gene mutation prediction information 1311 and the second sample gene mutation label information 1309_1 may be input into a third loss function 1312 to obtain a third loss function value 1313.

The second sample medical data 13093 may be processed using a fourth feature extraction network 1310_3 and a fourth classifier 1310_4 to obtain a second sample survival prediction information 1314 corresponding to the second sample medical data 1309_3. The second sample survival prediction information 1314 and the second sample survival label information 13094 may be input into a fourth loss function 1315 to obtain a fourth loss function value 1316.

A total loss function value 1317 may be determined according to the third loss function value 1313 and the fourth loss function value 1316. The model parameters of the third feature extraction network 1310, the third classifier 13102, the fourth feature extraction network 1302_3 and the fourth classifier 1302_4 may be adjusted according to the total loss function value 1317.

The above are just exemplary embodiments. The present disclosure is not limited to the above and may further include other methods of analyzing medical data known in the art, as long as the medical data may be analyzed.

Figure 14:
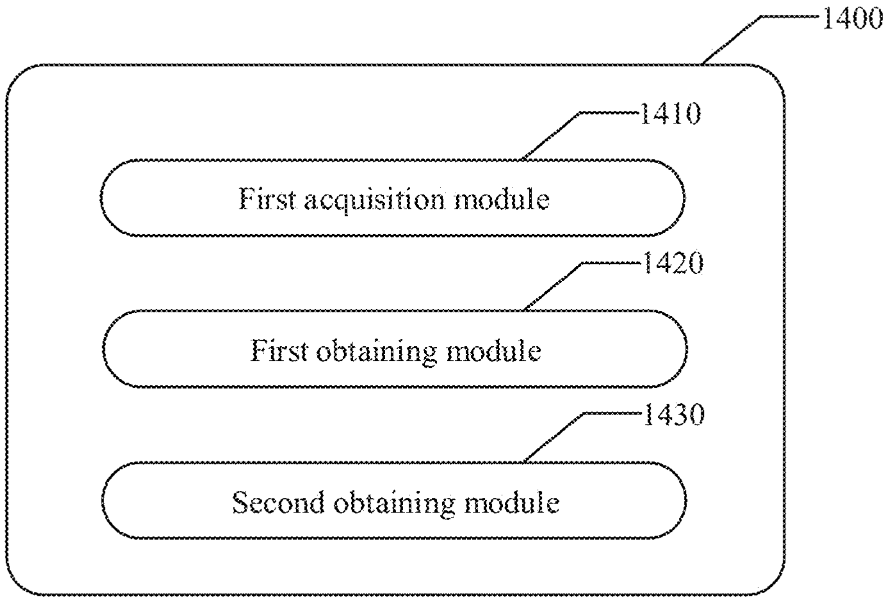
FIG. 14 schematically shows a block diagram of an apparatus of processing medical data according to an embodiment of the present disclosure.

FIG. 14 schematically shows a block diagram of an apparatus of processing medical data according to an embodiment of the present disclosure.

As shown in FIG. 14, an apparatus 1400 of processing medical data may include a first acquisition module 1410, a first obtaining module 1420, and a second obtaining module 1430.

The first acquisition module 1410 is used to acquire first medical image data.

The first obtaining module 1420 is used to input the first medical image data into a first feature extraction network to obtain a first image feature.

The second obtaining module 1430 is used to obtain a first gene mutation information according to the first image feature.

According to embodiments of the present disclosure, the first feature extraction network includes a first feature extraction module. The first feature extraction module is used to: determine a first image query matrix and a first image key matrix according to the first medical image data; determine a first image weight matrix according to the first image query matrix and the first image key matrix, where the first image weight matrix represents a correlation information between each two first medical images in the first medical image data; and determine the first image feature according to the first image weight matrix and the first medical image data.

According to embodiments of the present disclosure, the first medical image data includes a plurality of kinds of mono-modality medical image data, and the first feature extraction network includes a plurality of first feature extraction sub-networks respectively corresponding to the plurality of kinds of mono-modality medical image data.

According to embodiments of the present disclosure, the first obtaining module 1420 may include a first obtaining unit.

The first obtaining unit is used to input the plurality of kinds of mono-modality medical image data respectively into their respective first feature extraction sub-networks, so as to obtain a plurality of mono-modality image features.

According to embodiments of the present disclosure, the second obtaining module 1430 may include a second obtaining unit and a third obtaining unit.

The second obtaining unit is used to concatenate the plurality of mono-modality image features to obtain a concatenated image feature.

The third obtaining unit is used to input the concatenated image feature into a first classification network to obtain the first gene mutation information.

According to embodiments of the present disclosure, the first medical image data include multi-modality medical image data, and the first feature extraction network includes a plurality of first feature extraction sub-networks.

According to embodiments of the present disclosure, the first obtaining module 1420 may further include a fourth obtaining unit.

The fourth obtaining unit is used to input the multi-modality medical image data into the plurality of first feature extraction sub-networks to obtain a plurality of multi-modality image features.

According to embodiments of the present disclosure, the second obtaining module 1430 may further include a fifth obtaining unit and a sixth obtaining unit.

The fifth obtaining unit is used to input the plurality of multi-modality image features into a second classification network to obtain a plurality of predictions for single gene mutation types.

The sixth obtaining unit is used to combine the plurality of predictions for single gene mutation types to obtain the first gene mutation information.

According to embodiments of the present disclosure, the second classification network includes a plurality of second classification sub-networks respectively corresponding to the plurality of multi-modality image features.

According to embodiments of the present disclosure, the fifth obtaining unit may include a first obtaining sub-unit.

The first obtaining sub-unit is used to input the plurality of multi-modality image features respectively into their respective second classification sub-networks, so as to obtain the plurality of predictions for single gene mutation types.

According to embodiments of the present disclosure, the second classification sub-network includes at least one selected from: an isocitrate dehydrogenase mutation classification network, a chromosome 1p/19q classification network, a telomerase reverse transcriptase promoter classification network, or an $O^6$-methylguanine-DNA methyltransferase classification network.

According to embodiments of the present disclosure, the plurality of first feature extraction sub-networks share model parameters with each other.

According to embodiments of the present disclosure, the first medical image data includes a plurality of first medical images, and the first feature extraction network further includes a second feature extraction module.

According to embodiments of the present disclosure, the apparatus 1400 of processing the medical data may further include a third obtaining module.

The third obtaining module is used to input the plurality of first medical images into the second feature extraction module to obtain a first temporal image feature. The first temporal image feature represents a temporal relationship between the plurality of first medical images.

According to embodiments of the present disclosure, the determining a first image query matrix and a first image key matrix according to the first medical image data may include: inputting the first temporal image feature into the first feature extraction module to obtain the first image query matrix and the first image key matrix.

According to embodiments of the present disclosure, the first feature extraction network further includes a third feature extraction module, and the third feature extraction module includes a first maximum pooling layer, a first residual unit, a first down-sampling unit, and a first average pooling layer.

According to embodiments of the present disclosure, the apparatus 1400 of processing the medical data may further include a fourth obtaining module.

The fourth obtaining module is used to input the plurality of first medical images into the third feature extraction module to obtain a plurality of first intermediate image features.

According to embodiments of the present disclosure, the third obtaining module may include a seventh obtaining unit.

The seventh obtaining unit is used to input the plurality of first intermediate image features into the second feature extraction module to obtain the first temporal image feature.

According to embodiments of the present disclosure, the determining the first image feature according to the first image weight matrix and the first medical image data may include: obtaining a first image value matrix according to the first medical image data; and obtaining the first image feature according to the first image weight matrix and the first image value matrix.

According to embodiments of the present disclosure, the apparatus 1400 of processing the medical data may further include a fourth obtaining module.

The fourth obtaining module is used to obtain an image type information of the first medical image data according to device type conversion standard data corresponding to the first medical image data.

According to embodiments of the present disclosure, the apparatus 1400 of processing the medical data may further include a fifth obtaining module and a sixth obtaining module. The fifth obtaining module is used to determine the image type information of the first medical image data according to medical image metadata corresponding to the first medical image data, in response to failing to determine the image type information of the first medical image data according to the device type conversion standard data corresponding to the first medical image data.

The sixth obtaining module is used to obtain the image type information according to the first medical image data and the medical image metadata, in response to failing to determine the image type information according to the device type conversion standard data and failing to determine the image type information according to the medical image metadata.

According to embodiments of the present disclosure, the apparatus 1400 of processing the medical data may further include a seventh obtaining module.

The seventh obtaining module is used to obtain the medical image metadata according to the first medical image data.

According to embodiments of the present disclosure, the plurality of mono-modality medical image data includes at least one selected from: mono-modality medical image data corresponding to an anatomical structure, mono-modality medical image data corresponding to a lesion site, mono-modality medical image data corresponding to an edema region, or mono-modality medical image data corresponding to a contrast enhancement.

According to embodiments of the present disclosure, the apparatus 1400 of processing the medical data may further include a second acquisition module, an eighth obtaining module, a ninth obtaining module, and a first adjustment module.

The second acquisition module is used to acquire first sample data. The first sample data includes first sample medical image data and a first sample gene mutation label information corresponding to the first sample medical image data.

The eighth obtaining module is used to input the first sample medical image data into the first feature extraction network and a classification network to obtain a first sample gene mutation prediction information corresponding to the first sample medical image data.

The ninth obtaining module is used to input the first sample gene mutation prediction information and the first sample gene mutation label information into a first loss function to obtain a first loss function value.

The first adjustment module is used to adjust a model parameter of the first feature extraction network and a model parameter of the classification network according to the first loss function value.

Figure 15:
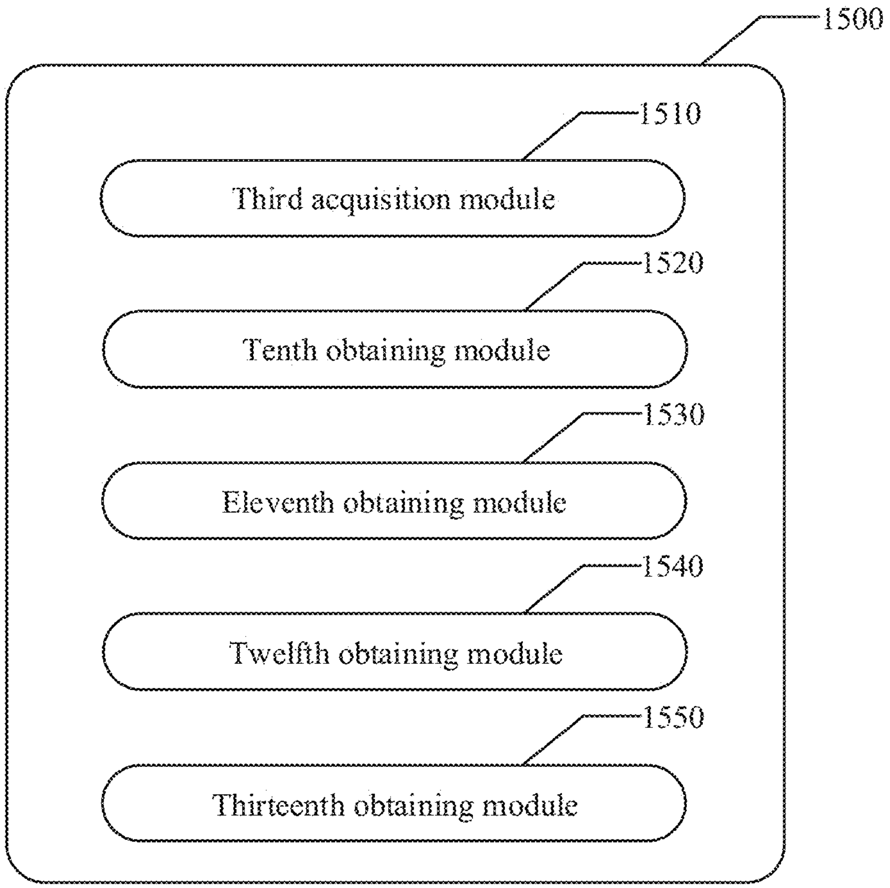
FIG. 15 schematically shows a block diagram of an apparatus of processing medical data according to an embodiment of the present disclosure.

FIG. 15 schematically shows a block diagram of an apparatus of processing medical data according to embodiments of the present disclosure.

As shown in FIG. 15, an apparatus 1500 of processing medical data may include a third acquisition module 1510, a tenth obtaining module 1520, an eleventh obtaining module 1530, a twelfth obtaining module 1540, and a thirteenth obtaining module 1550.

The third acquisition module 1510 is used to acquire first medical text data and second medical image data.

The tenth obtaining module 1520 is used to obtain a second image feature according to the second medical image data.

The eleventh obtaining module 1530 is used to input the first medical text data into the second feature extraction network to obtain a first text feature.

The twelfth obtaining module 1540 is used to fuse the second image feature with the first text feature to obtain a first fusion feature.

The thirteenth obtaining module 1550 is used to obtain a first survival information according to the first fusion feature.

According to embodiments of the present disclosure, the eleventh obtaining module 1530 may include an eighth obtaining unit, a ninth obtaining unit, a tenth obtaining unit, and an eleventh obtaining unit.

The eighth obtaining unit is used to encode the first medical text data to obtain a first medical text vector.

The ninth obtaining unit is used to input the first medical text vector into a first encoder to obtain a first hidden vector.

The tenth obtaining unit is used to input the first hidden vector into a first decoder to obtain a first decoded vector.

The eleventh obtaining unit is used to obtain the first text feature according to the first hidden vector and the first decoded vector.

According to embodiments of the present disclosure, the twelfth obtaining module 1540 may include a first determination unit, a second determination unit, a third determination unit, a fourth determination unit, a twelfth obtaining unit, a thirteenth obtaining unit, and a fourteenth obtaining unit.

The first determination unit is used to determine a second image query matrix and a second image key matrix according to the second medical image data.

The second determination unit is used to determine a text query matrix and a text key matrix according to the first medical text data.

The third determination unit is used to determine a first fusion weight matrix according to the second image query matrix and the text key matrix.

The fourth determination unit is used to determine a second fusion weight matrix according to the text query matrix and the second image key matrix.

The twelfth obtaining unit is used to obtain a first output feature vector according to the first fusion weight matrix and a text value matrix, where the text value matrix is obtained according to the first medical text data.

The thirteenth obtaining unit is used to obtain a second output feature vector according to the second fusion weight matrix and the second image value matrix, where the second image value matrix is obtained according to the second medical image data.

The fourteenth obtaining unit is used to obtain the first fusion feature according to the first output feature vector and the second output feature vector.

According to embodiments of the present disclosure, a fusion deep learning model includes the second feature extraction network.

According to embodiments of the present disclosure, the apparatus 1500 of processing the medical data may further include a fourth acquisition module, a fourteenth obtaining module, a fifteenth obtaining module, and a second adjustment module.

The fourth acquisition module is used to acquire second sample data. The second sample data includes first sample medical data and a first sample survival label information corresponding to the first sample medical data, and the first sample medical data includes first sample medical text data and second sample medical image data.

The fourteenth obtaining module is used to input the first sample medical data into the first fusion deep learning network to obtain a first sample survival prediction information corresponding to the first sample medical data.

The fifteenth obtaining module is used to input the first sample survival prediction information and the first sample survival label information into a second loss function to obtain a second loss function value.

The second adjustment module is used to adjust a model parameter of the first fusion deep learning network according to the second loss function value.

Figure 16:
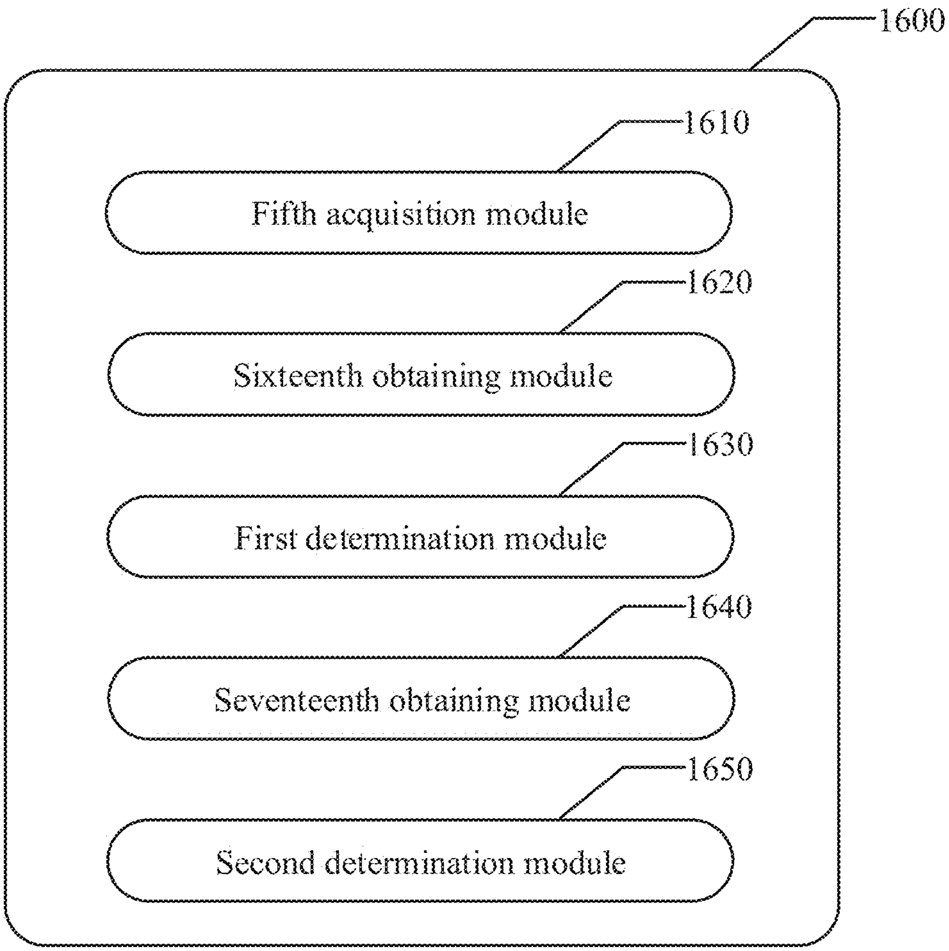
FIG. 16 schematically shows a block diagram of an apparatus of analyzing medical data according to an embodiment of the present disclosure.

FIG. 16 schematically shows a block diagram of an apparatus of analyzing medical data according to an embodiment of the present disclosure.

As shown in FIG. 16, an apparatus 1600 of analyzing medical data may include a fifth acquisition module 1610, a sixteenth obtaining module 1620, a first determination module 1630, a seventeenth obtaining module 1640, and a second determination module 1650.

The fifth acquisition module 1610 is used to acquire second medical text data and third medical image data.

The sixteenth obtaining module 1620 is used to input the third medical image data into a third feature extraction network to obtain a third image feature.

The first determination module 1630 is used to determine a second gene mutation information according to the third image feature.

The seventeenth obtaining module 1640 is used to input the second medical text data into a fourth feature extraction network to obtain a second text feature.

The second determination module 1650 is used to determine a second survival information according to a fusion feature obtained from the third image feature and the second text feature.

According to embodiments of the present disclosure, the third feature extraction network includes a fourth feature extraction module. The fourth feature extraction module is used to: determine a third image query matrix and a third image key matrix according to the third medical image data; determine a third image weight matrix according to the third image query matrix and the third image key matrix, where the third image weight matrix represents a correlation information between each two third medical images in the third medical image data; and determine the third image feature according to the third image weight matrix and the third medical image data.

According to embodiments of the present disclosure, the apparatus 1600 of analyzing the medical data may further include a generation module.

The generation module is used to generate a test report according to the second gene mutation information and the second survival information.

According to embodiments of the present disclosure, the third medical image data includes a plurality of third medical images, and the third feature extraction network further includes a fifth feature extraction module.

According to embodiments of the present disclosure, the apparatus 1600 of analyzing the medical data may further include an eighteenth obtaining module.

The eighteenth obtaining module is used to input the plurality of third medical images into the fifth feature extraction module to obtain a second temporal image feature. The second temporal image feature represents a temporal relationship between the plurality of third medical images.

According to embodiments of the present disclosure, the determining a third image query matrix and a third image key matrix according to the third medical image data includes: inputting the second temporal image feature into the fourth feature extraction module to obtain the third image query matrix and the third image key matrix.

According to embodiments of the present disclosure, the third feature extraction network further includes a sixth feature extraction module, and the sixth feature extraction module includes a second maximum pooling layer, a second residual unit, a second down-sampling unit, and a second average pooling layer.

According to embodiments of the present disclosure, the apparatus 1600 of analyzing the medical data may further include a nineteenth obtaining module.

The nineteenth obtaining module is used to input the plurality of third medical images into the sixth feature extraction module to obtain a second intermediate image feature.

According to embodiments of the present disclosure, a twentieth obtaining module may include a fifteenth obtaining unit.

The fifteenth obtaining unit is used to input the second intermediate image feature into the fifth feature extraction module to obtain the second temporal image feature.

According to embodiments of the present disclosure, the determining the third image feature according to the third image weight matrix and the third medical image data may include: obtaining a third image value matrix according to the third medical image data; and obtaining the third image feature according to the third image weight matrix and the third image value matrix.

According to embodiments of the present disclosure, the seventeenth obtaining module 1640 may include a sixteenth obtaining unit, a seventeenth obtaining unit, an eighteenth obtaining unit, and a nineteenth obtaining unit.

The sixteenth obtaining unit is used to encode the second medical text data to obtain a second medical text vector.

The seventeenth obtaining unit is used to input the second medical text vector into a second encoder to obtain a second hidden vector.

The eighteenth obtaining unit is used to input the second hidden vector into a second decoder to obtain a second decoded vector.

The nineteenth obtaining unit is used to obtain the second text feature according to the second hidden vector and the second decoded vector.

According to embodiments of the present disclosure, the first determination module 1630 may include a twentieth obtaining unit.

The twentieth obtaining unit is used to input the third image feature into a third classification network to obtain the second gene mutation information.

According to embodiments of the present disclosure, the second determination module 1650 may include a twenty-first obtaining unit.

The twenty-first obtaining unit is used to input the fusion feature obtained from the third image feature and the second text feature into a fourth classification network to obtain the second survival information.

According to embodiments of the present disclosure, a model parameter of the third feature extraction network, a model parameter of the fourth feature extraction network, a model parameter of the third classification network and a model parameter of the fourth classification network are obtained by joint training.

According to embodiments of the present disclosure, obtaining the model parameter of the third feature extraction network, the model parameter of the fourth feature extraction network, the model parameter of the third classification network and the model parameter of the fourth classification network by joint training may include a sixth acquisition module, an eighteenth obtaining module, a nineteenth obtaining module, a twentieth obtaining module, a twenty-first obtaining module, and a third adjustment module.

The sixth acquisition module is used to acquire third sample data. The third sample data includes third sample medical image data, a second sample gene mutation label information corresponding to the third sample medical image data, second sample medical data, and a second sample survival label information corresponding to the second sample medical data. The second sample medical data includes second sample medical text data and third sample medical image data.

The eighteenth obtaining module is used to input the third sample medical image data into the third feature extraction network and the third classifier to obtain a second sample gene mutation prediction information corresponding to the third sample medical data.

The nineteenth obtaining module is used to input the second sample gene mutation prediction information and the second sample gene mutation label information into a third loss function to obtain a third loss function value.

The twentieth obtaining module is used to input the second sample medical data into the fourth feature extraction network and the fourth classifier to obtain a second sample survival prediction information corresponding to the second sample medical data.

The twenty-first obtaining module is used to input the second sample survival prediction information and the second sample survival label information into a fourth loss function to obtain a fourth loss function value.

The third adjustment module is used to adjust the model parameter of the third feature extraction network, the model parameter of the fourth feature extraction network, the model parameter of the third classification network, and the model parameter of the fourth classification network according to the third loss function value and the fourth loss function value.

According to embodiments of the present disclosure, the third adjustment module may include a first adjustment unit and a second adjustment unit.

The first adjustment unit is used to adjust the model parameter of the third feature extraction network and the model parameter of the third classifier according to the third loss function value.

The second adjustment unit is used to adjust the model parameter of the fourth feature extraction network and the model parameter of the fourth classifier according to the fourth loss function value, while keeping the model parameter of the third feature extraction network and the model parameter of the third classifier unchanged.

According to embodiments of the present disclosure, the third adjustment module may include a fifth determination unit and a third adjustment unit.

The fifth determination unit is used to determine a total loss function value according to the third loss function value and the fourth loss function value.

The third adjustment unit is used to adjust the model parameter of the third feature extraction network, the model parameter of the fourth feature extraction network, the model parameter of the third classification network, and the model parameter of the fourth classification network according to the total loss function value.

Any number of the modules, sub-modules, units and sub-units according to the embodiments of the present disclosure, or at least part of functions of any number of them may be implemented in one module. Any one or more of the modules, sub-modules, units and sub-units according to embodiments of the present disclosure may be split into a plurality of modules for implementation. Any one or more of the modules, sub-modules, units and sub-units according to embodiments of the present disclosure may be implemented at least partially as a hardware circuit, such as a field programmable gate array (FPGA), a programmable logic array (PLA), a system on a chip, a system on a substrate, a system on a package, an Application Specific Integrated Circuit (ASIC), or may be implemented by hardware or firmware in any other reasonable manner of integrating or encapsulating the circuit, or may be implemented by any one of three implementation modes of software, hardware and firmware or an appropriate combination thereof. Alternatively, one or more of the modules, sub-modules, units and sub-units according to embodiments of the present disclosure may be at least partially implemented as a computer program module that, when executed, performs the corresponding functions.

For example, any number of the first acquisition module 1410, the first obtaining module 1420 and the second obtaining module 1430, or the third acquisition module 1510, the tenth obtaining module 1520, the eleventh obtaining module 1530, a twelfth obtaining module 1540 and the thirteenth obtaining unit 1550, or the fifth acquisition module 1610, the sixteenth obtaining module 1620, the first determination module 1630, the seventeenth obtaining module 1640 and the second determination module 1650 may be combined into one module/unit/sub-unit for implementation, or any one of the modules/units/sub-units may be divided into a plurality of modules/units/sub-units. Alternatively, at least part of the functions of one or more of these modules/units/sub-units may be combined with at least part of the functions of other modules/units/sub-units and implemented in one module/unit/sub-unit. According to embodiments of the present disclosure, at least one of the first acquisition module 1410, the first obtaining module 1420 and the second obtaining module 1430, or the third acquisition module 1510, the tenth obtaining module 1520, the eleventh obtaining module 1530, a twelfth obtaining module 1540 and the thirteenth obtaining unit 1550, or the fifth acquisition module 1610, the sixteenth obtaining module 1620, the first determination module 1630, the seventeenth obtaining module 1640 and the second determination module 1650 may be implemented at least partially as a hardware circuit, such as a field programmable gate array (FPGA), a programmable logic array (PLA), a system on a chip, a system on a substrate, a system on a package, an Application Specific Integrated Circuit (ASIC), or may be implemented by hardware or firmware in any other reasonable manner of integrating or encapsulating the circuit, or may be implemented by any one of the three implementation modes of software, hardware and firmware or an appropriate combination thereof. Alternatively, at least one of the first acquisition module 1410, the first obtaining module 1420 and the second obtaining module 1430, or the third acquisition module 1510, the tenth obtaining module 1520, the eleventh obtaining module 1530, a twelfth obtaining module 1540 and the thirteenth obtaining unit 1550, or the fifth acquisition module 1610, the sixteenth obtaining module 1620, the first determination module 1630, the seventeenth obtaining module 1640 and the second determination module 1650 may be at least partially implemented as a computer program module that may perform corresponding functions when executed.

It should be noted that a part for the apparatus of processing the medical data in embodiments of the present disclosure corresponds to a part for the method of processing the medical data in embodiments of the present disclosure. For the descriptions of the apparatus of processing the medical data, reference may be made to the method of processing the medical data, and details will not be repeated here. A part for the apparatus of analyzing the medical data in embodiments of the present disclosure corresponds to a part for the method of analyzing the medical data in embodiments of the present disclosure. For the descriptions of the apparatus of analyzing the medical data, reference may be made to the method of analyzing the medical data, and details will not be repeated here.

Figure 17:
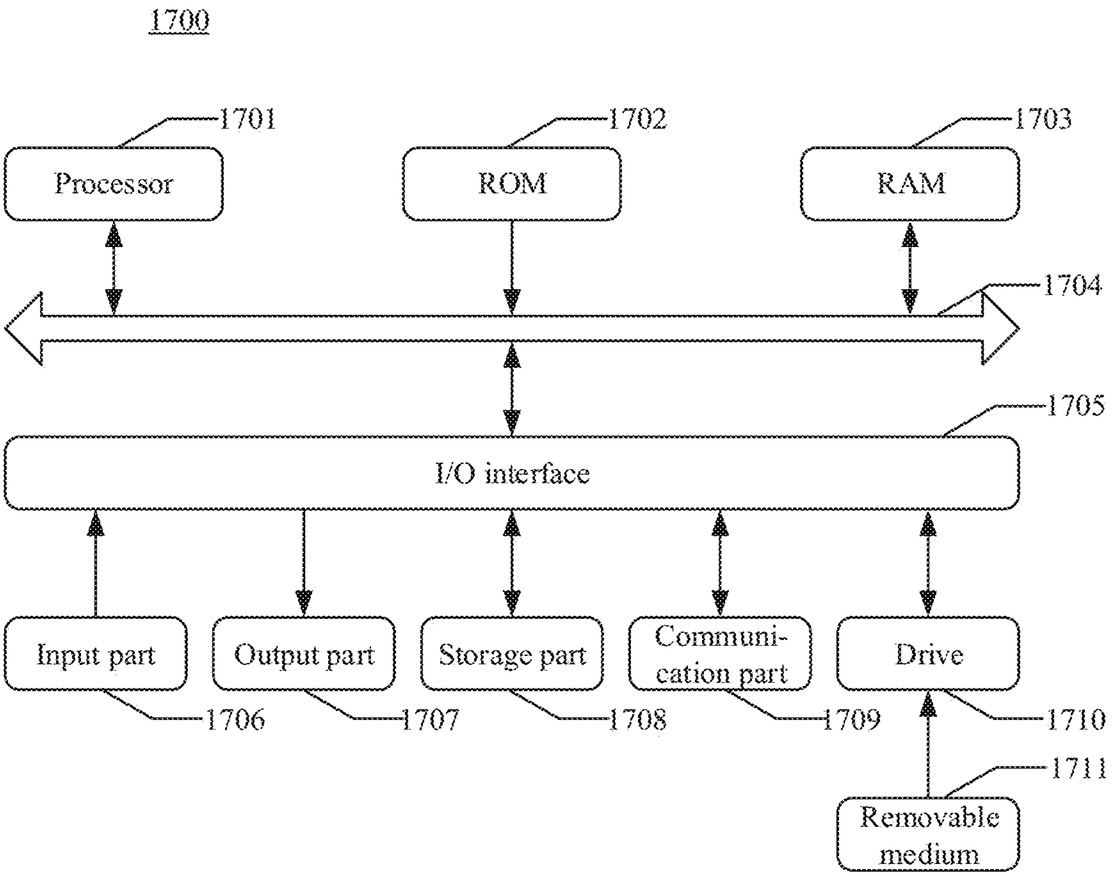
FIG. 17 schematically shows a block diagram of an electronic device applicable to implementation of the method of processing the medical data and the method of analyzing the medical data according to an embodiment of the present disclosure.

FIG. 17 schematically shows a block diagram of an electronic device applicable for implementing the method of processing the medical data and the method of analyzing the medical data according to embodiments of the present disclosure. The electronic device shown in FIG. 17 is just an example, and should not bring any limitation to functions and scopes of use of embodiments of the present disclosure.

As shown in FIG. 17, an electronic device 1700 according to embodiments of the present disclosure includes a processor 1701, which may execute various appropriate actions and processing according to the program stored in a read only memory (ROM) 1702 or the program loaded into a random access memory (RAM) 1703 from a storage part 1708. The processor 1701 may, for example, include a general-purpose microprocessor (for example, CPU), an instruction set processor and/or a related chipset and/or a special-purpose microprocessor (for example, an application specific integrated circuit (ASIC)), and the like. The processor 1701 may further include an on-board memory for caching. The processor 1701 may include a single processing unit or plurality of processing units for performing different actions of the method flow according to the embodiments of the present disclosure.

Various programs and data required for the operation of the device 1700 are stored in the RAM 1703. The processor 1701, the ROM 1702 and the RAM 1703 are connected to each other through a bus 1704. The processor 1701 executes various operations of the method flow according to embodiments of the present disclosure by executing the programs in the ROM 1702 and/or the RAM 1703. It should be noted that the program may also be stored in one or more memories other than the ROM 1702 and the RAM 1703. The processor 1701 may also execute various operations of the method flow according to embodiments of the present disclosure by executing the programs stored in the one or more memories.

According to embodiments of the present disclosure, the electronic device 1700 may further include an input/output (I/O) interface 1705 which is also connected to the bus 1704. The device 1700 may further include one or more of the following components connected to the I/O interface 1705: an input part 1706 including a keyboard, a mouse, etc.; an output part 1707 including a cathode ray tube (CRT), a liquid crystal display (LCD), etc. and a speaker, etc.; a storage part 1708 including a hard disk, etc.; and a communication part 1709 including a network interface card such as a LAN card, a modem, and the like. The communication part 1709 performs communication processing via a network such as the Internet. A drive 1710 is also connected to the I/O interface 1705 as required. A removable medium 1711, such as a magnetic disk, an optical disk, a magneto-optical disk, a semiconductor memory, and the like, is installed on the drive 1710 as required, so that the computer program read therefrom is installed into the storage part 1708 as needed.

The method flow according to embodiments of the present disclosure may be implemented as a computer software program. For example, embodiments of the present disclosure include a computer program product including a computer program carried on a computer-readable storage medium. The computer program includes a program code for execution of the method shown in the flowchart. In such embodiments, the computer program may be downloaded and installed from the network through the communication part 1709, and/or installed from the removable medium 1711. When the computer program is executed by the processor 1701, the above-mentioned functions defined in the system of embodiments of the present disclosure are performed. According to embodiments of the present disclosure, the above-described systems, apparatuses, devices, modules, units, etc. may be implemented by computer program modules.

The present disclosure further provides a computer-readable storage medium, which may be included in the apparatus/device/system described in the above embodiments; or exist alone without being assembled into the apparatus/device/system. The above-mentioned computer-readable storage medium carries one or more programs that when executed, perform the methods according to embodiments of the present disclosure.

According to embodiments of the present disclosure, the computer-readable storage medium may be a non-transitory computer-readable storage medium, for example, may include but not limited to: a portable computer disk, a hard disk, a random access memory (RAM), a read-only memory (ROM), an erasable programmable read-only memory (EPROM or flash memory), a portable compact disk read-only memory (CD-ROM), an optical storage device, a magnetic storage device, or any suitable combination of the above. In the present disclosure, the computer-readable storage medium may be any tangible medium that contains or stores programs that may be used by or in combination with an instruction execution system, apparatus or device.

For example, according to embodiments of the present disclosure, the computer-readable storage medium may include the above-mentioned ROM 1702 and/or RAM 1703 and/or one or more memories other than the ROM 1702 and RAM 1703.

Embodiments of the present disclosure further include a computer program product, which contains a computer program. The computer program contains program code for performing the method provided by embodiments of the present disclosure. When the computer program product runs on an electronic device, the program code causes the electronic device to implement the method of processing the medical data and the method of analyzing the medical data provided in embodiments of the present disclosure.

When the computer program is executed by the processor 1701, the above-mentioned functions defined in the system/apparatus of embodiments of the present disclosure are performed. According to embodiments of the present disclosure, the above-described systems, apparatuses, modules, units, etc. may be implemented by computer program modules.

In an embodiment, the computer program may rely on a tangible storage medium such as an optical storage device and a magnetic storage device. In another embodiment, the computer program may also be transmitted and distributed in the form of signals on a network medium, downloaded and installed through the communication part 1709, and/or installed from the removable medium 1711. The program code contained in the computer program may be transmitted by any suitable medium, including but not limited to a wireless one, a wired one, or any suitable combination of the above.

According to embodiments of the present disclosure, the program code for executing the computer programs provided by embodiments of the present disclosure may be written in any combination of one or more programming languages. In particular, these computing programs may be implemented using high-level procedures and/or object-oriented programming languages, and/or assembly/machine languages. Programming languages include, but are not limited to, Java, C++, Python, "C" language or similar programming languages. The program code may be completely executed on the user computing device, partially executed on the user device, partially executed on the remote computing device, or completely executed on the remote computing device or server. In a case of involving a remote computing device, the remote computing device may be connected to a user computing device through any kind of network, including a local area network (LAN) or a wide area networks (WAN), or may be connected to an external computing device (e.g., through the Internet using an Internet service provider).

The flowcharts and block diagrams in the accompanying drawings illustrate the possible architecture, functions, and operations of the system, method, and computer program product according to various embodiments of the present disclosure. In this regard, each block in the flowcharts or block diagrams may represent a part of a module, a program segment, or a code, which part includes one or more executable instructions for implementing the specified logical function. It should be further noted that, in some alternative implementations, the functions noted in the blocks may also occur in a different order from that noted in the accompanying drawings. For example, two blocks shown in succession may actually be executed substantially in parallel, or they may sometimes be executed in a reverse order, depending on the functions involved. It should be further noted that each block in the block diagrams or flowcharts, and the combination of blocks in the block diagrams or flowcharts, may be implemented by a dedicated hardware-based system that performs the specified functions or operations, or may be implemented by a combination of dedicated hardware and computer instructions. Those skilled in the art may understand that the various embodiments of the present disclosure and/or the features described in the claims may be combined in various ways, even if such combinations are not explicitly described in the present disclosure. In particular, without departing from the spirit and teachings of the present disclosure, the various embodiments of the present disclosure and/or the features described in the claims may be combined in various ways. All these combinations fall within the scope of the present disclosure.

Embodiments of the present disclosure have been described above. However, these embodiments are for illustrative purposes only, and are not intended to limit the scope of the present disclosure. Although the various embodiments have been described separately above, this does not mean that measures in the respective embodiments may not be used in combination advantageously. The scope of the present disclosure is defined by the appended claims and their equivalents. Those skilled in the art may make various substitutions and modifications without departing from the scope of the present disclosure, and these substitutions and modifications should all fall within the scope of the present disclosure.

What is claimed is:

1. A method of processing medical data, comprising:

jointly training a first feature extraction network, a second feature extraction network, a first classifier and a second classifier, acquiring first medical image data;

inputting the first medical image data into the first feature extraction network to obtain a first image feature; and obtaining a first gene mutation information according to the first image feature, wherein the first feature extraction network comprises a first feature extraction module configured to:

determine a first image query matrix and a first image key matrix according to the first medical image data;

determine a first image weight matrix according to the first image query matrix and the first image key matrix, wherein the first image weight matrix represents a correlation information between each two first medical images in the first medical image data; and determine the first image feature according to the first image weight matrix and the first medical image data;

wherein the first medical image data comprises a brain glioma image;

wherein the obtaining a first gene mutation information according to the first image feature comprises inputting the first image feature to the first classifier to obtain a brain glioma gene mutation type wherein the first classifier comprises a first classification network or a second classification network, wherein the jointly training comprises:

acquiring sample data, wherein the sample data comprises first sample medical image data, a sample gene mutation label information corresponding to the first sample medical image data, sample medical data, and a sample survival label information corresponding to the sample medical data, and the sample medical data comprises sample medical text data and second sample medical image data;

inputting the first sample medical image data into the first feature extraction network and the first classifier to obtain a first sample gene mutation prediction information corresponding to the first sample medical image data;

inputting the first sample gene mutation prediction information and the sample gene mutation label information into a first loss function to obtain a first loss function value;

inputting the sample medical data into the second feature extraction network and the second classifier to obtain a sample survival prediction information corresponding to the sample medical data;

inputting the sample survival prediction information and the sample survival label information into a second loss function to obtain a second loss function value; and adjusting a model parameter of the first feature extraction network, a model parameter of the second feature extraction network, a model parameter of the first classifier, and a model parameter of the second classifier according to the first loss function value and the second loss function value.

2. The method according to claim 1, wherein the first medical image data comprises a plurality of kinds of mono-modality medical image data, and the first feature extraction network comprises first feature extraction sub-networks respectively corresponding to the plurality of kinds of mono-modality medical image data;

wherein the inputting the first medical image data into a first feature extraction network to obtain a first image feature comprises:

inputting the plurality of kinds of mono-modality medical image data respectively into the first feature extraction sub-networks corresponding to the plurality of kinds of mono-modality medical image data, so as to obtain a plurality of mono-modality image features; and wherein the obtaining a first gene mutation information according to the first image feature comprises:

performing feature concatenating on the plurality of mono-modality image features to obtain a concatenated image feature; and inputting the concatenated image feature into the first classification network to obtain the first gene mutation information.

3. The method according to claim 1, wherein the first medical image data comprises multi-modality medical image data, and the first feature extraction network comprises a plurality of first feature extraction sub-networks;

wherein the inputting the first medical image data into a first feature extraction network to obtain a first image feature comprises:

inputting the multi-modality medical image data into the plurality of first feature extraction sub-networks to obtain a plurality of multi-modality image features; and wherein the obtaining a first gene mutation information according to the first image feature comprises:

inputting the plurality of multi-modality image features into the second classification network to obtain a plurality of predictions for single gene mutation types; and combining the plurality of predictions for single gene mutation types to obtain the first gene mutation information.

4. The method according to claim 3, wherein the second classification network comprises a plurality of second classification sub-networks respectively corresponding to the plurality of multi-modality image features; and wherein the inputting the plurality of multi-modality image features into the second classification network to obtain a plurality of predictions for single gene mutation types comprises:

inputting the plurality of multi-modality image features respectively into the second classification sub-networks corresponding to the plurality of multi-modality image features, so as to obtain the plurality of predictions for single gene mutation types.

5. The method according to claim 4, wherein the second classification sub-network comprises at least one selected from: an isocitrate dehydrogenase mutation classification network, a chromosome 1p/19q classification network, a telomerase reverse transcriptase promoter classification network, or an 06-methylguanine-DNA methyltransferase classification network.

6. The method according to claim 3, wherein the plurality of first feature extraction sub-networks share model parameters with each other.

7. The method according to claim 1, wherein determining the first image feature according to the first image weight matrix and the first medical image data comprises:

obtaining a first image value matrix according to the first medical image data; and obtaining the first image feature according to the first image weight matrix and the first image value matrix.

8. The method according to claim 1, further comprising: obtaining an image type information of the first medical image data according to device type conversion standard data corresponding to the first medical image data; wherein the method further comprises:

determining the image type information of the first medical image data according to medical image metadata corresponding to the first medical image data, in response to failing to determine the image type information of the first medical image data according to the device type conversion standard data corresponding to the first medical image data; and obtaining the image type information according to the first medical image data and the medical image metadata, in response to failing to determine the image type information according to the device type conversion standard data and failing to determine the image type information according to the medical image metadata.

9. The method according to claim 2, wherein the plurality of mono-modality medical image data comprises at least one selected from the group consisting of: mono-modality medical image data corresponding to an anatomical structure, mono-modality medical image data corresponding to a lesion site, mono-modality medical image data corresponding to an edema region, and mono-modality medical image data corresponding to a contrast enhancement.

10. A method of processing medical data, comprising:

jointly training a first feature extraction network, a second feature extraction network, a first classifier and a second classifier, acquiring first medical text data and first medical image data;

obtaining a first image feature according to the first medical image data;

inputting the first medical text data into the second feature extraction network to obtain a first text feature;

fusing the first image feature with the first text feature to obtain a first fusion feature; and obtaining a first survival information according to the first fusion feature, wherein the jointly training comprises:

acquiring sample data, wherein the sample data comprises first sample medical image data, a sample gene mutation label information corresponding to the first sample medical image data, sample medical data, and a sample survival label information corresponding to the sample medical data, and the sample medical data comprises sample medical text data and second sample medical image data;

inputting the first sample medical image data into the first feature extraction network and the first classifier to obtain a first sample gene mutation prediction information corresponding to the first sample medical image data;

inputting the first sample gene mutation prediction information and the sample gene mutation label information into a first loss function to obtain a first loss function value;

inputting the sample medical data into the second feature extraction network and the second classifier to obtain a sample survival prediction information corresponding to the sample medical data;

inputting the sample survival prediction information and the sample survival label information into a second loss function to obtain a second loss function value; and adjusting a model parameter of the first feature extraction network, a model parameter of the second feature extraction network, a model parameter of the first classifier, and a model parameter of the second classifier according to the first loss function value and the second loss function value.

11. The method according to claim 10, wherein the inputting the first medical text data into the second feature extraction network to obtain a first text feature comprises:

encoding the first medical text data to obtain a first medical text vector;

inputting the first medical text vector into a first encoder to obtain a first hidden vector;

inputting the first hidden vector into a first decoder to obtain a first decoded vector; and obtaining the first text feature according to the first hidden vector and the first decoded vector;

wherein the fusing the first image feature with the first text feature to obtain a first fusion feature comprises:

determining an image query matrix and an image key matrix according to the first medical image data;

determining a text query matrix and a text key matrix according to the first medical text data;

determining a first fusion weight matrix according to the image query matrix and the text key matrix;

determining a second fusion weight matrix according to the text query matrix and the image key matrix;

obtaining a first output feature vector according to the first fusion weight matrix and a text value matrix, wherein the text value matrix is obtained according to the first medical text data;

obtaining a second output feature vector according to the second fusion weight matrix and an image value matrix, wherein the image value matrix is obtained according to the first medical image data; and obtaining the first fusion feature according to the first output feature vector and the second output feature vector.

12. A method of analyzing medical data, comprising:

jointly training a first feature extraction network, a second feature extraction network, a first classifier and a second classifier, acquiring first medical text data and first medical image data;

inputting the first medical image data into the first feature extraction network to obtain a first image feature;

determining a gene mutation information according to the first image feature;

inputting the first medical text data into the second feature extraction network to obtain a text feature; and determining a survival information according to a fusion feature obtained from the first image feature and the text feature;

wherein the first feature extraction network comprises a first feature extraction module configured to:

determine an image query matrix and an image key matrix according to the first medical image data;

determine an image weight matrix according to the image query matrix and the image key matrix, wherein the image weight matrix represents a correlation information between each two medical images in the first medical image data; and determine the first image feature according to the image weight matrix and the first medical image data; and wherein the jointly training comprises:

acquiring sample data, wherein the sample data comprises first sample medical image data, a sample gene mutation label information corresponding to the first sample medical image data, sample medical data, and a sample survival label information corresponding to the sample medical data, and the sample medical data comprises sample medical text data and second sample medical image data;

inputting the first sample medical image data into the first feature extraction network and the first classifier to obtain a first sample gene mutation prediction information corresponding to the first sample medical image data;

inputting the first sample gene mutation prediction information and the sample gene mutation label information into a first loss function to obtain a first loss function value;

inputting the sample medical data into the second feature extraction network and the second classifier to obtain a sample survival prediction information corresponding to the sample medical data;

inputting the sample survival prediction information and the sample survival label information into a second loss function to obtain a second loss function value; and adjusting a model parameter of the first feature extraction network, a model parameter of the second feature extraction network, a model parameter of the first classifier, and a model parameter of the second classifier according to the first loss function value and the second loss function value.

13. The method according to claim 12, further comprising:

generating a test report according to the gene mutation information and the survival information, wherein the first medical image data comprises a plurality of medical images, and the first feature extraction network further comprises a second feature extraction module;

wherein the method further comprises: inputting the plurality of medical images into the second feature extraction module to obtain a temporal image feature, wherein the temporal image feature indicates a temporal relationship between the plurality of medical images;

wherein determining the image query matrix and the image key matrix according to the first medical image data comprises: inputting the temporal image feature into the first feature extraction module to obtain the image query matrix and the image key matrix;

wherein the first feature extraction network further comprises a third feature extraction module, and the third feature extraction module comprises a maximum pooling layer, a residual unit, a down-sampling unit, and an average pooling layer;

wherein the method further comprises:

inputting the plurality of medical images into the third feature extraction module to obtain an intermediate image feature; and wherein the inputting the plurality of medical images into the second feature extraction module to obtain a temporal image feature comprises:

inputting the intermediate image feature into the second feature extraction module to obtain the temporal image feature.

14. The method according to claim 12, wherein determining the first image feature according to the image weight matrix and the first medical image data comprises:

obtaining an image value matrix according to the first medical image data; and obtaining the first image feature according to the image weight matrix and the image value matrix;

wherein the inputting the first medical text data into a second feature extraction network to obtain a text feature comprises:

encoding the first medical text data to obtain a medical text vector;

inputting the medical text vector into an encoder to obtain a second hidden vector;

inputting the hidden vector into a decoder to obtain a decoded vector; and obtaining the text feature according to the hidden vector and the decoded vector;

wherein the determining a gene mutation information according to the first image feature comprises:

inputting the first image feature into the first classifier to obtain the gene mutation information; and wherein the determining a survival information according to a fusion feature obtained from the first image feature and the text feature comprises:

inputting the fusion feature obtained from the first image feature and the text feature into the second classifier a to obtain the survival information.

15. The method according to claim 14, wherein the adjusting the model parameter of the first feature extraction network, the model parameter of the second feature extraction network, the model parameter of the first classifier, and the model parameter of the second classifier according to the first loss function value and the second loss function value comprises:

adjusting the model parameter of the first feature extraction network and the model parameter of the first classifier according to the first loss function value; and adjusting the model parameter of the second feature extraction network and the model parameter of the second classifier according to the second loss function value, while maintaining the model parameter of the first feature extraction network and the model parameter of the first classifier unchanged;

or determining a total loss function value according to the first loss function value and the second loss function value; and adjusting the model parameter of the first feature extraction network, the model parameter of the second feature extraction network, the model parameter of the first classifier, and the model parameter of the second classifier according to the total loss function value.

16. An electronic device, comprising:

one or more processors; and a memory configured to store one or more programs, wherein the one or more programs are configured to, when executed by the one or more processors, cause the one or more processors to implement the method of claim 12.

17. A non-transitory computer readable storage medium having executable instructions stored therein, wherein the instructions are configured to, when executed by a processor, cause the processor to implement the method of claim 1.

18. The method according to claim 1, wherein the first medical image data comprises a plurality of first medical images;

wherein the first feature extraction network further comprises a second feature extraction module;

wherein the method further comprises: inputting the plurality of first medical images into the second feature extraction module to obtain a first temporal image feature, wherein the first temporal image feature represents a temporal relationship between the plurality of first medical images; and wherein determining the first image query matrix and the first image key matrix according to the first medical image data comprises: inputting the first temporal image feature into the first feature extraction module to obtain the first image query matrix and the first image key matrix.

19. The method according to claim 18, wherein the first feature extraction network further comprises a third feature extraction module, and the third feature extraction module comprises a first maximum pooling layer, a first residual unit, a first down-sampling unit, and a first average pooling layer;

wherein the method further comprises:

inputting the plurality of first medical images into the third feature extraction module to obtain a plurality of first intermediate image features; and wherein the inputting the plurality of first medical images into the second feature extraction module to obtain a first temporal image feature comprises:

inputting the plurality of first intermediate image features into the second feature extraction module to obtain the first temporal image feature.

* * * * *